US007297525B2

(12) United States Patent
Liu et al.

(10) Patent No.: US 7,297,525 B2
(45) Date of Patent: Nov. 20, 2007

(54) COMPOSITION EMPLOYING A NOVEL HUMAN KINASE

(75) Inventors: Wei Liu, Sudbury, MA (US); Leeying Wu, Lexington, MA (US); Huimin Chen, Bedford, MA (US)

(73) Assignee: Wyeth, Madison, NJ (US)

( * ) Notice: Subject to any disclaimer, the term of this patent is extended or adjusted under 35 U.S.C. 154(b) by 453 days.

(21) Appl. No.: 10/702,496

(22) Filed: Nov. 7, 2003

(65) Prior Publication Data

US 2004/0121383 A1 Jun. 24, 2004

Related U.S. Application Data

(60) Provisional application No. 60/429,381, filed on Nov. 27, 2002.

(51) Int. Cl.
*C12N 9/12* (2006.01)
*C12N 15/54* (2006.01)

(52) U.S. Cl. ...................................... 435/194; 536/23.2

(58) Field of Classification Search ................ 435/194; 536/23.2

See application file for complete search history.

(56) References Cited

U.S. PATENT DOCUMENTS

| | | | |
|---|---|---|---|
| 4,489,710 | A | 12/1984 | Spitler |
| 4,522,811 | A | 6/1985 | Eppstein et al. |
| 4,569,789 | A | 2/1986 | Blattler et al. |
| 4,625,014 | A | 11/1986 | Senter et al. |
| 4,638,045 | A | 1/1987 | Kohn et al. |
| 4,671,958 | A | 6/1987 | Rodwell et al. |
| 4,751,180 | A | 6/1988 | Cousens et al. |
| 4,935,233 | A | 6/1990 | Bell et al. |
| 5,459,039 | A | 10/1995 | Modrich et al. |
| 5,498,531 | A | 3/1996 | Jarrell |
| 5,919,619 | A | 7/1999 | Tullis |
| 6,506,559 | B1 | 1/2003 | Fire et al. |
| 2004/0038881 | A1 | 2/2004 | Bandman et al. |

FOREIGN PATENT DOCUMENTS

| | | |
|---|---|---|
| WO | WO 89/10134 | 11/1989 |
| WO | WO 97/07668 | 3/1997 |
| WO | WO 97/07669 | 3/1997 |
| WO | WO 99/14346 | 3/1999 |
| WO | WO 99/27132 | 6/1999 |
| WO | WO 00/44895 | 8/2000 |
| WO | WO 00/63364 | 10/2000 |
| WO | WO 00/73469 A2 | 12/2000 |
| WO | WO 01/29058 | 4/2001 |
| WO | WO 01/36646 | 5/2001 |
| WO | WO 01/66594 A2 | 9/2001 |
| WO | WO 01/68836 | 9/2001 |
| WO | WO 01/70949 | 9/2001 |
| WO | WO 01/75067 A2 | 10/2001 |
| WO | WO 01/75164 | 10/2001 |
| WO | WO 01/92513 | 12/2001 |
| WO | WO 02/08399 | 1/2002 |
| WO | WO 02/18557 A2 | 3/2002 |
| WO | WO 02/24924 | 3/2002 |
| WO | WO 02/24924 A2 | 3/2002 |
| WO | WO 02/46384 A2 | 6/2002 |
| WO | 02/81517/ | * 10/2002 |
| WO | WO 02/081731 A2 | 10/2002 |
| WO | WO 03/050084 A2 | 6/2003 |

OTHER PUBLICATIONS

PIR Accession No. AAC02941. (Feb. 1998).*

Hayashi, K. et al., "Activity and substrate specificity of the murine STK2 Serine/Threonine kinase that is structurally related to the mitotic regulator protein NIMA of *Aspergillus nidulans*," *Biochem. Biophys. Res. Commun.*, 264(2):449-56 (1999).

Aravind, L. and Koonin, E.V., "Phosphoesterase domains associated with DNA polymerases of diverse origins," *Nucleic Acids Res.*, 26(16):3746-52 (1998).

Meyers, R.M. et al., "Detection of single base substitutions by ribonuclease cleavage at mismatches in RNA:DNA duplexes," *Science*, vol. 230 (4731):1242-1246 (1985).

Database GenEmbl, on STN, AN AF021935, Leung, T. et al., "*Myotonic Dystrophy Kinase-Related Cdc42-Binding Kinase Acts as a Cdc42 Effector in Promoting Cytoskeletal Reorganization*," Sequence Comparison, pp. 18-21.

Collins, F.S., "Generation and initial analysis of more that 15,000 full-length human and mouse cDNA sequences," *Proc. Natl. Acad. Sci.* USA, 99(26):16899-16903 (2002).

Database GenCore on STN, AN AAD34229, Bandman, O. et al., Database N_Geneseq_Jan. 29, 2004 (WO 02/18557-A2), Mar. 7, 2002, Sequence Comparision, pp. 1-4.

Altschul et al.; "*Gapped Blast and PSI-Blast: A New Generation of Protein Database Search Programs*", Nucleic Acids Research, 1997, pp. 3389-3402, vol. 25, No. 17, Oxford University Press.

Berger P. et al.; "*Loss of Phosphatase Activity in Myotubularin-Related Protein 2 is Associated With Charcot-Marie Tooth Disease Type 4B1*", Human Molecular Genetics, 2002, pp. 1569-1579, vol. 11, No. 13, Oxford University Press.

Boe R. et al.; "*The Protein Phosphatase Inhibitor Okadaic Acid Induces Morphological Changes Typical of Apoptosis in Mammalian Cells*", Experimental Cell Research 195, 1991, pp. 237-246, Academic Press, Inc.

(Continued)

*Primary Examiner*—Rebecca E. Prouty
(74) *Attorney, Agent, or Firm*—Kirkpatrick & Lockhart Preston Gates Ellis LLP

(57) ABSTRACT

This invention provides compositions, organisms and methodologies employing a novel human protein kinase, MCRK1. The novel human kinase has sequence homology to rat myotonic dystrophy kinase-related Cdc42 binding kinase (MRCK) alpha. The gene encoding the novel kinase is localized in locus 11q13 of human chromosome 11. The novel protein kinase comprises multiple functional/structural domains that include a kinase domain, a pkinase_C domain, a DAG-PE binding domain, and a CNH domain. The sequence and structure similarity between the novel human protein and rat MRCK alpha indicates that the novel human protein may function as a downstream effector of Cdc42 in cytoskeleton reorganization.

1 Claim, 11 Drawing Sheets

OTHER PUBLICATIONS

Bottini N. et al.; "*Low-Molecular-Weight Protein Tyrosine Phosphatase and Human Disease: In Search of Biochemical Mechanisms*", Archivum Immunologiae et Therapiae Experimentalis, 2002 pp. 95-104, vol. 50.
Brown-Shimer, et al.; "*Effect of Protein Tyrosine Phosphatase 1b Expression on Transformation by the Human neu Oncogene*", Cancer Research, 52, 1992, pp. 478-448.
Chen et al.; "*The Myotonic Dystrophy Kinase-Related Cdc42-Binding Kinase is Involved in the Regulation of Neurite Outgrowth in PC12 Cells*", The Journal of Biological Chemistry 1999, pp. 19901-19905, vol. 274, No. 28, The American Society for Biochemistry and Molecular Biology, Inc.
Delagrave et al.; "*Recursive Ensemble Mutagenesis*", Protein Engineering, 1993, pp. 327-331, vol. 6 No. 3, Oxford University Press.
Dong et al.; "*Cdc42 Antagonizes Inductive Action of cAMP on Cell Shape, Via Effects of the Myotonic Dystropht Kinase-Related Cdc42-Binding Kinase (MRCK) on Myosin Light Chain Phosphorylation*", European Journal of Cell Biology Apr. 2002, pp. 231-242, vol. 81.
Engelman et al.; "*Identifying Nonpolar Transbilayer Helices in Amino Acid Sequences of Membrane Proteins*", Ann. Rev. Biophys. Chem. 1986, pp. 321-353, vol. 15, Annual Reviews Inc.
Florea et al.; "*A Computer Program for Aligning a cDNA Sequence With a Genomic DNA Sequence*", Genome Research 1998, pp. 967-974, vol. 8, Cold Spring Harbor Laboratory Press.
Gossen et al.; "*Transcriptional Activation by Tetracyclines in Mammalian Cells*", Science Jun. 23, 1995, pp. 1766-1769, vol. 268.
Guatelli et al.; "*Isothermal, In Vitro Amplification of Nucleic Acids by a Multienzyme Reaction Modeled After Retroviral Replication*", Proc. Natl. Acad. Sci. USA, Mar. 1990, pp. 1874-1878, vol. 87.
Haseloff et al.; "*Simple RNA Enzymes With New and Highly Specific Endoribonuclease Activities*", Nature, Aug. 18, 1988, pp. 585-591, vol. 334.
Hyrup et al.; "*Peptide Nucleic Acids (PNA): Synthesis, Properties and Potential Applications*", Bioorganic & Medicinal Chemistry, 1996, pp. 5-23, vol. 4, No. 1, Elsevier Science Ltd., Great Britain.
Ishida et al.; "*Treatment of Myeloid Leukemic Cells With the Phosphatase Inhibitor Okadaic Acid Induces Cell Cycle Arrest at Either G1/S or G2/M Depending on Dose*", Journal of Cellular Physiology, 1992, pp. 484-492.
Janssens et al.; "*Protein Phosphatase 2A: A Highly Regulated Familyof Serince/Threonine Phosphatases Implicated in Cell Growth and Signaliing,*" *Biochem, J.*, 353, 2001, pp. 417-443.
Kedra et al.; "*The Germinal Center Kinase Gene and a Novel CDC25-Like Gene are Located in the Vicinity of the PYGM Gene on 11q13*", Hum. Genet., 1997, pp. 611-619, vol. 100.
Keen et al.; *Rapid Detection of Single Base Mismatches as Heteroduplexes on Hydroling Gels*, Trends in Genetics, 1997, p. 5, vol. 7.
Kwoh et al.; "*Transcription-Based Amplification System and Detection of Amplified Human Immunodefieiency Virus Type 1 With a Bead-Based Sandwich Hybridization Format*", Proc. Natl. Acad. Sci. USA, Feb. 1989, pp. 1173-1177, VOI.. 86.
Lam et al.; "*Characterization of a Monoclonal Antibody Panel Shows That the Myotonic Dystrophy Protein Kinase, DMPK, is Expressed Almost Exclusively in Muscle and Heart*", Human Molecular Genetics, 2000, pp. 2167-2173, vol. 9, No. 4, Oxford University Press.
Lee et al.; "*Expression of Small Interfering RNAs Targeted Against HIV-1 rev Transcripts in Human Cells*", Nature Biotechnology, May 2002, pp. 500505, vol. 19.
Leung et al.; "*Myotonic Dystrophy Kinase-Related Cdc42-Binding Kinase Acts As a Cdc42 Effector in Promoting Cytoskeletal Reorganization*", Molecular and Cellular Biology, Jan. 1998, pp. 130-140, vol. 18, No. 1 American Society for Microbiology.
Lizardi et al.; "*Exponential Amplification of Recombinant-RNA Hybridizaion Probes*", Biotechnology, Oct. 1988, pp. 1197-1202, vol. 6.
Maratea et al.; "*Deletion and Fusion Analysis of the Phage Φx174 Lysis Gene E*", Gene, 1985, pp. 39-46, vol. 40, Elsevier Science Publishers.
Meyers et al.; "*Optimal Alignments in Linear Space*", Cabios, 1988, pp. 11-17, vol. 4, No. 1, Press Limited, Oxford England.
Murphy et al.; "*Genetic Construction, Expression, and Melanoma-Selective Cytotoxicity of a Diphtheria Toxin-Related α-Melanoma-Stimulating Hormone Fusion Protein*", Proc. Natl. Aca. Sci. USA, Nov. 1986, pp. 8258-8262, VO. 83.
Needleman et al.; "*A General Method Applicable to the Search for Similarities in the Amino Acid Sequence of Tow Proteins*", J. Mol. Bio., 1970, pp. 443-453, vol. 48.
No et al.; "*Ecdysone-Inducible Gene Expression in Mammalian Cells Transgenic Mice*", Proc. Natl. Acad. Sci. USA, Apr. 1996, pp. 3346-3351, vol. 93.
Nomura et al.; "*Enhancement by Cyclosporin A of Taxol-Induced Apoptosis of Human Urinary Bladder Cancer Cells*", Urol Res, 2002, pp. 102-111, vol. 30.
O'Gorman et al.; "*Recombinase-Mediated Gene Activation and Site-Specific Integration in Mammalian Cells*", Science, Mar. 1991, pp. 1351-1355.
Rosenbaum et al.; "*Temperature-Gradient Gel Electrophoresis*", Biophysical Chemistry, 1987, pp. 235-246, vol. 26.
Saiki et al.; "*Genetic Analysis of Amplified DNA With Immobilized Sequence-Specific Oligonucleotide Probes*", Proc. Natl. Acad. Sci. USA, Aug. 1989, pp. 6230-6234, vol. 86.
Straub et al.; "*Genome-Wide Scans of Three Independent Sets of 90 Irish Multiplex Schizophrenia Families and Follow-Up of Selected Regions in All Families Provides Evidence for Multiple Susceptibility Genes*", Mol. Psychiatry, 2002, pp. 542-559, vol. 7, No. 6.
Sui et al.; "*A DNA Vector-Based RNAi Technology to Suppress Gene Expression in Mammalian Cells*", Proc. Natl. Acad. Sci., Apr. 16, 2002, pp. 5515-5520, vol. 99, No. 8.
Tan et al.; "*Phosphorylation of a Novel Myosin Binding Subunit of Protein Phosphatase 1 Reveals a Conserved Mechanism in the Regulation of Actin Cytoskeleton*", The Journal of Biological Chemistry, 2001, pp. 21209-21216, vol. 276, No. 24.
Tan et al.; "*Intermolecular and Intramolecular Interactions Regulate Catalytic Activity of Myotonic Dystrophy Kinase-Related Cdc42-Binding Kinase α*", Molecular and Celluar Biology, Apr. 2001, pp. 2767-2778, vol. 21, No. 8.
Wang et al.; "*Ligand-Inducible and Liver-Specific Target Gene Expression in Transgenic Mice*", Nature Biotechnology, Mar. 1997, pp. 239-243, vol. 15.
Wilmut et al.; "*Viable Offspring Derived From Fetal and Adult Mammalian Cells*", Letters to Nature, Feb. 1997, pp. 810-813, vol. 385.
Ye et al.; "*Regulated Delivery of Therapeutic Proteins After In Vivo somatic Cell Gene Transfer*", Science, Jan. 1999, pp. 88-91, vol. 283.
Zhao et al.; "*Reversible Modification of Tissue-Type Plasminogen Activator by Methyphosphonate Esters*", Bioorganic & Medicinal Chemistry, 1996, pp. 523-529, vol. 4.
Zy; "*Protein Tyrosine Phosphatases: Structure and Function, Substrate Specificity, and Inhibitor Developmen*", Annu Rev Pharmacol Toxicol, 2002, pp. 209-234, vol. 42.

* cited by examiner

```
Query: 40  PLRRERSVAQFLSWASPFVSKVKELRLQRDDFEILKVIGRGAFGEVTVVRQRDTGQIFAM 99
           PLRRE+++ ++L WA PF SKVK++RL R+DFEILKVIGRGAFGEV VV+ ++  ++FAM
Sbjct: 46  PLRREKNILEYLEWAKPFTSKVKQMRLHREDFEILKVIGRGAFGEVAVVKLKNADKVFAM 105

Query: 100 KMLHKWEMLKRAETACFREERDVLVKGDSRWVTTLHYAFQDEEYLYLVMDYYAGGDLLTL 159
           K+L+KWEMLKRAETACFREERDVLV GDS+W+TTLHYAFQD+  LYLVMDYY GGDLLTL
Sbjct: 106 KILNKWEMLKRAETACFREERDVLVNGDSKWITTLHYAFQDDNNLYLVMDYYVGGDLLTL 165

Query: 160 LSRFEDRLPPELAQFYLAEMVLAIHSLHQLGYVHRDVKPDNVLLDVNGHIRLADFGSCLR 219
           LS+FEDRLP E+A+FYLAEMV+AI S+HQL YVHRD+KPDN+L+D+NGHIRLADFGSCL+
Sbjct: 166 LSKFEDRLPEEMARFYLAEMVIAIDSVHQLHYVHRDIKPDNILMDMNGHIRLADFGSCLK 225

Query: 220 LNTNGMVDSSVAVGTPDYISPEILQAMEEGKGHYGPQCDWWSLGVCAYELLFGETPFYAE 279
           L  +G V SSVAVGTPDYISPEILQAME+GKG YGP+CDWWSLGVC YE+L+GETPFYAE
Sbjct: 226 LMEDGTVQSSVAVGTPDYISPEILQAMEDGKGRYGPECDWWSLGVCMYEMLYGETPFYAE 285

Query: 280 SLVETYGKIMNHEDHLQFPPDVPDVPASAQDLIRQLLCRQEERLGRGGLDDFRNHPFFEG 339
           SLVETYGKIMNH++  QFP  V DV  +A+DLIR+L+C +E RLG+ G++DF+ HPFF G
Sbjct: 286 SLVETYGKIMNHKERFQFPTQVTDVSENAKDLIRRLICSREHRLGQNGIEDFKKHPFFSG 345

Query: 340 VDWERLASSTAPYIPELRGPMDTSNFDVDDDTLNHPGTLPPPSHGAFSGHHLPFVGFTYT 399
           +DW+ + +  APYIPE+  P DTSNFDVDDD L +   T+PPP+H AFSGHHLPFVGFTYT
Sbjct: 346 IDWDNIRNCEAPYIPEVSSPTDTSNFDVDDDCLKNSETMPPPTHTAFSGHHLPFVGFTYT 405

Query: 400 -----------------------XXXXXXXXXXXXXXXXXRKLQCLEQEKVELSRKHQ 434
                                                   R+++ LEQEK+EL+RK Q
Sbjct: 406 SSCVLSDRSCLRVTAGPTSLDLDVNVQRTLDNNLATEAYERRIKRLEQEKLELTRKLQ 463
```

FIGURE 1

```
Query: 551  RQVTQLQGQWEQRL----EESSQAKTIHTASETN---GMGPPEGGPQEAQLRKEVAALRE 603
            +++T+L+    E++      EE S+ + IH +    N      +   EG  Q+  L KE+  L++
Sbjct: 684  QEITKLKTDLEKKSIFYEEEISKREGIHASEIKNLKKELHDSEG--QQLALNKEIMVLKD 741

Query: 604  QLEQAHSHRPSGKEE-----------ALCXXXXXXXXXXXXXXXXXXXXXXXXXXXKQRLE 652
            +LE+       S +EE                                              Q LE
Sbjct: 742  KLEKTRRESQSEREEFENEFKQQYEREKVLLTEENKKLTSELDKLTSLYESLSLRNQHLE 801

Query: 653  GE------RRETESNWEAQLADILSWVNDEKVSRGYLQALATKMAEELESLRNVGTQTLP 706
             E       ++E+ ++WEAQ+ +I+ WV+DEK +RGYLQALA+KM EELE+LRN     +L
Sbjct: 802  EEVKDLADKKESVAHWEAQITEIIQWVSDEKDARGYLQALASKMTEELEALRN---SSLG 858

Query: 707  ARPLDHQWKARRLQKMEASARLELQSALEAEIRAKQGLQERLTQVQEAQLQAERRLQEAE 766
             R  D  WK RR  K++ SARLELQSAL+AEIRAKQ +QE L +V+ + +  E +L+++E
Sbjct: 859  TRATDMPWKMRRFAKLDMSARLELQSALDAEIRAKQAIQEELNKVKASNIITECKLKDSE 918

Query: 767  KQSQALQQELAML---REELRARGPVDTKPSNSLIPFLSFRSSEKDSAKDPGISGEATRH 823
            K++  L  E+  L     EELR+    V+ + S      FL+F ++  D+                +
Sbjct: 919  KKNLELLSEIEQLIKDTEELRSEKGVEHRDSQH--SFLAFLNTPTDALD---------QF 967

Query: 824  GGEPDLRPEGRRSLRMGAVFPRAPTANTASTEGLPAKGWGMGPWEALGNGCPPPQPGSHT 883
                 P   P G +  R+       P        T   +G PA   G                PP+   +H
Sbjct: 968  ERSPSCTPAG-KGRRIADSAPLPVHTPTLRKKGCPASA-GF-----------PPKRKTHQ 1014

Query: 884  LRPRSFPSPTKCLRCTSLMLGLGRQGLGCDACGYFCHTT-XXXXXXXXXXXXDLLRTALG 942
                +SF +PTKC +CTSLM+GL RQG  C+ CG+ CH T                 +  +  LG
Sbjct: 1015 FFVKSFTAPTKCHQCTSLMVGLIRQGCSCEVCGFSCHITCVNKAPTTCPVPPEQTKGPLG 1074

Query: 943  VHPETGTGTAYEGFLSVPRPSGVRRGWQRVFAALSDSRLLLFDAPDLRLSPPSGALLQVL 1002
            + P+  G GTAYEG  + +P+P+GV++GWQR   A + D +L  L+D   + + S PS    QV+
Sbjct: 1075 IDPQKGVGTAYEGHVRIPKPAGVKKGWQRALAVVCDFKLFLYDIAEGKASQPSSVISQVI 1134

Query: 1003 DLRDPQFSATPVLASDVIHAQSRDLPRIFRVTTSQLAVPPTTCTVLLLAESEGERERWXX 1062
            D+RD +FS + VLASDVIHA  +D+P IFRVT SQL+ P    C++L+LA+SE ER +W
Sbjct: 1135 DMRDEEFSVSSVLASDVIHASRKDIPCIFRVTASQLSAPSDKCSILMLADSETERSKWVG 1194

Query: 1063 XXXXXXXXXXXXXXXXXVYTLKEAYDNGLPLLPHTLCAAILDQDRLALGTEEGLFVIHL 1122
                              VY  KEAYD+ LPL+  T  AAI+D +R+ALG EEGLFV+H+
Sbjct: 1195 VLSELHKVLKKNKFRDRSVYVPKEAYDSTLPLIKTTQAAAIIDHERVALGNEEGLFVVHV 1254

Query: 1123 RSNDIFQVGECRRVQQLTLSPSAGLLVVLCGRGPSVRLFALAELENIEVAGAKIPESRGC 1182
              ++I +VG+ +++ Q+ L PS  L+ V+ GR    VRLF ++ L+  E    K+ E++GC
Sbjct: 1255 TKDEIIRVGDNKKIHQIELIPSDQLVAVISGRNRHVRLFPMSALDGRETDFYKLAETKGC 1314

Query: 1183 QVLAAGSILQARTPVLCVAVKRQVLCYQLGPGPGPWQRRIRELQAPATVQSLGLLGDRLC 1242
            Q +AAG +         LCVA+KRQVLCY+L             R+ +E+Q P  VQ + +  + LC
Sbjct: 1315 QTIAAGKVRHGALSCLCVAMKRQVLCYELFQSKTR-HRKFKEIQVPCNVQWMAIFSEHLC 1373

Query: 1243 VGAAGGFXXXXXXXXXXXXXXXXXXXVPEELPPSRXXXXXXXXXXXXXXXXXXXXXXXXAGI 1302
            VG   GF                      L                            GI
Sbjct: 1374 VGFQSGFLRYPLNGEGSPCNMLHSN-DHTLAFITHQPMDAICAVEISNKEYLLCFSSIGI 1432

Query: 1303 YVDGAGRKSRGHELLWPAAPMGWGYAAPYLTVFSENSIDVFDVRRAEWVQTVPLKKVRPL 1362
            Y D  GR+SR  EL+WPA P     Y APYL+++SEN++D+FDV   EW+QT+PLKKVRPL
Sbjct: 1433 YTDCQGRRSRQQELMWPANPSSCCYNAPYLSIYSENAVDIFDVNSMEWIQTLPLKKVRPL 1492

Query: 1363 NPEGSLFLYGTEKVRLTYLRNQLAEKDEFDIPDLTDNSRRQL-XXXXXXXXXXXXVSEEQ 1421
            N EGSL L G E +RL Y +N++AE DE  +P+ +DNSR+Q+                  V EE+
Sbjct: 1493 NTEGSLNLLGLETIRLIYFKNKMAEGDELVVPETSDNSRKQMVRNINNKRRYSFRVPEEE 1552

Query: 1422 QKQQRREMLKDPFVRSKLISPPTNFNHLVHVGPANG 1457
            + QQRREML+DP +R+KLIS PTNFNH+ H+GP +G
Sbjct: 1553 RMQQRREMLRDPEMRNKLISNPTNFNHIAHMGPGDG 1588
```

FIGURE 2

```
Query:  71  FEILKVIGRGAFGEVTVVRQRDTGQIFAMKMLHKWEMLKRAETACFREERDVLVKGDSRW  130
Sbjct:  1   YELLEVLGKGAFGKVYLARDKKTGKLVAIKVIKKEKLKKKKRERILRE-IKILKKLDHPN  59

Query:  131 VTTLHYAFQDEEYLYLVMDYYAGGDLLTLLSRFEDRLPPELAQFYLAEMVLAIHSLHQLG  190
Sbjct:  60  IVKLYDVFEDKDKLYLVMEYCEGGDLFDLLKK-RGRLSEDEARFYARQILSALEYLHSNG  118

Query:  191 YVHRDVKPDNVLLDVNGHIRLADFGSCLRLNTNGMVDSSVAVGTPDYISPEILQAMEEGK  250
Sbjct:  119 IIHRDLKPENILLDSDGHVKLADFGLAKQLDSGGTLLTTF-VGTPEYMAPEVLL-----G  172

Query:  251 GHYGPQCDWWSLGVCAYELLFGETPFYAESLVETYGKIMNHEDHLQFPPDVPDVPASAQD  310
Sbjct:  173 KGYGKAVDIWSLGVILYELLTGKPPFPGDDQLDALFKKIGKPPP-PFPPPEWKISPEAKD  231

Query:  311 LIRQLLCRQEERLGRGGLDDFRNHPFF  337
Sbjct:  232 LIKKLLVKDPEK--RLTAEEALEHPFF  256
```

FIGURE 3

```
Query:  71  FEILKVIGRGAFGEVTVVRQRDTGQIFAMKMLHKWEMLKRAETACFREERDVLVKGDSRW  130
Sbjct:  1   YELGEKLGSGSFGKVYKGKHKNTGEIVAIKKLKKESI---KEKKRFLREIRILRRLSHPN  57

Query:  131 VTTLHYAFQDEEYLYLVMDYYAGGDLLTLLSRFEDRLPPELAQFYLAEMVLAIHSLHQLG  190
Sbjct:  58  IVRLIGVFEEDDHLYLVMEYMEGGDLFDYLRRNGLLLSEKEAKKIALQILRGLEYLHSRG  117

Query:  191 YVHRDVKPDNVLLDVNGHIRLADFGSCLRLNTNGMVDSSVAVGTPDYISPEILQAMEEGK  250
Sbjct:  118 IVHRDLKPENILLDENGTVKIADFGLARLLKSSYSKLTTF-VGTPEYMAPEVLEG-----  171

Query:  251 GHYGPQCDWWSLGVCAYELLFGETPFYAESLVETYGKIMNHEDHLQFPPDVPDVPASAQD  310
Sbjct:  172 RGYSSKVDVWSLGVVLYELLTGKPPFSGIDPLEELFRIIKRGLRLPLPPNCSE---ELKD  228

Query:  311 LIRQLLCRQEERLGRGGLDDFRNHPFF  337
Sbjct:  229 LIKKCLNKDPEK--RPTAKEILNHPWF  253
```

FIGURE 4

```
Query:  72  ILKVIGRGAFGEV---TVVRQRDTGQIFAMKMLHKWEMLKRAETACFREERDVLVKGDS  128
Sbjct:  2   LGKKLGEGAFGEVYKGTLKGKGGKEVEVAVKTLKEDASEQ--QIEEFLREAKIMRKLDH  59

Query:  129 RWVTTLHYAFQDEEYLYLVMDYYAGGDLLTLLSRFEDRLPPELAQFYLAEMVLAIHS---  185
Sbjct:  60  PNIVKLLGVCTEEEPLMIVMEYMEGGDLLDYL---RKNRPKELSLSDLLSFALQIARGME  116

Query:  186 -LHQLGYVHRDVKPDNVLLDVNGHIRLADFGSCLRLNTNGMVDSSVAVGTPDYISPEILQ  244
Sbjct:  117 YLESKNFVHRDLAARNCLVGENKTVKIADFGLSRDLYSDDYYKVKGGKLPIRWMAPESLK  176

Query:  245 AMEEGKGHYGPQCDWWSLGVCAYELL-FGETPFYAESLVETYGKIMNHEDHLQFPPDVPD  303
Sbjct:  177 -----EGKFTSKSDVWSFGVLLWEIFTLGESPYPGMSNEEVLEYLKK-GYRLPQPPNCPD  230
```

FIGURE 5

```
Query:  339 GVDWERLAS--STAPYIPELRGPMDTSNFDVDDDTLNHPGTLPPPSHGAFSGHHLPFVGF  396

Sbjct:  2   GIDWDKLENKEIEPPFVPKIKSPTDTSNF--DPEFTEESPVLTPVDPPLSESDQDEFRGF  59


Query:  397 TY  398

Sbjct:  60  SY  61
```

FIGURE 6

```
Query: 339  GVDWERLASS--TAPYIPELRGPMDTSNFDVDDDTLNHPGTLPPPSHGAF-SGHHLPFVG 395
Sbjct:  2   NIDWDKLENKEIEPPFKPKIKSPRDTSNF--DKEFTREKPVLTPVDSVLIRSIDQNEFRG  59

Query:  396 FTY  398
Sbjct:  60  FSY  62
```

FIGURE 7

```
Query:  882   HTLRPRSFPSPTKCLRCTSLMLGLGRQGLGCDACGYFCH  920
Sbjct:  1     HRFKRTSFRQPTFCDHCGEFIWGLGKQGLKCSNCGLVVH  39
```

FIGURE 8

```
Query: 953  YEGFLSVPRPSGVRRGWQRVFAALSDSRLLLFDAPDLRLSPPSGALLQVLDLRDPQFSAT 1012
Sbjct:   3  KEGWLLK-KSSGGKKSWKKRYFVLFNGVLLYYKSKK---KKSSSKPKGSIPLSGCTVREA 58

Query: 1013 PVLASDVIHAQSRDLPRIFRVTTSQLAVPPTTCTVLLLAESEGERERW 1060
Sbjct:   59 P-------DSDSDKKKNCFEIVT------PDRKTLLLQAESEEEREEW 93
```

FIGURE 9

```
Query: 954  EGFLSVPRPSGVRRGWQRVFAALSDSRLLLFDAPDLRLSPPSGALLQVLDLRDPQFSATP 1013
Sbjct:   4  EGWLLK-KSTVKKKRWKKRYFFLFNDVLIYYKSKKKSYEPKG-----SIPLSGCSVEDVP 57

Query: 1014 VLASDVIHAQSRDLPRIFRVTTSQLAVPPTTCTVLLLAESEGERERW 1060
Sbjct:   58 --------DSEFKRPNCFQLVTRD-----GKETFILQAESEEERQDW 91
```

FIGURE 10

```
Query: 1102 AILDQDRLALGTEEGLFVIHLRSN-DIFQVGECRRVQQLTLSPSAGLLVVLCGRGPSVRL 1160
Sbjct:    8 PYTIEDNLLVGTEEGLFFLNRSQQRNLMRIAGPRSVTQLEIMAELNCLAMIAGKSGQLRM   67

Query: 1161 FALAELENIEVAGAKIPES----------RGCQVLAAGSILQARTPVLCVAVKRQVLCYQ 1210
Sbjct:   68 IPLDSLILRALQSTQLSARPEILPEFEDVKGCIKYHVQKG--ERFLFICDALHSSVVKYN  125

Query: 1211 LGPGPGPWQRRIRELQAPATVQSLGLL----GDRLCVGAAGGFALYPLLNEAAPLALGAG 1266
Sbjct:  126 ATYDPFSKFAKFRV-PEPTPLPEPISLTESAPSGIIIGCDTFYYVVLDHQTSNVSARDLS  184

Query: 1267 LVPEELPPSRGGLGEALGAVELSLSEFLLLFTTAGIYVDGAGRKSRGHELLWPAAPMGWG 1326
Sbjct:  185 -----LPNKNEFSEGPISVIIVNQNEVLLCYQNQGVFVNLYGRQSRTETIEWEEMPMAFA  239

Query: 1327 YAAPYLTVFSENSIDVFDV  1345
Sbjct:  240 YTEPFLYIVHDDSIEILEI  258
```

FIGURE 11

```
Query:  1440  ISPPTNFNHLVHVGPANGRPGARDKSPPPWAA  1471
Sbjct:  1     ISTPTNFKHIAHVGF-DGQTGEFTGLPTEWES  31
```

FIGURE 12

```
Query: 648 KQRLEGERRETESNWEAQLADILSWVNDEKVSRGYLQALATKMAEELESLRN--------  699
Sbjct: 173 KAKLNAEKKA--KQLESQLSELQVKLDELQRQLNDLTSQKSRLQSENSDLTRQLEEAEAQ  230

Query: 700 VGTQTLPARPLDHQWK-ARRLQKMEASARLELQSALEAEIRAKQGLQERLTQVQEAQLQA  758
Sbjct: 231 VSNLSKLKSQLESQLEEAKRSLEEESRERANLQAQLRQLEHDLDSLREQLEEESEAKAEL  290

Query: 759 ERRLQEAEKQSQALQQEL---AMLR----EELRAR  786
Sbjct: 291 ERQLSKANAEIQQWRSKFESEGALRAEELEELKKK  325
```

FIGURE 13

| GES | | |
|---|---|---|
| **Peak Range** | **Peak Type** | **Peak Height** |
| 386 - 397 | Putative | 0.944 |
| 924 - 924 | Putative | 0.543 |
| 1040 - 1046 | Putative | 1.149 |
| 1144 - 1149 | Putative | 1.023 |
| 1246 - 1260 | Putative | 0.768 |
| 1289 - 1300 | Putative | 1.039 |
| 1322 - 1330 | Putative | 1.226 |
| 1539 - 1540 | Putative | 0.582 |

SEQUENCE LISTING

<160> NUMBER OF SEQ ID NOS: 306

<210> SEQ ID NO 1
<211> LENGTH: 4698
<212> TYPE: DNA
<213> ORGANISM: Homo sapiens

<400> SEQUENCE: 1

```
atggagcggc ggctgcgcgc gctggagcag ctggcgcggg gcgaggccgg cggctgcccg     60
gggctcgacg gcctcctaga tctgctgctg gcgctgcacc acgagctcag cagcggcccc    120
ctacggcggg agcgcagcgt ggcgcagttc ctgagctggg ccagcccctt cgtatcaaag    180
gtgaaagaac tgcgtctgca gagagatgac tttgagatct tgaaggtgat cggccgagga    240
gcctttgggg aggtcaccgt ggtgaggcag agggacactg ggcagatttt tgccatgaaa    300
atgctgcaca agtgggagat gctgaagagg gctgagacag cctgtttccg ggaggagcgg    360
gatgtgctcg tgaaagggga cagccgttgg gtgaccactc tgcactatgc cttccaagac    420
gaggagtacc tgtaccttgt gatggactac tatgctggtg gggacctcct gacgctgctg    480
agccgcttcg aggaccgtct cccgcccgag ctggcccagt tctacctggc tgagatggtg    540
ctggccatcc actcgctgca ccagctgggt tatgtccaca gggatgtcaa gccagacaac    600
gtcctgctgg atgtgaacgg gcacattcgc ctggctgact tcggctcctg cctgcgtctc    660
aacaccaacg gcatggtgga ttcatcagtg gcagtaggga cgccggacta tatctcccct    720
gagatcctgc aggccatgga ggagggcaag ggccactacg gcccacagtg tgactggtgg    780
tcgcttggag tctgcgccta tgagctgctc tttggggaga cgcccttcta tgctgagtcc    840
ttggtggaaa cctacggcaa gatcatgaac cacgaggacc acctgcagtt cccccccggac   900
gtgcctgacg tgccagccag cgcccaagac ctgatccgcc agctgctgtg tcgccaggaa    960
gagcggctag gccgtggtgg gctggatgac ttccggaacc atcctttctt cgaaggcgtg   1020
gactgggagc ggctggcgag cagcacggcc ccctatattc ctgagctgcg gggacccatg   1080
gacacctcca actttgatgt ggatgacgac accctcaacc atccagggac cctgccaccg   1140
ccctcccacg gggccttctc cggccatcac ctgccattcg tgggcttcac ctacacctca   1200
ggcagtcaca gtcctgagag cagctctgag gcttgggctg ccctggagcg gaagctccag   1260
tgtctggagc aggagaaggt ggagctgagc aggaagcacc aaggggctgc tgctgcggga   1320
atggaggagt ggactcacct gtgggtacca cctcccctcc agaggccctg cacgccccca   1380
cagaccatcg ggagctggag cagctacgga aggaagtgca gactctgcgg gacaggctgc   1440
caggagctgg ccgagggtcg ggcagggctg caggctcagg agcaggagct ctgcagggcc   1500
caggggcagc aggaggagct gcttcagagg ctacaggagg cccaggagag agaggcggcc   1560
acagctagcc agacccgggc cctgagctcc cagctggagg aagcccgggc tgcccagagg   1620
gagctggagg cccaggtgtc ctccctgagc cggcaggtga cgcagctgca gggacagtgg   1680
gagcaacgcc ttgaggagtc gtcccaggcc aagaccatcc acacagcctc tgagaccaac   1740
gggatgggac cccctgaggg tgggcctcag gaggcccaac tgaggaagga ggtggccgcc   1800
ctgcgagagc agctggagca ggcccacagc cacaggccga gtggtaagga ggaggctctg   1860
tgccagctgc aggaggaaaa ccggaggctg agccgggagc aggagcggct agaagcagag   1920
ctggcccagg agcaggagag caagcagcgg ctggagggtg agcggcggga gacggagagc   1980
aactgggagg cccagctcgc cgacatcctc agctgggtga atgatgagaa ggtctcaaga   2040
```

```
ggctacctgc aggccctggc caccaagatg gcagaggagc tggagtcctt gaggaacgta   2100
ggcacccaga cgctccctgc ccggccactg gaccaccagt ggaaggcgcg gcgactgcag   2160
aagatggagg cctcggccag gctggagctg cagtcagcgc tggaggccga gatccgcgcc   2220
aagcagggcc tgcaggagcg gctgacacag gtgcaggagg cccagctgca ggctgagcgc   2280
cgtctgcagg aggccgagaa gcagagccag gccctgcaac aggagctcgc catgctgcgg   2340
gaggagctgc gggcccgagg gccagtggac accaagccct caaactccct gattcccttc   2400
ctgtccttcc ggagctcaga gaaggattct gccaaggacc ctggcatctc aggagaggcc   2460
acaaggcatg gaggagagcc agatctgagg ccggagggcc gacgcagcct gcgcatgggg   2520
gctgtgttcc ccagagcacc cactgccaac acagcctcta cagaaggtct tcctgctaag   2580
ggatggggca tggggccctg ggaggccttg ggtaatggct gtccccctcc ccagcccggc   2640
tcacacacgc tgcgcccccg gagcttccca tccccgacca agtgtctccg ctgcacctcg   2700
ctgatgctgg gcctgggccg ccagggcctg ggttgtgatg cctgcggcta cttttgtcac   2760
acaacctgtg ccccacaggc cccaccctgc cccgtgcccc ctgacctcct ccgcacagcc   2820
ctgggagtac accccgaaac aggcacaggc actgcctatg agggctttct gtcggtgccg   2880
cggccctcag gtgtccggcg ggctggcag cgcgtgtttg ctgccctgag tgactcacgc   2940
ctgctgctgt ttgacgcccc tgacctgagg ctcagcccgc ccagtggggc cctcctgcag   3000
gtcctagatc tgagggaccc ccagttctcg gctaccccctg tcctggcctc tgatgttatc   3060
catgcccaat ccagggacct gccacgcatc tttagggtga caacctccca gctggcagtg   3120
ccgcccacca cgtgcactgt gctgctgctg gcagagagcg agggggagcg ggaacgctgg   3180
ctgcaggtgc tgggtgagct gcagcggctg ctgctggacg cgcggccaag accccggccc   3240
gtgtacacac tcaaggaggc ttacgacaac gggctgccgc tgctgcctca cacgctctgc   3300
gctgccatcc tcgaccagga tcgacttgcg cttggcaccg aggaggggct ctttgtcatc   3360
catctgcgca gcaacgacat cttccaggtg ggggagtgcc ggcgcgtgca gcagctgacc   3420
ttgagcccca gtgcaggcct gctggtcgtg ctgtgtggcc gcggccccag cgtgcgtctc   3480
tttgccctgg cggagctgga gaacatagag gtagcaggtg ccaagatccc cgagtctcga   3540
ggctgccagg tgctggcagc tggaagcatc ctgcaggccc gcaccccggt gctctgtgta   3600
gccgtcaagc gccaggtgct ctgctaccag ctgggcccgg gccctgggcc ctggcagcgc   3660
cgcatccgtg agctgcaggc acctgccact gtgcagagcc tggggctgct gggcgaccgg   3720
ctatgtgtgg gcgccgccgg tggctttgca ctctacccgc tgctcaacga ggctgcgccg   3780
ttggcgctgg gggccggttt ggtgcctgag gagctgccac catcccgcgg gggcctgggt   3840
gaggcactgg gtgccgtgga gcttagcctc agcgagttcc tgctactctt caccactgct   3900
ggcatctacg tggatggcgc aggccgcaag tctcgtggcc acgagctgtt gtggccagca   3960
gcgcccatgg gctgggggta tgcggccccc tacctgacag tgttcagcga gaactccatc   4020
gatgtgtttg acgtgaggag ggcagaatgg gtgcagaccg tgccgctcaa gaaggtgcgg   4080
cccctcaatc cagagggctc cctgttcctc tacggcaccg agaaggtccg cctgacctac   4140
ctcaggaacc agctggcaga gaaggacgag ttcgacatcc cggacctcac cgacaacagc   4200
cggcgccagc tgttccgcac caagagcaag cgccgcttct tttccgcgt gtcggaggag   4260
cagcagaagc agcagcgcag ggagatgctg aaggaccctt ttgtgcgctc caagctcatc   4320
tcgccgccta ccaacttcaa ccacctagta cacgtgggcc ctgccaacgg gcggcccggc   4380
gccagggaca agtccccgcc tccatgggca gcgaaggcct cggtggagac gcagacccca   4440
```

gtaagggcag cccctcagcc tccagtgtgc caccccccac cccaagtttc tacccccttt 4500
ggatccctga aatctgatct tggtattttt gtctcctcgt ctgctgctgg agcagtgaag 4560
aggaaaccct ggacatccct gtccagcgag tctgtgtcct gcccccaggg atcgctgagc 4620
cctgcaacct ccctaatgca ggtctcagaa cggccccgaa gcctcccccct atcccctgaa 4680 ttggagagct ctccttga 4698

<210> SEQ ID NO 2
<211> LENGTH: 1565
<212> TYPE: PRT
<213> ORGANISM: Homo sapiens

<400> SEQUENCE: 2

```
Met Glu Arg Arg Leu Arg Ala Leu Glu Gln Leu Ala Arg Gly Glu Ala
1               5                   10                  15

Gly Gly Cys Pro Gly Leu Asp Gly Leu Leu Asp Leu Leu Leu Ala Leu
            20                  25                  30

His His Glu Leu Ser Ser Gly Pro Leu Arg Arg Glu Arg Ser Val Ala
        35                  40                  45

Gln Phe Leu Ser Trp Ala Ser Pro Phe Val Ser Lys Val Lys Glu Leu
    50                  55                  60

Arg Leu Gln Arg Asp Asp Phe Glu Ile Leu Lys Val Ile Gly Arg Gly
65                  70                  75                  80

Ala Phe Gly Glu Val Thr Val Val Arg Gln Arg Asp Thr Gly Gln Ile
                85                  90                  95

Phe Ala Met Lys Met Leu His Lys Trp Glu Met Leu Lys Arg Ala Glu
            100                 105                 110

Thr Ala Cys Phe Arg Glu Glu Arg Asp Val Leu Val Lys Gly Asp Ser
        115                 120                 125

Arg Trp Val Thr Thr Leu His Tyr Ala Phe Gln Asp Glu Glu Tyr Leu
    130                 135                 140

Tyr Leu Val Met Asp Tyr Tyr Ala Gly Gly Asp Leu Leu Thr Leu Leu
145                 150                 155                 160

Ser Arg Phe Glu Asp Arg Leu Pro Pro Glu Leu Ala Gln Phe Tyr Leu
                165                 170                 175

Ala Glu Met Val Leu Ala Ile His Ser Leu His Gln Leu Gly Tyr Val
            180                 185                 190

His Arg Asp Val Lys Pro Asp Asn Val Leu Leu Asp Val Asn Gly His
        195                 200                 205

Ile Arg Leu Ala Asp Phe Gly Ser Cys Leu Arg Leu Asn Thr Asn Gly
    210                 215                 220

Met Val Asp Ser Ser Val Ala Val Gly Thr Pro Asp Tyr Ile Ser Pro
225                 230                 235                 240

Glu Ile Leu Gln Ala Met Glu Glu Gly Lys Gly His Tyr Gly Pro Gln
                245                 250                 255

Cys Asp Trp Trp Ser Leu Gly Val Cys Ala Tyr Glu Leu Leu Phe Gly
            260                 265                 270

Glu Thr Pro Phe Tyr Ala Glu Ser Leu Val Glu Thr Tyr Gly Lys Ile
        275                 280                 285

Met Asn His Glu Asp His Leu Gln Phe Pro Pro Asp Val Pro Asp Val
    290                 295                 300

Pro Ala Ser Ala Gln Asp Leu Ile Arg Gln Leu Leu Cys Arg Gln Glu
305                 310                 315                 320

Glu Arg Leu Gly Arg Gly Gly Leu Asp Asp Phe Arg Asn His Pro Phe
                325                 330                 335
```

```
Phe Glu Gly Val Asp Trp Glu Arg Leu Ala Ser Ser Thr Ala Pro Tyr
            340                 345                 350

Ile Pro Glu Leu Arg Gly Pro Met Asp Thr Ser Asn Phe Asp Val Asp
        355                 360                 365

Asp Asp Thr Leu Asn His Pro Gly Thr Leu Pro Pro Pro Ser His Gly
    370                 375                 380

Ala Phe Ser Gly His His Leu Pro Phe Val Gly Phe Thr Tyr Thr Ser
385                 390                 395                 400

Gly Ser His Ser Pro Glu Ser Ser Ser Glu Ala Trp Ala Ala Leu Glu
                405                 410                 415

Arg Lys Leu Gln Cys Leu Glu Gln Glu Lys Val Glu Leu Ser Arg Lys
            420                 425                 430

His Gln Gly Ala Ala Ala Ala Gly Met Glu Glu Trp Thr His Leu Trp
        435                 440                 445

Val Pro Pro Pro Leu Gln Arg Pro Cys Thr Pro Pro Gln Thr Ile Gly
    450                 455                 460

Ser Trp Ser Ser Tyr Gly Arg Lys Cys Arg Leu Cys Gly Thr Gly Cys
465                 470                 475                 480

Gln Glu Leu Ala Glu Gly Arg Ala Gly Leu Gln Ala Gln Glu Gln Glu
                485                 490                 495

Leu Cys Arg Ala Gln Gly Gln Gln Glu Glu Leu Leu Gln Arg Leu Gln
            500                 505                 510

Glu Ala Gln Glu Arg Glu Ala Ala Thr Ala Ser Gln Thr Arg Ala Leu
        515                 520                 525

Ser Ser Gln Leu Glu Glu Ala Arg Ala Ala Gln Arg Glu Leu Glu Ala
    530                 535                 540

Gln Val Ser Ser Leu Ser Arg Gln Val Thr Gln Leu Gln Gly Gln Trp
545                 550                 555                 560

Glu Gln Arg Leu Glu Glu Ser Ser Gln Ala Lys Thr Ile His Thr Ala
                565                 570                 575

Ser Glu Thr Asn Gly Met Gly Pro Pro Glu Gly Gly Pro Gln Glu Ala
            580                 585                 590

Gln Leu Arg Lys Glu Val Ala Ala Leu Arg Glu Gln Leu Glu Gln Ala
        595                 600                 605

His Ser His Arg Pro Ser Gly Lys Glu Glu Ala Leu Cys Gln Leu Gln
    610                 615                 620

Glu Glu Asn Arg Arg Leu Ser Arg Glu Gln Glu Arg Leu Glu Ala Glu
625                 630                 635                 640

Leu Ala Gln Glu Gln Glu Ser Lys Gln Arg Leu Glu Gly Glu Arg Arg
                645                 650                 655

Glu Thr Glu Ser Asn Trp Glu Ala Gln Leu Ala Asp Ile Leu Ser Trp
            660                 665                 670

Val Asn Asp Glu Lys Val Ser Arg Gly Tyr Leu Gln Ala Leu Ala Thr
        675                 680                 685

Lys Met Ala Glu Glu Leu Glu Ser Leu Arg Asn Val Gly Thr Gln Thr
    690                 695                 700

Leu Pro Ala Arg Pro Leu Asp His Gln Trp Lys Ala Arg Arg Leu Gln
705                 710                 715                 720

Lys Met Glu Ala Ser Ala Arg Leu Glu Leu Gln Ser Ala Leu Glu Ala
                725                 730                 735

Glu Ile Arg Ala Lys Gln Gly Leu Gln Glu Arg Leu Thr Gln Val Gln
            740                 745                 750

Glu Ala Gln Leu Gln Ala Glu Arg Arg Leu Gln Glu Ala Glu Lys Gln
```

```
        755                 760                 765

Ser Gln Ala Leu Gln Gln Glu Leu Ala Met Leu Arg Glu Glu Leu Arg
    770                 775                 780

Ala Arg Gly Pro Val Asp Thr Lys Pro Ser Asn Ser Leu Ile Pro Phe
785                 790                 795                 800

Leu Ser Phe Arg Ser Ser Glu Lys Asp Ser Ala Lys Asp Pro Gly Ile
                805                 810                 815

Ser Gly Glu Ala Thr Arg His Gly Gly Glu Pro Asp Leu Arg Pro Glu
            820                 825                 830

Gly Arg Arg Ser Leu Arg Met Gly Ala Val Phe Pro Arg Ala Pro Thr
        835                 840                 845

Ala Asn Thr Ala Ser Thr Glu Gly Leu Pro Ala Lys Gly Trp Gly Met
    850                 855                 860

Gly Pro Trp Glu Ala Leu Gly Asn Gly Cys Pro Pro Pro Gln Pro Gly
865                 870                 875                 880

Ser His Thr Leu Arg Pro Arg Ser Phe Pro Ser Pro Thr Lys Cys Leu
                885                 890                 895

Arg Cys Thr Ser Leu Met Leu Gly Leu Gly Arg Gln Gly Leu Gly Cys
            900                 905                 910

Asp Ala Cys Gly Tyr Phe Cys His Thr Thr Cys Ala Pro Gln Ala Pro
        915                 920                 925

Pro Cys Pro Val Pro Pro Asp Leu Leu Arg Thr Ala Leu Gly Val His
    930                 935                 940

Pro Glu Thr Gly Thr Gly Thr Ala Tyr Glu Gly Phe Leu Ser Val Pro
945                 950                 955                 960

Arg Pro Ser Gly Val Arg Arg Gly Trp Gln Arg Val Phe Ala Ala Leu
                965                 970                 975

Ser Asp Ser Arg Leu Leu Leu Phe Asp Ala Pro Asp Leu Arg Leu Ser
            980                 985                 990

Pro Pro Ser Gly Ala Leu Leu Gln  Val Leu Asp Leu Arg  Asp Pro Gln
        995                 1000                1005

Phe Ser  Ala Thr Pro Val Leu  Ala Ser Asp Val Ile  His Ala Gln
    1010                1015                1020

Ser Arg  Asp Leu Pro Arg Ile  Phe Arg Val Thr Thr  Ser Gln Leu
    1025                1030                1035

Ala Val  Pro Pro Thr Thr Cys  Thr Val Leu Leu Leu  Ala Glu Ser
    1040                1045                1050

Glu Gly  Glu Arg Glu Arg Trp  Leu Gln Val Leu Gly  Glu Leu Gln
    1055                1060                1065

Arg Leu  Leu Leu Asp Ala Arg  Pro Arg Pro Arg Pro  Val Tyr Thr
    1070                1075                1080

Leu Lys  Glu Ala Tyr Asp Asn  Gly Leu Pro Leu Leu  Pro His Thr
    1085                1090                1095

Leu Cys  Ala Ala Ile Leu Asp  Gln Asp Arg Leu Ala  Leu Gly Thr
    1100                1105                1110

Glu Glu  Gly Leu Phe Val Ile  His Leu Arg Ser Asn  Asp Ile Phe
    1115                1120                1125

Gln Val  Gly Glu Cys Arg Arg  Val Gln Gln Leu Thr  Leu Ser Pro
    1130                1135                1140

Ser Ala  Gly Leu Leu Val Val  Leu Cys Gly Arg Gly  Pro Ser Val
    1145                1150                1155

Arg Leu  Phe Ala Leu Ala Glu  Leu Glu Asn Ile Glu  Val Ala Gly
    1160                1165                1170
```

```
Ala Lys  Ile Pro Glu Ser Arg  Gly Cys Gln Val Leu  Ala Ala Gly
    1175                 1180                 1185

Ser Ile  Leu Gln Ala Arg Thr  Pro Val Leu Cys Val  Ala Val Lys
    1190                 1195                 1200

Arg Gln  Val Leu Cys Tyr Gln  Leu Gly Pro Gly Pro  Gly Pro Trp
    1205                 1210                 1215

Gln Arg  Arg Ile Arg Glu Leu  Gln Ala Pro Ala Thr  Val Gln Ser
    1220                 1225                 1230

Leu Gly  Leu Leu Gly Asp Arg  Leu Cys Val Gly Ala  Ala Gly Gly
    1235                 1240                 1245

Phe Ala  Leu Tyr Pro Leu Leu  Asn Glu Ala Ala Pro  Leu Ala Leu
    1250                 1255                 1260

Gly Ala  Gly Leu Val Pro Glu  Glu Leu Pro Pro Ser  Arg Gly Gly
    1265                 1270                 1275

Leu Gly  Glu Ala Leu Gly Ala  Val Glu Leu Ser Leu  Ser Glu Phe
    1280                 1285                 1290

Leu Leu  Leu Phe Thr Thr Ala  Gly Ile Tyr Val Asp  Gly Ala Gly
    1295                 1300                 1305

Arg Lys  Ser Arg Gly His Glu  Leu Leu Trp Pro Ala  Ala Pro Met
    1310                 1315                 1320

Gly Trp  Gly Tyr Ala Ala Pro  Tyr Leu Thr Val Phe  Ser Glu Asn
    1325                 1330                 1335

Ser Ile  Asp Val Phe Asp Val  Arg Arg Ala Glu Trp  Val Gln Thr
    1340                 1345                 1350

Val Pro  Leu Lys Lys Val Arg  Pro Leu Asn Pro Glu  Gly Ser Leu
    1355                 1360                 1365

Phe Leu  Tyr Gly Thr Glu Lys  Val Arg Leu Thr Tyr  Leu Arg Asn
    1370                 1375                 1380

Gln Leu  Ala Glu Lys Asp Glu  Phe Asp Ile Pro Asp  Leu Thr Asp
    1385                 1390                 1395

Asn Ser  Arg Arg Gln Leu Phe  Arg Thr Lys Ser Lys  Arg Arg Phe
    1400                 1405                 1410

Phe Phe  Arg Val Ser Glu Glu  Gln Gln Lys Gln Gln  Arg Arg Glu
    1415                 1420                 1425

Met Leu  Lys Asp Pro Phe Val  Arg Ser Lys Leu Ile  Ser Pro Pro
    1430                 1435                 1440

Thr Asn  Phe Asn His Leu Val  His Val Gly Pro Ala  Asn Gly Arg
    1445                 1450                 1455

Pro Gly  Ala Arg Asp Lys Ser  Pro Pro Pro Trp Ala  Ala Lys Ala
    1460                 1465                 1470

Ser Val  Glu Thr Gln Thr Pro  Val Arg Ala Ala Pro  Gln Pro Pro
    1475                 1480                 1485

Val Cys  His Pro Pro Pro Gln  Val Ser Thr Pro Phe  Gly Ser Leu
    1490                 1495                 1500

Lys Ser  Asp Leu Gly Ile Phe  Val Ser Ser Ser Ala  Ala Gly Ala
    1505                 1510                 1515

Val Lys  Arg Lys Pro Trp Thr  Ser Leu Ser Ser Glu  Ser Val Ser
    1520                 1525                 1530

Cys Pro  Gln Gly Ser Leu Ser  Pro Ala Thr Ser Leu  Met Gln Val
    1535                 1540                 1545

Ser Glu  Arg Pro Arg Ser Leu  Pro Leu Ser Pro Glu  Leu Glu Ser
    1550                 1555                 1560

Ser Pro
    1565
```

<210> SEQ ID NO 3
<211> LENGTH: 20097
<212> TYPE: DNA
<213> ORGANISM: Homo sapiens

<400> SEQUENCE: 3

```
atggagcggc ggctgcgcgc gctggagcag ctggcgcggg gcgaggccgg cggctgcccg      60

gggctcgacg gcctcctaga tctgctgctg gcgctgcacc acgagctcag cagcggcccc     120

ctacggcggg agcgcagcgt ggcgcagttc ctgagctggg gtgagtggcg gggcggcacg     180

gagcgggggc gggcctaggg atatcgcgcc gagacccccg cacccgcaga ctttcccgca     240

gggacccgca cccccacggg cttccctcgc agactccctg cagtggccct gacgcgtacc     300

accggacccc cgcggcccgc acactcgcct gcacacctca ccctcactcc aattctcaca     360

cacgctctct ccctctcaca gaccccgaca catgcacaca cacaccaact tgtgctcagg     420

tatcgaccgc agacgcatgt acccagtgca ccgcctagag tcccttacag atttccttgc     480

ttacaggcca cacctgacgc aggacacaca cagaccctca tgcatgtcac ccactgatac     540

acgggctctg tttctccttc ctctcggatg cattgagaca cacaactcat ggagagaccc     600

agggagcgct gcagaccacc ccgaccgcat tggcactgca aaacacacag atctgtaggt     660

atcgcacact tgcagacctt ccccccacca acacacacac ccccagctcc ctgggtacaa     720

gaccactgca gcctggactc aggaaccgat ctccaaccct tggcctgtgc aggctgctgg     780

ccaagctcct tgggggctgt ggcgccgggg ccggggaggg gggcctagct ggagatgggt     840

ctgtaccttt cctggtagac tcatctgagt cattgggagt ggctggcccg gggtgaccct     900

gaacccactg tgggcactgg cgccagctgg agggttccct ggtcacaccc tgccgggcca     960

tggggaaaag gcacgggggc ctggccaggg cggggtgagg caggtgtttg cccagtgggc    1020

aactagcgtt cctggcactc ctgagctctg ggaaggcaca aggcctgggg tagaggggga    1080

ggctgccacc tagatgtgcc agggagttgt cccctagccc caacccttcc atccagggcg    1140

aggcagtcag aggcccctgc ctctgtgcct gtctccctgg tatgcctccg tgctatgcct    1200

gtctgcctgt gttgttgtca ccccccccat gacacccaca cacgtgtgtg tgtttgcaca    1260

cacatgtgtg ctcctccctg actgcctcca gcacctctgc ctgggacccc ggcatggggg    1320

ccctctgttg acaatctccc aaggtaactc aaagggctgt gactcattcc tctcctgctt    1380

gtctctactt gtccctgctc ctgcccggag cccccatgcc ctgtgggagg ccagaggatt    1440

aggcagcctg tccaggggcc tggatcctcc tgcctgtggg cctgggcttc ggccctcttc    1500

tggcgggtgg gtccctatgg tgctggcttc aactcccacg gggaggcccg gggctgctcc    1560

tccccagctc cacacacaga cctgggaaag agacaatgaa tttctgtaat gaggtttcca    1620

ccccgccccc gctgcgggct tctgcctgat aaacctgtgg aacagctctc tgtcccaccc    1680

acagacccgc ccagctggca gggagtttac ctcctggcag gggggaaactg aggcagggcg    1740

ccagaccaca gctgcccccc atcctgactg atcactcctg cctccctaag acccaattcc    1800

ttcccaaaac ctggggctaa tccaggcctg gaaagtgcct gggagtggct ggagttgccc    1860

ttcctggagg tatctgggat gtgaggaaag aggacgttct tgaccagaca aaagcttcgt    1920

ccagacaggg aggcagggct gggagtgaga gagccggtca ggcctggagg catcctgagc    1980

actcacgcct tcaggggcta gtgctagcac cagggaaagg catctttgtc ctgtttgtga    2040

gtctcagcac cttggcagac tggcatccat gcctccagcc tgaggggccc cacgtgggaa    2100

gcatagagcc tgtcctccct gccctagggg ctgcaggcct cacccccaac caggcacctc    2160
```

```
tatgcctaca gggtcccggg acccaggccc acagctcctg aatgggagag aagcctctct   2220
ggggataagg aatgtcaccc gtccagtttc ctaagacagg ccctggcctg aacctgtgag   2280
ggggccaaga actgtgaggt gggggtagga atggtgtccc catggtcccc agggtgacct   2340
ggccaagcag agtcaggccg cagactgggc aggactacaa gtcccatcag cccctgggat   2400
ggaggctgcc tagagtctgg ggccaggggt ccagggaggt ccagggacca ggcggtcagc   2460
tgagcccggc ctctgacctt ccgcacttcc tgatcatggc caaaggagca ccagttcctg   2520
ccacaacccc ttggcccgag gctgtccctg ggaggtcat ccctgcctgg gctcacagga    2580
gcggcagctc ctggcttgcc caaggtgaga gggggaatgg agccctccct ccctgcactc   2640
tgagtcccgc cctgtgtccc ctcagccagc cccttcgtat caaaggtgaa agaactgcgt   2700
ctgcagagag atgactttga gatcttgaag gtgatcggcc gaggagcctt tggggaggtg   2760
agcaaagggc ctggggtagg tgggggggagg tgttcacacc gggctgggct caccccggtc  2820
ctccctgtgg ccttaggtca ccgtggtgag gcagagggac actgggcaga tttttgccat   2880
gaaaatgctg cacaagtggg agatgctgaa gagggctgag gtcagtgtgg agtctggggg   2940
gcccttgggc accctacaaa tgggtgtggg ggaggtgtat gctgccaggg cctatggcgc   3000
gggggggcg ggcaaggctg cagaccaggc aaagggtgcc accctcagca gccactgatt    3060
tgttatcttt ctcacaataa accctttatt taattttttta aatttttttt ttttttttga  3120
gacggaatct tgctctgtca actaggctgg agttcaacgg tgctatcttg gctcactgca   3180
acctccgcct cccagttcaa gtaattctcc tgcctcagcc tcccgagtag ctgggattac   3240
aggcacctgc caccacaccc agctaatttt tgtattttta gtagagatga ggttttgcta   3300
tgttggacag gctggtctcg aactcctgac ctcagatgat ccttctgcct tggcctcccg   3360
aagtgctggg attacaggcg tgaaccaccg tgcccagcct acaataaact tttttttta    3420
agatagagtc tcactctgtc acccaggctg gagtgcggtg gcgtgatctc ggctcactgc   3480
aacctccacc tcctgggtgc aagggattct catgcctcag cctcccaagt agctgggatt   3540
acaggcgtgt gccacgacac ccagctaagt ttcttgtatt tttagtagag atggagtttc   3600
accacattgg ccaggctggt ctccaactct tgatctcaag tgatctgcct gccttggcct   3660
cccaaagtgc tgggattaca ggcctaataa accctttga aagcaagcag agtcgttccc    3720
attttccata tggtcacact gaggcccaga gctgtagagc gtgggcttgg gctcagtcgc   3780
agccagacag gggacagtag agctatgacc tccatctgag ctcccagact cacagaatct   3840
ttctccatcc cctgagctgg caagggggca tcctgggctc tgatcccacc ccacccctta   3900
cttccccaaa cctgctgcag acagcctgtt tccgggagga gcgggatgtg ctcgtgaaag   3960
gggacagccg ttgggtgacc actctgcact atgccttcca agacgaggag tacctggtga   4020
ggatacgtgg cggggctgga ggggaacatc ctagggacac aggagagggc ccttggggcc   4080
aggggcactg ggcccaaaga gagacccctc ttgggaccaa gagactccca cttcccacca   4140
gttcctgggc ttggcgcctc ctgcctgagc cctggctggg aactggccag cccagagctg   4200
ctgggagatg caggcctgcc ttcccagagc cctgcgggac cgcggtgaag tggccaggtg   4260
cacccttccc ccgggtctga ttcttgtccg ccacctccag taccttgtga tggactacta   4320
tgctggtggg gacctcctga cgctgctgag ccgcttcgag gaccgtctcc cgccccgagct  4380
ggcccagttc tacctggctg agatggtgct ggccatccac tcgctgcacc agctgggtta   4440
tgtccacagg tggagcccca accccgctgc cctgcccaac cccgctgccc tgcccaaccc   4500
ctgccagctg tgctggggac agctgatgtc agctgagcac tcatcatgtg ccaggcactt   4560
```

```
ctctgggtgc ctcatccgtg tgcttccttg gaatcatacc aaagagccct ctgtggcagg   4620
ggctgctgct gtgtccggcc tgcagctgag ggggtcagag cttagcacag ggaaacacct   4680
gtctcaaggt gactcggctc tcgggtggca agctgtggtc tgcactgggg aagtctgact   4740
cctgcgtccc ccatagcaca ctctgccacc tccaagggtt gtccccacac atcctttcta   4800
caatctagcc atcttcctcc ttctggcctg tgggatcatc tacacacaca cacgttgctc   4860
atcacatgag cacctacaca caggaatgtg tgtgagctgg tgctggcaca caccgtgcat   4920
gtgcacctgg gcgtgtgcct aaatggccac ttacacacag gtcaaacgcc tcactctccc   4980
tgcctgccat cccccaggga tgtcaagcca gacaacgtcc tgctggatgt gaacgggcac   5040
attcgcctgg ctgacttcgg ctcctgcctg cgtctcaaca ccaacggcat ggtaaggacc   5100
ccgccccaga gtgggagcag gggatacaag gcgggccaag ctctcaggaa aatgggaggc   5160
cccaggccta gtgcagaggc atcaggcccc ccggggaagg tgggtgagac ccaggcccca   5220
ggtgggcagc agcaggccag cctggcagag taggggtgac agggccatcg cgaggggcca   5280
gcagtcccag ccaagcccaa agctgtcctc atggcttcac caccaccacc cacaggtgga   5340
ttcatcagtg gcagtaggga cgccggacta tatctcccct gagatcctgc aggccatgga   5400
ggagggcaag ggccactacg gcccacagtg tgactggtgg tcgcttggag tctgcgccta   5460
tgagctgctc tttggggaga cgcccttcta tgctgagtcc ttggtggaaa cctacggcaa   5520
gatcatgaac cacgaggtct ggacaccagg ctctgggctt ccagaggggg cagtgggacc   5580
cctgagtctg tgtggttgga agtaccggca ggtgaggctg ggttcctgga cacttgaccc   5640
agcgtgcccc ctcccccgac ccacaggacc acctgcagtt ccccccggac gtgcctgacg   5700
tgccagccag cgcccaagac ctgatccgcc agctgctgtg tcgccaggaa gagcggctag   5760
gccgtggtgg gctggatgac ttccggaacc atcctttctt cgaaggcgtg gactgggagc   5820
ggctggcgag cagcacggcc ccctatattc ctgagctgcg gggacccatg gacacctcca   5880
actttgatgt ggatgacgac accctcaacc atccagtgag tggcaaaggc cactgcagga   5940
ggggagctgc cctacccccct tgttggctgg gggaaccctc cctctgaagt cccctggggt   6000
gggctggggg tgaggccttc agacaccggg gcttatgatt tatggactcc cagactgacc   6060
cgttccagcc accatccgct ggcccagcct cttccagcca aactggggtg ggggagcatc   6120
tcccacaggc tccccatgct tgcctgcact gaggtgggct gtgtcaaggg aagggcctct   6180
gaccacaggt atcattctat taactagaat ccgtataagg aagaaaactc ccagcagctc   6240
ctaggagact tgtgggagct gggggtttgt ttgggttggg ctgtgttacc cccctgagtt   6300
cccacctgtg caggaggtgg tcgcacctgg tcccaggggg ctcctgggcc tcgggcctcg   6360
ggccttggcc tgtggactct gactctcctt ccctctccct ctgcagggga ccctgccacc   6420
gccctcccac ggggccttct ccggccatca cctgccattc gtgggcttca cctacacctc   6480
aggcaggtga ggctagtcct cacacacctg gtgggaggct cggggttgcc tgacctggag   6540
gacactgggc gcgtagccca ctggggccct gggaaggagg gcagaagggc tccccagtat   6600
ctgcatgtgg caggtgctct agccctcatc ctcggggtcc tggtgaagcc acacccaggt   6660
cctgctgggc cacatgccag cacatggctc tcatggcgcc ttccacgaag gtcgagggtg   6720
cgctgcacct agagccagag gtgcagggtt cgaaggcccc tactgctccc aggcctcact   6780
ttgtggctct gtaaaatggg tgggatggac caggcgtggt ggcttatggt tgtaatccca   6840
gcacttaggg aggtcgaggc gggtggatcg cctgaggtca ggagttcgag accagcctgg   6900
ccaacatagt gaaaccccat ctctactaaa aatacaaaaa ttagccgggc gtggtggcgg   6960
```

```
gcgcctgtaa tcccagctac ttgggaggct gaggcagcga gaatcgcttg aacgcgggag   7020
gcggaggttg cagtgagctg agattgcgcc actgcactcc agcctgggtg acagagcgac   7080
tctgtctcaa aatgggtggg attatctcca cctactccca ttcgaggggc tggcctgaga   7140
ccgcagtgag gtcctggtgc ggtgtgctct gaggtggaag gaaatgggtc agatccccac   7200
tcctctagac cagccgggcc actgtcacca catcctgtcc tcgacagccc tggggagagg   7260
ccttgtcacc accatcttcc cctggggaaa ctgagggtaa aatacattgg gttcgaggtg   7320
atacagcttg taagggccag gatgagggtt taaacctggg cctggacccg gagcctgtgc   7380
cctgcagctg ctaccccggg ctgccacccg tggcaccagt ctggggtctc ccgagggcag   7440
ggtctgtttt ggctgtttca caattaatga gtgattcggt ccaggaggat ggaggagact   7500
ctgtggggtg aggtttctac caacaaacat ggcccctgtc cccctacagt cacagtcctg   7560
agagcagctc tgaggcttgg gctgccctgg agcggaagct ccagtgtctg gagcaggaga   7620
aggtggagct gagcaggaag caccaaggta ctgggagcgg ctgggccggg cctgggtgtg   7680
ctggccctag ggctgctgc tgcgggaatg gaggagtgga ctcacctgtg ggtaccacct   7740
cccctccaga ggccctgcac gcccccacag accatcggga gctggagcag ctacggaagg   7800
aagtgcagac tctgcgggac aggctgccag gtatcccttc cgcccacccc ccccccccc   7860
cccccggggc tgagtcccac ctgggctcgg gtcctgccct gccctggaca agctgtatga   7920
tcctgggaga gcattttata ctctctgagc ccgcgtgtgg gaaacaggcc aaggagactt   7980
gctcctgggc tgagaggctg gggccgccag cactcgaggt ctcagtgact cttcctggca   8040
gagatgctga gggacaaggc ctcattgtcc cagacggatg ggcccccagc tggtagccca   8100
ggtcaggaca gtgacctacg gcaggagctt gaccgacttc accgggtgag ggctgggtga   8160
ggtgggtgag ggctgggtga ggtgggtgag gtgggtgagt ggccctgggc tccatggacg   8220
gttcgtgcct gactctgggc cttgtccttc cccgctccct cccctgcctc ctcaggagct   8280
ggccgagggt cgggcagggc tgcaggctca ggagcaggag ctctgcaggg cccaggggca   8340
gcaggaggag ctgcttcaga ggctacagga ggcccaggag agagaggcgg ccacagctag   8400
ccagacccgg gccctgagct cccagctgga ggaagcccgg gctgcccaga gggaggtgag   8460
tgaccagggt gggtagggac agcacctggg ccctgccccc agtgtgcctg gagggagcat   8520
ggggagcttg gtgggagatg ctgcctcccg gttgtagctg gcagaggcta ggccagggga   8580
tggtggctgg gacggggcag tctgggagtc catgcctcct catgtccact gtggctggca   8640
ggtctggagt ccatggtaag gtgggcagag gggctgccga gggcagagtt ggcagtggcc   8700
tgcctctgca cccctcacag ctggaggccc aggtgtcctc cctgagccgg caggtgacgc   8760
agctgcaggg acagtgggag caacgccttg aggagtcgtc ccaggccaag gtagtcaagt   8820
cctccccctt ggcaagaggt gcttccccac cagcctgacc ccactcagag cctcagggcc   8880
aggcctgtgt cccaggtggg tggccatggg catcttgggt ctctgccctg accccctcca   8940
tgtccccaag accatccaca cagcctctga gaccaacggg atgggacccc ctgagggtgg   9000
gcctcaggag gcccaactga ggaaggaggt ggccgccctg cgagagcagc tggagcaggc   9060
ccacagccac aggtgagcca ggcagctggt ggcagggagg ggccgggcct ggcctgggcg   9120
gtgagtcacg gccttggcct tctcctcccc aggccgagtg gtaaggagga ggctctgtgc   9180
cagctgcagg aggaaaaccg gaggctgagc cgggagcagg agcgggtgag cagggtacaa   9240
cagacggagg gtacaacaga cggacaaggc aatggggagc cagttggggg gtgggcaagc   9300
tgcagccagt gagcagggtg gacatggacg gggctcgggg tgctggggta cctacaggga   9360
```

```
gacggcagtc ccaggactgc tggggcctgg ggctgacctt tcctctggcc ggccccagct   9420
agaagcagag ctggcccagg agcaggagag caagcagcgg ctggagggtg agcggcggga   9480
gacggagagc aactgggagg cccagctcgc cgacatcctc agctggtggg tgccaggggt   9540
gggtcggggt ggggaacgca ggcgagactg agggcccagc ccatgaccct gagccccttc   9600
ccattcaggg tgaatgatga gaaggtctca agaggctacc tgcaggccct ggccaccaag   9660
atggcagagg agctggagtc cttgaggaac gtaggcaccc agacgctccc tgcccggcca   9720
ctggtgagcc ccagagatgc ccctggggc tggcttgggc aagtcactga ccttccgtga   9780
gctcagcatc cctgctactg aaggtcacta ctggaggtgg ggacaccaag ctcatgagag   9840
atagtgattt ccctgagctc acagtgggtc attggctgag ctggagcttt gagcctggct   9900
gggtggcatg ggtagcagga tgctctggta gcagggggtc cctgaggcag ccaggcctag   9960
aaagcatctt atacgggtgc tccgtggcca ccaggaccac cagtggaagg cgcggcgact  10020
gcagaagatg gaggcctcgg ccaggctgga gctgcagtca gcgctggagg ccgagatccg  10080
cgccaagcag ggcctgcagg agcggctgac acaggtgcag gaggcccagc tgcaggctga  10140
gcggtgaggc taggggcagg cactggggc cagggcccgc acagaggcca gtggcgagcc  10200
cttgccattc tccccagccg tctgcaggag gccgagaagc agagccaggc cctgcaacag  10260
gagctcgcca tgctgcggga ggagctgcgg gcccgagggc cagtgggtga gtggctgcca  10320
actgcttgcc ccggagccag gctcccccgc ggcctcccac ttgccaaggg ggctccacga  10380
tggcctggca gggtggtgga gacaggagtc tgttcctgga ctctgccgct tactccatca  10440
tctgtgacca gcacttctgg agtgcctgct gtgcccagcc ctgccccacc ctgtggtcat  10500
ttcccatttt actgaggtgg gaactgaggc cctcctgga ccctagttcc tcaggccagg  10560
gaccccaggc cagtgaccca ccctttcttt gcagacacca agccctcaaa ctccctgatt  10620
cccttcctgt ccttccggag ctcagaggta aggaccaggc caaggggctt gttggggaga  10680
agttctggga gaggcacagg gaccttgact ttgctcctct ctctcccacc cccagaagga  10740
ttctgccaag gaccctggca tctcaggaga ggccacaagg catggaggag agccagatct  10800
gaggccggag ggccgacgca gcctgcgcat gggggtgagg acaggtgggt ccatcgtagg  10860
gggcctgggc cccgcccttg cccgtctcac ctgctccccc gccctcctgc aggctgtgtt  10920
ccccagagca cccactgcca acacagcctc tacagaaggt cttcctgcta aggtcagtgc  10980
ccagaggggc aagcagggtg gggcaccaa gcagttctgc caggctgaat gggcactgtg  11040
gggacactcc acgtgcatcg tggctagcag gcacaattgg ggtggaggtg gtggcgatga  11100
gcttgcctgc cgccatagat tggctgggac tcggaggtca ctgttgcctg gctcagcccc  11160
ttgtctttcc tgacccctca gggatggggc atggggccct gggaggcctt gggtaatggc  11220
tgtccccctc cccagcccgg ctcacacacg ctgcgccccc ggagcttccc atccccgacc  11280
aagtgtctcc gctgcacctc gctgatgctg ggcctgggcc gccagggcct gggttgtgat  11340
ggtgagagtc cccacccact atgctccagc cacggtccca ggtgtgtggc cctggcatac  11400
ccaggctgtt tctcccatcc cagggtcact ggcacctgct ggtcaaattt cctcctgctc  11460
agctttgttc cttttctcac ttgatgagga attggggaca gttcgggtgc caccgtggct  11520
tcagggaagc tggctctgga catgccccg tcctggtttg ggctgtccc ctcccagcct  11580
cacctcatcc accttctcca ctttccccac agcctgcggc tacttttgtc acacaacctg  11640
tgccccacag gccccaccct gccccgtgcc ccctgacctc ctccgcacag ccctgggagt  11700
acaccccgaa acaggcacag gcactgccta tgagggcttt ctgtcggtga gtgggggccg  11760
```

```
agggagggga agatgggcat ggggggctga gggtccctgc agccctccca tgcttgcctt  11820
tccgccaggt gccgcggccc tcaggtgtcc ggcggggctg gcagcgcgtg tttgctgccc  11880
tgagtgactc acgcctgctg ctgtttgacg cccctgacct gaggctcagc ccgcccagtg  11940
gggccctcct gcaggtccta gatctgaggt aggtgccggg cagtggcatg gggcaaggga  12000
ctagtggtaa ggggggcagt cagggacagg gagatttctg aactgttctg tgaacctccc  12060
agggaccccc agttctcggc taccccctgtc ctggcctctg atgttatcca tgcccaatcc  12120
agggacctgc cacgcatctt tagggtgagt gcctgggatg agatggagca gccaccatcc  12180
acctccccat gctgtcccag ctctggccac tgtcccccca cttcatactg ccctcttggg  12240
ccagcccaca accacagcac gctttccacg tgagcacctg gcccggtctc acctcgttta  12300
ggatctgctg tggcttccca tcgtctgcgg ggctcggggt gctcctgacc tagcccttga  12360
ggccccaagg ctctgaccct gcaggcctcc cagccctctc ccttggcacc tgtctctgct  12420
ctggtcacac cttgctctct ccagttctga aggcgccctg tgcctgtgtg caccacattc  12480
tcagtccttc acatctgtct ttgcacgaaa ttgccggccc tgcactggag cccagcccct  12540
cacctacctt gactactcct ggttagttac tcgtccctca ggcttcagca gaaatgtctg  12600
gtctcctggg aagtcatcct tcacctcccg gccccggttt gggtccctct gtgttcccac  12660
taggcccgtc cttgccccat tatggcgctg gtcgcatggc tctggagttg tctgtttgcc  12720
tgtctggcct actccctgct gctgacagtg cacgctaggc ccccggggca cagcggctgc  12780
tggaggcagg aagggaggga ggacagatgg ctctggtcca cggccctcca gctggggtcc  12840
ttgcccacag gtgacaacct cccagctggc agtgccgccc accacgtgca ctgtgctgct  12900
gctggcagag agcgaggggg agcgggaacg ctggctgcag gtgctgggtg agctgcagcg  12960
gctgctgctg gacgcgcggc caagaccccg gcccgtgtac acactcaagg aggcttacga  13020
caacgggctg ccgctgctgc ctcacacgct ctgcgctgcc atcctcggtg agctggtgga  13080
ggggactgga ggaagcagtc caggcctgcg ggagtgctgg tgtctaggaa tagtcccaag  13140
ggccactgct actgcccatt ccctgcagcc acgagacaca gactgccttg caccacgtat  13200
gtgctccagc ctcctgtgtg catggctggg cccccaggta gggggcctgg cttatcccca  13260
ctccatttcg ctgtgcctca gtttctgctt tttccaaaag aatctcaagc aagtggaagg  13320
aacaaaggct tttttttttt tctttttctt tttttgagac agagtctcgc tcggtcgccc  13380
aggctggagc tcagcagtgc aatctcagct cactgcaacc tccacctccc agattcaagc  13440
gattctcctg tctcagcctc cagagtagct gggattgcag gcatgcacca cctcgcctgg  13500
ctattttttg tatttttagt agagacgggg tttcagcatg ttggccaggc tggtctcgaa  13560
ctcctgacct caggtgatcc acccaccttg gcctcccaaa gtgctggaat tataggcatg  13620
ggccaccgtg cccagctgga acaaaggctt tagaaagaga gaaacgaagg ttcagtcctg  13680
gctgtctcac tacaagctgg gggactgggg gagctgctgt agaaccaccc agagcctcat  13740
aacatctcct gggtggagct gcgaagagct tcacttgtgc tcagccttga acctggggct  13800
cagcagggct cttctgtaac taaggctggg aaagaggcat gaaacagagc tccttggcgt  13860
tccccagcag ctgaggccct gagccaggcc cggctctcag ggcgggagac acaggagagg  13920
ttgtgcgggt ccctggagca gtcgggaacc agaggggagg ggatttattg agcaaggggc  13980
tctgctgaac cctcccctgc atcacttcct cgcttcctca gagttgctct gtgaggaagt  14040
accatcgttg tccccagttt acataaggaa accaaggctc tgagaggtga catgacttac  14100
ccaaaatccc acagctcaag atgatgggcc tcaccccaac ccctctggaa aagcctgtcc  14160
```

```
agactgggag agaagggtca gtgaggcagg gacagcggga ttattgccac ccccatttcc  14220
tcaagataaa caggcacagc agggcaggtg gactgcccaa tctccgtgtc attgagtggg  14280
actgctgacc tctgaccctc tgcctccctc taccagacca ggatcgactt gcgcttggca  14340
ccgaggaggg gctctttgtc atccatctgc gcagcaacgg tacctatcaa agctgggcta  14400
gggtgggcgt gggcaggggc agccccagcg ggcagaggag gatggggatg ggtcactctt  14460
caaccacctg ccagtgacac tctcccctcg ccaaccctgc agacatcttc caggtggggg  14520
agtgccggcg cgtgcagcag ctgaccttga gccccagtgc aggcctgctg gtcgtgctgt  14580
gtggccgcgg ccccagcgtg cgtctctttg ccctggcgga gctggagaac atagaggtag  14640
caggtgccaa gatccccgag tctcgaggct gccaggtgct ggcagctgga agcatcctgc  14700
aggcccgcac cccggtgctc tgtgtagccg tcaagcgcca ggtgctctgc taccagctgg  14760
gcccgggccc tgggccctgg cagcgccgca tccgtgagct gcaggcacct gccactgtgc  14820
agagcctggg gctgctgggc gaccggctat gtgtgggcgc cgccggtggc tttgcactct  14880
acccgctgct caacgaggct gcgccgttgg cgctgggggc cggtttggtg cctgaggagc  14940
tgccaccatc ccgcgggggc ctgggtgagg cactgggtgc cgtggagctt agcctcagcg  15000
agttcctgct actcttcacc actgctggca tctacgtgga tggcgcaggc cgcaagtctc  15060
gtggccacga gctgttgtgg ccagcagcgc ccatgggctg ggtaaggcc tgctgagggc  15120
ttggcagggg ggccaggcac cttcagtggg tgggtgaaga cagggtcccg cctcaactca  15180
tgagcctggc attggaggcc tttggtgcca gtttgcatcc tccagcccaa caacaccctg  15240
tcccaccctc tgtggcttgc aggggacctt ccttttccat ggctgagctc atgctcctct  15300
cctgcctgag ccgctctcct tttgtttcta tctagcaaac tttttttttc ttttgagaca  15360
gggtctctgt ctgtcaccag gctggagtac agtggcacaa tctcgactca ctgccacctc  15420
cgcctcctgg ggtcaagtga tcctcccacc tcaccctctc gagtaactgg gggcacaggt  15480
gtgtgccatc acgcctggct aatttttgtt ttgttttgtt tgagacagag gagtctcact  15540
ctgtcgccag gctggagtgc agtggtgtga tctcggctca ctgcaacctt tgcttcccgg  15600
gttcaggtga ttctcctgcc tcagcctccc tagtagctgg gactacaggt gcacgccacc  15660
acacccagct aatttttgta tttttagtgg agacggggtt tcaccatgtt ggccaggctg  15720
gtctcaaact cctgaccaag tgatccacct gccttggcct cccaaagtgc tgggattaca  15780
ggcgttagcc aacgcgtcca gcctaatttt tgtatttttt cagagatggg gtttcgccat  15840
attgcgcagg ctgggagtct caaactcctg aactcaagca atcctcccgc gcggcctccc  15900
aaagtgctgg gattacaggt gtgagccacc ggccccggcc tgtacctggc aaactcttaa  15960
ctaggtacca ccccagtgtc agctcagggc ctggagctgg taggcgctcc aaagataacc  16020
gctgcgattg ctgtggtcac cattgccttc gtgctccccg ccctgcttcc ccgtcattgg  16080
tcctttcctt ctctttgccc cactatctct ccgtccagac ctgtgtcacg gctctcatcg  16140
cctccacttc atgactggct tggtgcactg gggtcccaca gaatgggccg gggctggttt  16200
cctcatccac atcaagcccc cagcccaggg tggcacactc caggggcgat gggcttggag  16260
gaatgagtgg aagagtgaat gaatgaatga ggcagtgggg cagtctggtg catgcacaag  16320
taactagcat gatgggtaag ggctggaaga gaggggcaga gtgtccttcg tgagcaatgg  16380
ctctttgggg tggggcctgc aggttgggtg ccgcatatca cccaagctgc ccagggccaa  16440
atcgcagctc tcaggaccag ctgagtgacc tgaccttgac catcacatgg ctccaggggt  16500
tccattccct catctggaaa ttagggatta taacagtagt acttgctcag agttgttaga  16560
```

```
aaattaaggc aggaaaagca tgtcgtgttt agaactgagc caggcatgtg gtgagtggtc  16620
cagggttatc tctgatttga tgtggaggct gggccgggcg acagggagtc ttcagaggaa  16680
ggaccttagc gtggggcatg gtagttactg tgctgtggca ggggacaagg tgttccctgt  16740
ggaacagagg gggaaacagc tcagaggtgc ctggcgtgcc cgcagggtat gcggcccccct  16800
acctgacagt gttcagcgag aactccatcg atgtgtttga cgtgaggagg gcagaatggg  16860
tgcagaccgt gccgctcaag aaggtgaggg tccgccagag ccctggggta gcgccggggg  16920
tggaggcgtg gcctgaccgc tgtgcctgct gcctcaggtg cggcccctca atccagaggg  16980
ctccctgttc ctctacggca ccgagaaggt ccgcctgacc tacctcagga accagctggc  17040
aggtgaggga gtgcgtgtgt acgggtgtgt gcgttcccca gtgcgcacgt gtggctgtgt  17100
ggccctgaat gccagctgac tgggccccgg gaatgtgtga gcacagccca gctctccact  17160
tctcccacag agaaggacga gttcgacatc ccggacctca ccgacaacag ccggcgccag  17220
ctgttccgca ccaagagcaa gcgccgcttc tttttccgcg tgtcggagga gcagcagaag  17280
cagcagcgca ggtgcgcgtg cacgacgcgg gggctgaggc tgggtggggc cgcctccgct  17340
tgtggacggg tcgaagggag ggtggagctt cgccacccac tacttacacc tccgcccaca  17400
gggagatgct gaaggaccct tttgtgcgct ccaagctcat ctcgccgcct accaacttca  17460
accacctagt acacgtgggc cctgccaacg ggcggcccgg cgccagggac aagtccccgg  17520
ttagtcctct ggagccaatc acaagccact ctggtgaggc tgagccaata accggcctct  17580
gtggtgagct ctagccaatc acgggccgct gtaattactc ctaaggcctg ggactcacac  17640
ttctgctccc tgggacttaa gtaaaaccag gctgggggcc cagtggcgtt catttgtcct  17700
ggtctgttgt gccttgggcc tcttgtcctc cttgtgcctg ctagtcccag cccctccgca  17760
ctgtcaccca acaggctccc gaagagaagg gccgagttgc ccgcggctcc ggcccacagc  17820
ggccccacag cttctccgag gcgttgcggc gcccagcctc catgggcagc gaaggcctcg  17880
gtggagacgc agaccccagt aagggcagcc cctcagcctc cagtgtgcca ccccccaccc  17940
caagtttcta ccccctttgg atccctgaaa tctgatcttg gtatttttgt ctcctcgtct  18000
gctgctggag cagtgaagag gaaaccctgg acatccctgt ccagcgagtc tgtgtcctgc  18060
ccccagggat cgctgagccc tgcaacctcc ctaatgcagg tgagcgggtc cgggaggctt  18120
gtccgtcccc tattcaaacg tcaggcagtt ccgttttatg ctaggccttg cacagtgacc  18180
taggctaggg aacaagctga gcccatccct gccctcgatt ctacgagatg cagattctta  18240
cctgtctcac cccaccagtg ggcaccagca ggatcctgga tgcaggccag cctaggtggg  18300
aatcttggct ctgactgttc cagctgtgtg gctctgggca aaatgcccaa cctccctgat  18360
cttgtcttac ctgtaaaatg atgtggtttc tgggaggcct gcatgagctg atgatacctg  18420
cgaagggctc agcatagtac ctggcatggg gaaggtgcca cagaagggga gctcttggga  18480
ttcttttttt tttttttttt ttccagacgg agtctcactc tgtcacccag actggagtgc  18540
agtggcacaa tctcggtcag tgcaaccccc acctcccaca tttgagcaag tctcctacct  18600
cagcctctcc caagtcgctg gtattacagg catgcatcac catgcccagc taattcttgt  18660
attttaagta gagatggggt ttcattatgt tggccaggct ggtctcgaac tcctgacctc  18720
aagtgatccg cccaccttgg cctcccaaag tgttgggatt actgatgtga gccaccatgc  18780
ccggccactc ttgggattct taatagaggc ccagtccaca gcagggagtt ggggggtcag  18840
aggagggagc agtccattct gaatgagggc aggggaaaac ctaagagaag ccagggaggt  18900
tcccattccc cctgcagcca cgtctacagc acacacatcc acccactccc gtcacaccag  18960
```

```
gccacttgga gccctggggc ttgccatgtt cttccacacc tgcaggctct tgcccctgca  19020

gtcccctctg ttttgaatgc cttttctcta tcttcacctt aaccaacatc agactgccct  19080

ccaggtgacc caccaggatc atcttcaaag gagccttcct ggccgcttgg tcaggtagtc  19140

attgcctccc tggggctggt gccacctttg ccaccccgct ccctccacac cttccttgca  19200

gcttctgctg tgctgtgggt ttcttctggt gcctgttctc ctctgttgac tgtgggctcc  19260

ttggtggtgg gggtcaggct tcattcttct gcccagagta aagcatgtgg tcgactgaag  19320

gaagaatgga gtgaatgaac aaagggactt tgaggctggg cgctgtggct cacccctgta  19380

atcgcagcac tttgggaggc tgaggcaggc agatcacttg aggtcaagag ttcaagacca  19440

gcctggccaa catggtgaaa ccctgtctct actaaaaata caaaaattag ctgggcctgg  19500

tggtgcatgc ttgtaatccc agctacctgg tgggccgagg caggagaatc acttgaacct  19560

gggaggcgga ggttgcagtg agccaagatc atgccactgc attccagcct ccagagcgag  19620

actctgtctc caaaaaaaaa aacgaaaaac aaaaattaac taggcatggt ggtgcatgcc  19680

tgtcatccca gctacctggg aggcagaggc aggagaatca ctagaacctg ggaggcagag  19740

gttgcagtga gccaagatca tgccattatt gcactccagg ctaggcgaca gagcaagact  19800

ctgtctcaga aaaaaagaaa aaaaaaagga ctttgagtcc attcaaagtt aagtaggagc  19860

tctccaggtt cttccagtga cccatttacc acctctactc ctcacctcac atctggcttc  19920

ctccaggggc cctgatacag tgggtgatgg gtcctaaggg ggcctccagg acccaccagc  19980

cctatgagga aagagttctt cctgatccta ccccttgact tccttttctt tctcctgcag  20040

gtctcagaac ggccccgaag cctcccccta tcccctgaat tggagagctc tccttga     20097
```

<210> SEQ ID NO 4
<211> LENGTH: 1572
<212> TYPE: PRT
<213> ORGANISM: Homo sapiens

<400> SEQUENCE: 4

```
Met Glu Arg Arg Leu Arg Ala Leu Glu Gln Leu Ala Arg Gly Glu Ala
1               5                   10                  15

Gly Gly Cys Pro Gly Leu Asp Gly Leu Leu Asp Leu Leu Leu Ala Leu
            20                  25                  30

His His Glu Leu Ser Ser Gly Pro Leu Arg Arg Glu Arg Ser Val Ala
        35                  40                  45

Gln Phe Leu Ser Trp Ala Ser Pro Phe Val Ser Lys Val Lys Glu Leu
    50                  55                  60

Arg Leu Gln Arg Asp Asp Phe Glu Ile Leu Lys Val Ile Gly Arg Gly
65                  70                  75                  80

Ala Phe Gly Glu Val Thr Val Val Arg Gln Arg Asp Thr Gly Gln Ile
                85                  90                  95

Phe Ala Met Lys Met Leu His Lys Trp Glu Met Leu Lys Arg Ala Gly
            100                 105                 110

Ala Ala Cys Phe Arg Glu Glu Arg Asp Val Leu Val Lys Val Asn Ser
        115                 120                 125

Arg Trp Val Thr Thr Leu His Tyr Ala Phe Gln Asp Glu Glu Tyr Leu
    130                 135                 140

Tyr Leu Val Met Asp Tyr Tyr Ala Gly Gly Asp Leu Leu Thr Leu Leu
145                 150                 155                 160

Ser Arg Phe Glu Asp Arg Leu Pro Pro Glu Leu Ala Gln Phe Tyr Leu
                165                 170                 175
```

```
Ala Glu Met Val Leu Ala Ile His Ser Leu His Gln Leu Gly Tyr Val
            180                 185                 190

His Arg Asp Cys Lys Pro Asp Asn Val Leu Leu Asp Val Asn Gly His
        195                 200                 205

Ile Arg Leu Ala Asp Phe Gly Ser Cys Leu Arg Leu Asn Thr Asn Gly
    210                 215                 220

Leu Ala Asp Ser Ser Val Ala Val Gly Thr Pro Asp Tyr Ile Ser Pro
225                 230                 235                 240

Glu Ile Leu Gln Val Leu Glu Glu Gly Lys Gly His Tyr Gly Pro Gln
                245                 250                 255

Cys Ile Trp Arg Ser Leu Gly Val Cys Ala Tyr Glu Leu Leu Phe Gly
            260                 265                 270

Glu Thr Pro Phe Tyr Ala Glu Ser Leu Val Glu Thr Tyr Gly Lys Ile
        275                 280                 285

Met Asn His Glu Asp His Leu Gln Phe Pro Pro Asp Val Pro Asp Val
    290                 295                 300

Pro Ala Ser Ala Gln Asp Leu Ile Arg Gln Leu Leu Cys Arg Gln Glu
305                 310                 315                 320

Glu Arg Leu Gly Arg Val Gly Leu Asp Asp Phe Arg Asn His Pro Phe
                325                 330                 335

Phe Glu Gly Val Asp Trp Glu Arg Leu Ala Ser Ser Ser Ala Pro Tyr
            340                 345                 350

Ile Pro Glu Leu Arg Gly Pro Gly Asp Thr Ser Asn Phe Asp Val Asp
        355                 360                 365

Asp Asp Thr Leu Asn His Pro Gly Thr Leu Pro Arg Pro Ser His Gly
    370                 375                 380

Ala Phe Ser Gly His His Leu Pro Phe Val Gly Phe Thr Tyr Thr Ser
385                 390                 395                 400

Gly Ser His Ser Pro Glu Ser Ser Ser Glu Ala Trp Ala Ala Leu Glu
                405                 410                 415

Arg Lys Leu Gln Cys Leu Glu Gln Glu Lys Val Glu Leu Ser Arg Lys
            420                 425                 430

His Gln Glu Ala Leu His Ala Pro Thr Asp His Arg Glu Leu Glu Gln
        435                 440                 445

Leu Arg Lys Glu Val Gln Thr Leu Arg Asp Arg Leu Pro Glu Met Leu
    450                 455                 460

Arg Asp Lys Ala Ser Leu Ser Gln Thr Asp Gly Pro Pro Ala Gly Ser
465                 470                 475                 480

Pro Gly Gln Asp Ser Asp Leu Arg Gln Glu Leu Asp Arg Leu His Arg
                485                 490                 495

Glu Leu Ala Glu Gly Arg Ala Gly Leu Ala Thr Gln Glu Gln Glu Leu
            500                 505                 510

Cys Arg Ala Gln Gly Leu Gln Glu Glu Leu Leu Gln Arg Leu Gln Glu
        515                 520                 525

Ala Gln Glu Arg Glu Ala Ala Thr Ala Ser Gln Thr Arg Ala Leu Ser
    530                 535                 540

Ser Gln Leu Gln Glu Ala Arg Ala Ala Gln Trp Glu Leu Glu Ala Gln
545                 550                 555                 560

Val Ser Ser Leu Ser Arg Gln Val Thr Gln Leu Gln Gly Gln Trp Glu
                565                 570                 575

Gln Arg Leu Glu Glu Ser Ser Gln Ala Lys Thr Ile His Thr Ala Ser
            580                 585                 590

Glu Thr Asn Gly Met Gly Pro Pro Glu Gly Gly Pro Gln Glu Ala Gln
        595                 600                 605
```

```
Leu Arg Lys Glu Val Ala Ala Leu Arg Glu Gln Leu Glu Gln Ala His
    610                 615                 620

Ser His Arg Pro Ser Gly Lys Glu Glu Ala Leu Cys Gln Leu Gln Glu
625                 630                 635                 640

Glu Asn Arg Arg Leu Ser Arg Glu Gln Glu Arg Leu Glu Ala Glu Leu
                645                 650                 655

Pro Gln Glu Gln Glu Ser Lys Gln Arg Leu Glu Gly Met Arg Arg Glu
            660                 665                 670

Thr Glu Ser Asn Trp Glu Ala Gln Leu Ala Asp Ile Leu Ser Trp Val
        675                 680                 685

Asn Asp Glu Lys Val Ser Arg Gly Tyr Leu Gln Ala Leu Ala Thr Lys
    690                 695                 700

Met Ala Glu Glu Leu Arg Ser Leu Arg Asn Val Gly Thr Gln Thr Leu
705                 710                 715                 720

Pro Ala Arg Pro Leu Lys Met Glu Ala Ser Ala Arg Leu Glu Leu Gln
                725                 730                 735

Ser Ala Leu Glu Ala Glu Ile Arg Ala Lys Gln Gly Leu Gln Glu Arg
            740                 745                 750

Leu Thr Gln Val Gln Glu Ala Gln Leu Gln Ala Glu Arg Arg Leu Gln
        755                 760                 765

Glu Ala Glu Lys Gln Ser Gln Ala Leu Gln Gln Glu Leu Ala Met Leu
    770                 775                 780

Arg Glu Glu Leu Gly Ala Arg Gly Pro Val Asp Thr Lys Pro Ser Asn
785                 790                 795                 800

Ser Leu Ile Pro Phe Leu Ser Phe Arg Ser Ser Glu Lys Asp Ser Ala
                805                 810                 815

Lys Asp Pro Gly Ile Ser Gly Glu Ala Thr Arg His Gly Gly Glu Pro
            820                 825                 830

Asp Leu Ser Arg Gln Gly Arg Arg Ser Leu Arg Met Gly Ala Val Phe
        835                 840                 845

Pro Arg Ala Pro Thr Ala Asn Thr Ala Ser Thr Glu Gly Leu Pro Ala
    850                 855                 860

Lys Gly Trp Gly Met Gly Pro Trp Ser Ala Leu Gly Asn Gly Cys Pro
865                 870                 875                 880

Pro Pro Gln Pro Gly Ser His Thr Leu Arg Pro Arg Ser Phe Pro Ser
                885                 890                 895

Pro Thr Lys Cys Leu Arg Cys Thr Phe Leu Leu Leu Gly Leu Gly Pro
            900                 905                 910

Arg Gly Leu Gly Cys Asp Ala Cys Gly Tyr Phe Cys His Thr Thr Cys
        915                 920                 925

Ala Pro Arg Pro Ser Pro Cys Pro Val Pro Pro Asp Leu Leu Arg Thr
    930                 935                 940

Ala Leu Gly Val His Pro Glu Thr Gly Thr Gly Thr Ala Tyr Glu Gly
945                 950                 955                 960

Phe Leu Ser Val Pro Arg Pro Ser Gly Val Arg Arg Gly Trp Gln Arg
                965                 970                 975

Val Phe Ala Ala Leu Ser Asp Ser Ala Leu Leu Leu Phe Asp Ala Pro
            980                 985                 990

Asp Leu Arg Leu Ser Pro Pro Ser  Gly Ala Leu Leu Gln  Val Leu Asp
        995                 1000                1005

Leu Arg  Asp Pro Gln Phe Ser  Ala Thr Pro Val Leu  Ala Ser Glu
    1010                1015                1020

Val Ile  His Ala Gln Ser Arg  Asp Leu Pro Arg Ile  Phe Arg Val
```

```
    1025                1030                1035

Thr Thr  Ser Gln Leu Ala Asp  Pro Pro Thr Thr Cys  Thr Val Leu
    1040                1045                1050

Leu Leu  Ala Glu Ser Glu Gly  Asp Trp Glu Arg Trp  Leu Gln Val
    1055                1060                1065

Leu Gly  Glu Leu Gln Arg Leu  Leu Leu Asp Ala Arg  Pro Arg Pro
    1070                1075                1080

Arg Pro  Val Tyr Thr Leu Lys  Glu Ala Tyr Asp Asn  Gly Leu Pro
    1085                1090                1095

Leu Leu  Pro His Thr Leu Cys  Ala Ala Ile Leu Asp  Gln Asp Arg
    1100                1105                1110

Leu Ala  Leu Gly Thr Glu Glu  Gly Leu Phe Val Ile  His Leu Arg
    1115                1120                1125

Ser Asn  Asp Ile Phe Gln Trp  Glu Gln Cys Arg Arg  Val Gln Gln
    1130                1135                1140

Leu Thr  Leu Ser Thr Gly Ala  Gly Leu Leu Val Val  Leu Cys Gly
    1145                1150                1155

Arg Gly  Pro Ser Val Arg Leu  Phe Ala Leu Ala Glu  Leu Glu Asn
    1160                1165                1170

Ile Glu  Val Ala Gly Ala Lys  Ile Pro Glu Ser Ala  Gly Cys Gln
    1175                1180                1185

Val Leu  Ala Ala Gly Ser Ile  Leu Gln Ala Arg Thr  Pro Val Leu
    1190                1195                1200

Cys Val  Ala Val Lys Arg Gln  Val Leu Cys Tyr Gln  Leu Gly Pro
    1205                1210                1215

Gly Pro  Gly Pro Trp Gln Arg  Arg Ile Arg Glu Leu  Gln Ala Pro
    1220                1225                1230

Ala Thr  Val Gln Ser Leu Gly  Leu Leu Gly Asp Arg  Leu Cys Val
    1235                1240                1245

Gly Ala  Ala Gly Gly Phe Ala  Leu Tyr Pro Leu Leu  Asn Glu Ala
    1250                1255                1260

Ala Pro  Leu Ala Leu Gly Ala  Gly Leu Val Pro Glu  Glu Leu Pro
    1265                1270                1275

Pro Ser  Arg Gly Gly Leu Gly  Glu Ala Leu Gly Ala  Val Glu Leu
    1280                1285                1290

Ser Leu  Ser Glu Phe Leu Leu  Leu Phe Thr Thr Ala  Gly Ile Tyr
    1295                1300                1305

Val Asp  Gly Ala Gly Arg Lys  Ser Arg Gly His Glu  Leu Leu Trp
    1310                1315                1320

Pro Ala  Ala Pro Met Gly Trp  Gly Tyr Ala Ala Pro  Tyr Leu Thr
    1325                1330                1335

Val Phe  Ser Glu Asn Ser Ile  Asp Val Phe Asp Val  Arg Arg Ala
    1340                1345                1350

Glu Trp  Val Gln Thr Val Pro  Leu Lys Lys Val Arg  Pro Leu Asn
    1355                1360                1365

Pro Glu  Gly Ser Leu Phe Leu  Tyr Gly Thr Glu Lys  Val Arg Leu
    1370                1375                1380

Thr Tyr  Leu Arg Asn Gln Leu  Ala Glu Lys Asp Glu  Phe Asp Ile
    1385                1390                1395

Pro Asp  Leu Thr Asp Asn Ser  Arg Arg Gln Leu Phe  Arg Thr Lys
    1400                1405                1410

Ser Lys  Arg Arg Phe Phe Phe  Arg Gly Ser Glu Glu  Gln Gln Lys
    1415                1420                1425
```

```
Gln Gln  Arg Arg Glu Met Leu  Lys Asp Pro Phe Val  Arg Ser Lys
    1430                 1435                 1440

Leu Ile  Ser Pro Pro Thr Asn  Phe Asn His Leu Val  His Val Gly
    1445                 1450                 1455

Pro Ala  Asn Gly Arg Pro Gly  Ala Arg Asp Lys Ser  Pro Ser Gln
    1460                 1465                 1470

Pro Leu  Arg Thr Val Thr Gln  Gln Ala Pro Glu Glu  Lys Gly Arg
    1475                 1480                 1485

Val Ala  Arg Gly Ser Gly Pro  Gln Arg Pro His Ser  Phe Ser Glu
    1490                 1495                 1500

Ala Leu  Arg Arg Pro Ala Ser  Met Gly Ser Glu Gly  Leu Gly Gly
    1505                 1510                 1515

Asp Ala  Asp Pro Thr Gly Ala  Val Lys Arg Lys Pro  Trp Thr Ser
    1520                 1525                 1530

Leu Ser  Ser Glu Ser Val Ser  Cys Pro Gln Gly Ser  Leu Ser Pro
    1535                 1540                 1545

Ala Thr  Ser Leu Met Gln Val  Ser Glu Arg Pro Arg  Ser Leu Pro
    1550                 1555                 1560

Leu Ser  Pro Glu Leu Glu Ser  Ser Pro
    1565                 1570
```

<210> SEQ ID NO 5
<211> LENGTH: 5373
<212> TYPE: DNA
<213> ORGANISM: Homo sapiens

<400> SEQUENCE: 5

```
atggagcggc ggctgcgcgc gctggagcag ctggcgcggg gcgaggccgg cggctgcccg     60

gggctcgacg gcctcctaga tctgctgctg gcgctgcacc acgagctcag cagcggcccc    120

ctacggcggg agcgcagcgt ggcgcagttc ctgagctggg ccagcccctt cgtatcaaag    180

gtgaaagaac tgcgtctgca gagagatgac tttgagatct tgaaggtgat cggccgagga    240

gcctttgggg aggtcaccgt ggtgaggcag agggacactg ggcagatttt tgccatgaaa    300

atgctgcaca agtgggagat gctgaagagg gctggagcag cctgtttccg ggaggagcgg    360

gatgtgctcg tgaaggtgaa cagccgttgg gtgaccactc tgcactatgc cttccaagac    420

gaggagtacc tgtaccttgt gatggactac tatgctggtg gggacctcct gacgctgctg    480

agccgcttcg aggaccgtct cccgcccgag ctggcccagt tctacctggc tgagatggtg    540

ctggccatcc actcgctgca ccagctgggt tatgtccaca gggactgcaa gccagacaac    600

gtcctgctgg atgtgaacgg gcacattcgc ctggctgact tcggctcctg cctgcgtctc    660

aacaccaacg gcctggcgga ttcatcagtg gcagtaggga cgccggacta tatctcccct    720

gagatcctgc aggtcctgga ggagggcaag ggccactacg gcccacagtg tatctggagg    780

tcgcttggag tctgcgccta tgagctgctc tttggggaga cgcccttcta tgctgagtcc    840

ttggtggaaa cctacggcaa gatcatgaac cacgaggacc acctgcagtt ccccccggac    900

gtgcctgacg tgccagccag cgcccaagac ctgatccgcc agctgctgtg tcgccaggaa    960

gagcggctgg gccgagtggg gctggatgac ttccggaacc atcctttctt cgaaggcgtg   1020

gactgggagc ggctggcgag cagcagcgcc ccctatattc ctgagctgcg gggcccaggg   1080

gacacctcca actttgatgt ggatgacgac accctcaacc atccagggac cctgccccgg   1140

ccctcccacg gggccttctc cggccatcac ctgccattcg tgggcttcac ctacacctca   1200

ggcagtcaca gtcctgagag cagctctgag gcttgggctg ccctggagcg gaagctccag   1260
```

-continued

```
tgtctggagc aggagaaggt ggagctgagc aggaagcacc aagaggccct gcacgccccc   1320
acagaccatc gggagctgga gcagctacgg aaggaagtgc agactctgcg ggacaggctg   1380
ccagagatgc tgagggacaa ggcctcattg tcccagacgg atgggccccc agctggtagc   1440
ccaggtcagg acagtgacct acggcaggag cttgaccgac ttcaccggga gctggccgag   1500
ggtcgggcag ggctggcgac tcaggagcag gagctctgca gggcccaggg gctgcaggag   1560
gagctgcttc agaggctaca ggaggcccag gagagagagg cggccacagc tagccagacc   1620
cgggccctga gctcccagct gcaggaggcc cgggctgccc agtgggagct ggaggcccag   1680
gtgtcctccc tgagccggca ggtgacgcag ctgcagggac agtgggagca acgccttgag   1740
gagtcgtccc aggccaagac catccacaca gcctctgaga ccaacgggat gggacccccct   1800
gagggtgggc ctcaggaggc ccaactgagg aaggaggtgg ccgccctgcg agagcagctg   1860
gagcaggccc acagccacag gccgagtggt aaggaggagg ctctgtgcca gctgcaggag   1920
gaaaaccgga ggctgagccg ggagcaggag cggctagaag ctgagctgcc ccaggagcag   1980
gagagcaagc agcggctgga gggtatgcgg cgggagacgg agagcaactg ggaggcccag   2040
ctcgccgaca tcctcagctg ggtgaatgat gagaaggtct caagaggcta cctgcaggcc   2100
ctggccacca agatggcaga ggagctgagg tccttgagga acgtaggcac ccagacgctc   2160
cctgcccggc cactgaagat ggaggcctcg gccaggctgg agctgcagtc agcgctggag   2220
gccgagatcc gcgccaagca gggcctgcag gagcggctga cacaggtgca ggaggcccag   2280
ctgcaggctg agcgccgtct gcaggaggcc gagaagcaga gccaggccct gcaacaggag   2340
ctcgccatgc tgcgggagga gctgggggcc cgagggccag tggacaccaa gccctcaaac   2400
tccctgattc ccttcctgtc cttccggagc tcagagaagg attctgccaa ggaccctggc   2460
atctcaggag aggccacaag gcatggagga gagccagatc tgagccggca gggccgacgc   2520
agcctgcgca tgggggctgt gttccccaga gcacccactg ccaacacagc ctctacagaa   2580
ggtcttcctg ctaagggatg gggcatgggg ccctggagcg ccttgggtaa tggctgtccc   2640
cctccccagc ccggctcaca cacgctgcgc ccccggagct tcccatcccc gaccaagtgt   2700
ctccgctgca ccttcctgtt gcttgggctg gggcccaggg gcttgggctg tgatgcctgc   2760
ggctactttt gtcacacaac ctgtgcccca cggccatcac cctgccccgt gccccctgac   2820
ctcctccgca cagccctggg agtacacccc gaaacaggca caggcactgc ctatgagggc   2880
tttctgtcgg tgccgcggcc ctcaggtgtc cggcggggct ggcagcgcgt gtttgctgcc   2940
ctgagtgact ccgccctgct gctgtttgac gcccctgacc tgaggctcag cccgcccagt   3000
ggggccctcc tgcaggtcct agatctgagg gacccccagt tctcggctac ccctgtcctg   3060
gcctctgagg ttatccatgc ccaatccagg gacctgccac gcatctttag ggtgacaacc   3120
tcccagctgg ctgatccgcc caccacgtgc actgtgctgc tgctggcaga gagcgagggg   3180
gactgggagc gctggctgca ggtgctgggt gagctgcagc ggctgctgct ggacgcgcgg   3240
ccaagacccc ggcccgtgta cacactcaag gaggcttacg acaacgggct gccgctgctg   3300
cctcacacgc tctgcgctgc catcctcgac caggatcgac ttgcgcttgg caccgaggag   3360
gggctctttg tcatccatct gcgcagcaac gacatcttcc agtgggagca gtgccggcgc   3420
gtgcagcagc tgaccttgag cacaggtgca ggcctgctgg tcgtgctgtg tggccgcggc   3480
cccagcgtgc gtctctttgc cctggcggag ctggagaaca tagaggtagc aggtgccaag   3540
atccccgagt ctgcaggctg ccaggtgctg gcagctggaa gcatcctgca ggcccgcacc   3600
ccggtgctct gtgtagccgt caagcgccag gtgctctgct accagctggg cccgggccct   3660
```

```
gggccctggc agcgccgcat ccgtgagctg caggcacctg ccactgtgca gagcctgggg   3720
ctgctgggag accggctatg tgtgggcgcc gccggtggct ttgcactcta cccgctgctc   3780
aacgaggctg cgccgttggc gctgggggcc ggtttggtgc ctgaggagct gccaccatcc   3840
cgcgggggcc tgggtgaggc actgggtgcc gtggagctta gcctcagcga gttcctgcta   3900
ctcttcacca ctgctggcat ctacgtggat ggcgcaggcc gcaagtctcg tggccacgag   3960
ctgttgtggc cagcagcgcc catgggctgg gggtatgcgg ccccctacct gacagtgttc   4020
agcgagaact ccatcgatgt gtttgacgtg aggagggcag aatgggtgca gaccgtgccg   4080
ctcaagaagg tgcggcccct caatccagag ggctccctgt tcctctacgg caccgagaag   4140
gtccgcctga cctacctcag gaaccagctg gcagagaagg acgagttcga catcccggac   4200
ctcaccgaca acagccggcg ccagctgttc cgcaccaaga gcaagcgccg cttctttttc   4260
cgcggctccg aggagcagca gaagcagcag cgcagggaga tgctgaagga cccttttgtg   4320
cgctccaagc tcatctcgcc gcctaccaac ttcaaccacc tagtacacgt gggccctgcc   4380
aacgggcggc ccggcgccag ggacaagtcc ccgtcccagc cctccgcac tgtcacccaa    4440
caggctcccg aagagaaggg ccgagttgcc cgcggctccg gcccacagcg gccccacagc   4500
ttctccgagg cgttgcggcg cccagcctcc atgggcagcg aaggcctcgg tggagacgca   4560
gaccccactg gagcagtgaa gaggaaaccc tggacatccc tgtccagcga gtctgtgtcc   4620
tgcccccagg gatcgctgag ccctgcaacc tccctaatgc aggtctcaga acggccccga   4680
agcctccccc tgtcccctga attggagagc tctccttgat gccctctgtt agggcccacc   4740
ccaatcccag ggcagaagga catgagggag caaagagctt gaggaatgcc atactccggc   4800
tggtccggga catggaaatt cggactcagg gaggacccgg gctgggcaat gactgggaga   4860
cttgcctggg ttcccaggac ttgggggtcc tgactcccag ccctcatcct gcctaccaac   4920
tctgttccca gccccagcct ttctaagcca ttgggaatag aatggcccct tttgttctgg   4980
tgtccagggg tgattgtgcc aaagctctta tttccagtgc caagccccca gaggcttgta   5040
agagttggga tgagggatgg agagggactg ggtctctggg aacaggttgg aggtcttatc   5100
tgtggactgt ctgactccca gctgaggcca agatggggca tgtccccgtc tctgcttagc   5160
gtctgggtga gaaaaacagg ctgtgatcca gaagaaggga agatagagaa ggagggagag   5220
gatgtaggcg aaggaggtga gagacaggat aggaggaagg aagtggagga ggaggtggta   5280
ggaattggaa ggaggtagaa gccgtgcaga ggaagagggg agagggacga aggaggagcg   5340
atgaagaaga ggagggagac aaaaaaaggg aag                                5373
```

<210> SEQ ID NO 6
<211> LENGTH: 1660
<212> TYPE: DNA
<213> ORGANISM: Homo sapiens

<400> SEQUENCE: 6

```
cctgcggcta cttttgtcac acaacctgtg ccccacaggc cccaccctgc cccgtgcccc     60
ctgacctcct ccgcacagcc ctgggagtac accccgaaac aggcacaggc actgcctatg    120
agggctttct gtcggtgccg cggccctcag gtgtccggcg gggctggcag cgcgtgtttg    180
ctgccctgag tgactcacgc ctgctgctgt ttgacgcccc tgacctgagg ctcagcccgc    240
ccagtggggc cctcctgcag gtcctagatc tgagggaccc ccagttctcg gctacccctg    300
tcctggcctc tgatgttatc catgcccaat ccagggacct gccacgcatc tttagggtga    360
caacctccca gctggcagtg ccgcccacca cgtgcactgt gctgctgctg gcagagagcg    420
```

```
agggggagcg ggaacgctgg ctgcaggtgc tgggtgagct gcagcggctg ctgctggacg    480

cgcggccaag accccggccc gtgtacacac tcaaggaggc ttacgacaac gggctgccgc    540

tgctgcctca cacgctctgc gctgccatcc tcgaccagga tcgacttgcg cttggcaccg    600

aggaggggct ctttgtcatc catctgcgca gcaacgacat cttccaggtg ggggagtgcc    660

ggcgcgtgca gcagctgacc ttgagcccca gtgcaggcct gctggtcgtg ctgtgtggcc    720

gcggccccag cgtgcgtctc tttgccctgg cggagctgga gaacatagag gtagcaggtg    780

cccaagatcc ccgagtctcg aggctgccag gtgctggcag ctggaagcat cctgcaggcc    840

cgcaccccgg tgctctgtgt agccgtcaag cgccaggtgc tctgctacca gctgggcccg    900

ggccctgggc cctggcagcg ccgcatccgt gagctgcagg cacctgccac tgtgcagagc    960

ctggggctgc tgggcgaccg gctatgtgtg ggcgccgccg gtggctttgc actctacccg   1020

ctgctcaacg aggctgcgcc gttggcgctg ggggccggtt tggtgcctga ggagctgcca   1080

ccatcccgcg gggcctgggg tgaggcactg ggtgccgtgg agcttagcct cagcgagttc   1140

ctgctactct tcaccactgc tggcatctac gtggatggcg caggccgcaa gtctcgtggc   1200

cacgagctgt tgtggccagc agcgcccatg ggctgggggt atgcggcccc ctacctgaca   1260

gtgttcagcg agaactccat cgatgtgttt gacgtgagga gggcagaatg ggtgcagacc   1320

gtgccgctca agaagggtgc ggcccctcaa tccagagggc tccctgttcc tctacggcac   1380

cgagaaggtc cgcctgacct acctcaggaa ccagctggca gagaaggacg agttcgacat   1440

cccggacctc accgacaaca gccggcgcca gctgttccgc accaagagca agcgccgctt   1500

ctttttccgc gtgtcggagg agcagcagaa gcagcagcgc agggagatgc tgaaggaccc   1560

ttttgtgcgc tccaagctca tctcgccgcc taccaacttc aaccacctag tacacgtggg   1620

ccctgccaac gggcggcccg gcgccaggga caagtccccg                         1660
```

<210> SEQ ID NO 7
<211> LENGTH: 19
<212> TYPE: DNA
<213> ORGANISM: Homo sapiens

<400> SEQUENCE: 7

```
gctggcatct acgtggatg                                                  19
```

<210> SEQ ID NO 8
<211> LENGTH: 20
<212> TYPE: DNA
<213> ORGANISM: Homo sapiens

<400> SEQUENCE: 8

```
gtggttgaag ttggtaggcg                                                 20
```

<210> SEQ ID NO 9
<211> LENGTH: 447
<212> TYPE: DNA
<213> ORGANISM: Homo sapiens

<400> SEQUENCE: 9

```
gctggcatct acgtggatgg cgcaggccgc aagtctcgtg gccacgagct gttgtggcca     60

gcagcgccca tgggctgggg gtatgcggcc ccctacctga cagtgttcag cgagaactcc    120

atcgatgtgt ttgacgtgag gagggcagaa tgggtgcaga ccgtgccgct caagaaggtg    180

cggcccctca atccagaggg ctccctgttc ctctacggca ccgagaaggt ccgcctgacc    240

tacctcagga accagctggc agagaaggac gagttcgaca tcccggacct caccgacaac    300
```

agccggcgcc agctgttccg caccaagagc aagcgccgct tctttttccg cgtgtcggag 360
gagcagcaga agcagcagcg cagggagatg ctgaaggacc cttttgtgcg ctccaagctc 420
atctcgccgc ctaccaactt caaccac 447

<210> SEQ ID NO 10
<211> LENGTH: 21
<212> TYPE: DNA
<213> ORGANISM: Homo sapiens

<400> SEQUENCE: 10
aaaggtgaaa gaactgcgtc t 21

<210> SEQ ID NO 11
<211> LENGTH: 21
<212> TYPE: RNA
<213> ORGANISM: Homo sapiens

<400> SEQUENCE: 11
aggugaaaga acugcgucuu u 21

<210> SEQ ID NO 12
<211> LENGTH: 21
<212> TYPE: RNA
<213> ORGANISM: Homo sapiens

<400> SEQUENCE: 12
uuuccacuuu cuugacgcag a 21

<210> SEQ ID NO 13
<211> LENGTH: 21
<212> TYPE: DNA
<213> ORGANISM: Homo sapiens

<400> SEQUENCE: 13
aaggtgaaag aactgcgtct g 21

<210> SEQ ID NO 14
<211> LENGTH: 21
<212> TYPE: RNA
<213> ORGANISM: Homo sapiens

<400> SEQUENCE: 14
ggugaaagaa cugcgucugu u 21

<210> SEQ ID NO 15
<211> LENGTH: 21
<212> TYPE: RNA
<213> ORGANISM: Homo sapiens

<400> SEQUENCE: 15
uuccacuuuc uugacgcaga c 21

<210> SEQ ID NO 16
<211> LENGTH: 21
<212> TYPE: DNA
<213> ORGANISM: Homo sapiens

<400> SEQUENCE: 16
aaagaactgc gtctgcagag a 21

<210> SEQ ID NO 17
<211> LENGTH: 21
<212> TYPE: RNA

<213> ORGANISM: Homo sapiens

<400> SEQUENCE: 17
agaacugcgu cugcagagau u 21

<210> SEQ ID NO 18
<211> LENGTH: 21
<212> TYPE: RNA
<213> ORGANISM: Homo sapiens

<400> SEQUENCE: 18
uuucuugacg cagacgucuc u 21

<210> SEQ ID NO 19
<211> LENGTH: 21
<212> TYPE: DNA
<213> ORGANISM: Homo sapiens

<400> SEQUENCE: 19
aacggcatgg tggattcatc a 21

<210> SEQ ID NO 20
<211> LENGTH: 21
<212> TYPE: RNA
<213> ORGANISM: Homo sapiens

<400> SEQUENCE: 20
cggcauggug gauucaucau u 21

<210> SEQ ID NO 21
<211> LENGTH: 21
<212> TYPE: RNA
<213> ORGANISM: Homo sapiens

<400> SEQUENCE: 21
uugccguacc accuaaguag u 21

<210> SEQ ID NO 22
<211> LENGTH: 21
<212> TYPE: DNA
<213> ORGANISM: Homo sapiens

<400> SEQUENCE: 22
aaacctacgg caagatcatg a 21

<210> SEQ ID NO 23
<211> LENGTH: 21
<212> TYPE: RNA
<213> ORGANISM: Homo sapiens

<400> SEQUENCE: 23
accuacggca agaucaugau u 21

<210> SEQ ID NO 24
<211> LENGTH: 21
<212> TYPE: RNA
<213> ORGANISM: Homo sapiens

<400> SEQUENCE: 24
uuuggaugcc guucuaguac u 21

<210> SEQ ID NO 25
<211> LENGTH: 21
<212> TYPE: DNA

<213> ORGANISM: Homo sapiens

<400> SEQUENCE: 25
aacctacggc aagatcatga a 21

<210> SEQ ID NO 26
<211> LENGTH: 21
<212> TYPE: RNA
<213> ORGANISM: Homo sapiens

<400> SEQUENCE: 26
ccuacggcaa gaucaugaau u 21

<210> SEQ ID NO 27
<211> LENGTH: 21
<212> TYPE: RNA
<213> ORGANISM: Homo sapiens

<400> SEQUENCE: 27
uuggaugccg uucuaguacu u 21

<210> SEQ ID NO 28
<211> LENGTH: 21
<212> TYPE: DNA
<213> ORGANISM: Homo sapiens

<400> SEQUENCE: 28
aagatcatga accacgagga c 21

<210> SEQ ID NO 29
<211> LENGTH: 21
<212> TYPE: RNA
<213> ORGANISM: Homo sapiens

<400> SEQUENCE: 29
gaucaugaac cacgaggacu u 21

<210> SEQ ID NO 30
<211> LENGTH: 21
<212> TYPE: RNA
<213> ORGANISM: Homo sapiens

<400> SEQUENCE: 30
uucuaguacu uggugcuccu g 21

<210> SEQ ID NO 31
<211> LENGTH: 21
<212> TYPE: DNA
<213> ORGANISM: Homo sapiens

<400> SEQUENCE: 31
aaccatcctt tcttcgaagg c 21

<210> SEQ ID NO 32
<211> LENGTH: 21
<212> TYPE: RNA
<213> ORGANISM: Homo sapiens

<400> SEQUENCE: 32
ccauccuuuc uucgaaggcu u 21

<210> SEQ ID NO 33
<211> LENGTH: 21
<212> TYPE: RNA

<213> ORGANISM: Homo sapiens

<400> SEQUENCE: 33
uugguaggaa agaagcuucc g 21

<210> SEQ ID NO 34
<211> LENGTH: 21
<212> TYPE: DNA
<213> ORGANISM: Homo sapiens

<400> SEQUENCE: 34
aactttgatg tggatgacga c 21

<210> SEQ ID NO 35
<211> LENGTH: 21
<212> TYPE: RNA
<213> ORGANISM: Homo sapiens

<400> SEQUENCE: 35
cuuugaugug gaugacgacu u 21

<210> SEQ ID NO 36
<211> LENGTH: 21
<212> TYPE: RNA
<213> ORGANISM: Homo sapiens

<400> SEQUENCE: 36
uugaaacuac accuacugcu g 21

<210> SEQ ID NO 37
<211> LENGTH: 21
<212> TYPE: DNA
<213> ORGANISM: Homo sapiens

<400> SEQUENCE: 37
aatgatgaga aggtctcaag a 21

<210> SEQ ID NO 38
<211> LENGTH: 21
<212> TYPE: RNA
<213> ORGANISM: Homo sapiens

<400> SEQUENCE: 38
ugaugagaag gucucaagau u 21

<210> SEQ ID NO 39
<211> LENGTH: 21
<212> TYPE: RNA
<213> ORGANISM: Homo sapiens

<400> SEQUENCE: 39
uuacuacucu uccagaguuc u 21

<210> SEQ ID NO 40
<211> LENGTH: 21
<212> TYPE: DNA
<213> ORGANISM: Homo sapiens

<400> SEQUENCE: 40
aacacagcct ctacagaagg t 21

<210> SEQ ID NO 41
<211> LENGTH: 21
<212> TYPE: RNA

<213> ORGANISM: Homo sapiens

<400> SEQUENCE: 41
cacagccucu acagaagguu u 21

<210> SEQ ID NO 42
<211> LENGTH: 21
<212> TYPE: RNA
<213> ORGANISM: Homo sapiens

<400> SEQUENCE: 42
uugugucgga gaugucuucc a 21

<210> SEQ ID NO 43
<211> LENGTH: 21
<212> TYPE: DNA
<213> ORGANISM: Homo sapiens

<400> SEQUENCE: 43
aactccatcg atgtgtttga c 21

<210> SEQ ID NO 44
<211> LENGTH: 21
<212> TYPE: RNA
<213> ORGANISM: Homo sapiens

<400> SEQUENCE: 44
cuccaucgau guguuugacu u 21

<210> SEQ ID NO 45
<211> LENGTH: 21
<212> TYPE: RNA
<213> ORGANISM: Homo sapiens

<400> SEQUENCE: 45
uugagguagc uacacaaacu g 21

<210> SEQ ID NO 46
<211> LENGTH: 21
<212> TYPE: DNA
<213> ORGANISM: Homo sapiens

<400> SEQUENCE: 46
aacttcaacc acctagtaca c 21

<210> SEQ ID NO 47
<211> LENGTH: 21
<212> TYPE: RNA
<213> ORGANISM: Homo sapiens

<400> SEQUENCE: 47
cuucaaccac cuaguacacu u 21

<210> SEQ ID NO 48
<211> LENGTH: 21
<212> TYPE: RNA
<213> ORGANISM: Homo sapiens

<400> SEQUENCE: 48
uugaaguugg uggaucaugu g 21

<210> SEQ ID NO 49
<211> LENGTH: 21
<212> TYPE: DNA

<213> ORGANISM: Homo sapiens

<400> SEQUENCE: 49
caaaggtgaa agaactgcgt c 21

<210> SEQ ID NO 50
<211> LENGTH: 21
<212> TYPE: RNA
<213> ORGANISM: Homo sapiens

<400> SEQUENCE: 50
aaggugaaag aacugcgucu u 21

<210> SEQ ID NO 51
<211> LENGTH: 21
<212> TYPE: RNA
<213> ORGANISM: Homo sapiens

<400> SEQUENCE: 51
uuuuccacuu ucuugacgca g 21

<210> SEQ ID NO 52
<211> LENGTH: 21
<212> TYPE: DNA
<213> ORGANISM: Homo sapiens

<400> SEQUENCE: 52
cagagagatg actttgagat c 21

<210> SEQ ID NO 53
<211> LENGTH: 21
<212> TYPE: RNA
<213> ORGANISM: Homo sapiens

<400> SEQUENCE: 53
gagagaugac uuugagaucu u 21

<210> SEQ ID NO 54
<211> LENGTH: 21
<212> TYPE: RNA
<213> ORGANISM: Homo sapiens

<400> SEQUENCE: 54
uucucucuac ugaaacucua g 21

<210> SEQ ID NO 55
<211> LENGTH: 21
<212> TYPE: DNA
<213> ORGANISM: Homo sapiens

<400> SEQUENCE: 55
cactctgcac tatgccttcc a 21

<210> SEQ ID NO 56
<211> LENGTH: 21
<212> TYPE: RNA
<213> ORGANISM: Homo sapiens

<400> SEQUENCE: 56
cucugcacua ugccuuccau u 21

<210> SEQ ID NO 57
<211> LENGTH: 21
<212> TYPE: RNA

<213> ORGANISM: Homo sapiens

<400> SEQUENCE: 57
uugagacgug auacggaagg u 21

<210> SEQ ID NO 58
<211> LENGTH: 21
<212> TYPE: DNA
<213> ORGANISM: Homo sapiens

<400> SEQUENCE: 58
cactatgcct tccaagacga g 21

<210> SEQ ID NO 59
<211> LENGTH: 21
<212> TYPE: RNA
<213> ORGANISM: Homo sapiens

<400> SEQUENCE: 59
cuaugccuuc caagacgagu u 21

<210> SEQ ID NO 60
<211> LENGTH: 21
<212> TYPE: RNA
<213> ORGANISM: Homo sapiens

<400> SEQUENCE: 60
uugauacgga agguucugcu c 21

<210> SEQ ID NO 61
<211> LENGTH: 21
<212> TYPE: DNA
<213> ORGANISM: Homo sapiens

<400> SEQUENCE: 61
caagacgagg agtacctgta c 21

<210> SEQ ID NO 62
<211> LENGTH: 21
<212> TYPE: RNA
<213> ORGANISM: Homo sapiens

<400> SEQUENCE: 62
agacgaggag uaccuguacu u 21

<210> SEQ ID NO 63
<211> LENGTH: 21
<212> TYPE: RNA
<213> ORGANISM: Homo sapiens

<400> SEQUENCE: 63
uuucugcucc ucauggacau g 21

<210> SEQ ID NO 64
<211> LENGTH: 21
<212> TYPE: DNA
<213> ORGANISM: Homo sapiens

<400> SEQUENCE: 64
cagttctacc tggctgagat g 21

<210> SEQ ID NO 65
<211> LENGTH: 21
<212> TYPE: RNA

<213> ORGANISM: Homo sapiens

<400> SEQUENCE: 65
guucuaccug gcugagaugu u 21

<210> SEQ ID NO 66
<211> LENGTH: 21
<212> TYPE: RNA
<213> ORGANISM: Homo sapiens

<400> SEQUENCE: 66
uucaagaugg accgacucua c 21

<210> SEQ ID NO 67
<211> LENGTH: 21
<212> TYPE: DNA
<213> ORGANISM: Homo sapiens

<400> SEQUENCE: 67
caacgtcctg ctggatgtga a 21

<210> SEQ ID NO 68
<211> LENGTH: 21
<212> TYPE: RNA
<213> ORGANISM: Homo sapiens

<400> SEQUENCE: 68
acguccugcu ggaugugaau u 21

<210> SEQ ID NO 69
<211> LENGTH: 21
<212> TYPE: RNA
<213> ORGANISM: Homo sapiens

<400> SEQUENCE: 69
uuugcaggac gaccuacacu u 21

<210> SEQ ID NO 70
<211> LENGTH: 21
<212> TYPE: DNA
<213> ORGANISM: Homo sapiens

<400> SEQUENCE: 70
caacggcatg gtggattcat c 21

<210> SEQ ID NO 71
<211> LENGTH: 21
<212> TYPE: RNA
<213> ORGANISM: Homo sapiens

<400> SEQUENCE: 71
acggcauggu ggauucaucu u 21

<210> SEQ ID NO 72
<211> LENGTH: 21
<212> TYPE: RNA
<213> ORGANISM: Homo sapiens

<400> SEQUENCE: 72
uuugccguac caccuaagua g 21

<210> SEQ ID NO 73
<211> LENGTH: 21
<212> TYPE: DNA

<213> ORGANISM: Homo sapiens

<400> SEQUENCE: 73
catggtggat tcatcagtgg c 21

<210> SEQ ID NO 74
<211> LENGTH: 21
<212> TYPE: RNA
<213> ORGANISM: Homo sapiens

<400> SEQUENCE: 74
ugguggauuc aucaguggcu u 21

<210> SEQ ID NO 75
<211> LENGTH: 21
<212> TYPE: RNA
<213> ORGANISM: Homo sapiens

<400> SEQUENCE: 75
uuaccaccua aguagucacc g 21

<210> SEQ ID NO 76
<211> LENGTH: 21
<212> TYPE: DNA
<213> ORGANISM: Homo sapiens

<400> SEQUENCE: 76
caagatcatg aaccacgagg a 21

<210> SEQ ID NO 77
<211> LENGTH: 21
<212> TYPE: RNA
<213> ORGANISM: Homo sapiens

<400> SEQUENCE: 77
agaucaugaa ccacgaggau u 21

<210> SEQ ID NO 78
<211> LENGTH: 21
<212> TYPE: RNA
<213> ORGANISM: Homo sapiens

<400> SEQUENCE: 78
uuucuaguac uuggugcucc u 21

<210> SEQ ID NO 79
<211> LENGTH: 21
<212> TYPE: DNA
<213> ORGANISM: Homo sapiens

<400> SEQUENCE: 79
catcctttct tcgaaggcgt g 21

<210> SEQ ID NO 80
<211> LENGTH: 21
<212> TYPE: RNA
<213> ORGANISM: Homo sapiens

<400> SEQUENCE: 80
uccuuucuuc gaaggcgugu u 21

<210> SEQ ID NO 81
<211> LENGTH: 21
<212> TYPE: RNA

<213> ORGANISM: Homo sapiens

<400> SEQUENCE: 81
uuaggaaaga agcuuccgca c 21

<210> SEQ ID NO 82
<211> LENGTH: 21
<212> TYPE: DNA
<213> ORGANISM: Homo sapiens

<400> SEQUENCE: 82
catggacacc tccaactttg a 21

<210> SEQ ID NO 83
<211> LENGTH: 21
<212> TYPE: RNA
<213> ORGANISM: Homo sapiens

<400> SEQUENCE: 83
uggacaccuc caacuuugau u 21

<210> SEQ ID NO 84
<211> LENGTH: 21
<212> TYPE: RNA
<213> ORGANISM: Homo sapiens

<400> SEQUENCE: 84
uuaccugugg agguugaaac u 21

<210> SEQ ID NO 85
<211> LENGTH: 21
<212> TYPE: DNA
<213> ORGANISM: Homo sapiens

<400> SEQUENCE: 85
cacctccaac tttgatgtgg a 21

<210> SEQ ID NO 86
<211> LENGTH: 21
<212> TYPE: RNA
<213> ORGANISM: Homo sapiens

<400> SEQUENCE: 86
ccuccaacuu ugauguggau u 21

<210> SEQ ID NO 87
<211> LENGTH: 21
<212> TYPE: RNA
<213> ORGANISM: Homo sapiens

<400> SEQUENCE: 87
uuggagguug aaacuacacc u 21

<210> SEQ ID NO 88
<211> LENGTH: 21
<212> TYPE: DNA
<213> ORGANISM: Homo sapiens

<400> SEQUENCE: 88
caactttgat gtggatgacg a 21

<210> SEQ ID NO 89
<211> LENGTH: 21
<212> TYPE: RNA

<213> ORGANISM: Homo sapiens

<400> SEQUENCE: 89
acuuugaugu ggaugacgau u 21

<210> SEQ ID NO 90
<211> LENGTH: 21
<212> TYPE: RNA
<213> ORGANISM: Homo sapiens

<400> SEQUENCE: 90
uuugaaacua caccuacugc u 21

<210> SEQ ID NO 91
<211> LENGTH: 21
<212> TYPE: DNA
<213> ORGANISM: Homo sapiens

<400> SEQUENCE: 91
cagagaagga ttctgccaag g 21

<210> SEQ ID NO 92
<211> LENGTH: 21
<212> TYPE: RNA
<213> ORGANISM: Homo sapiens

<400> SEQUENCE: 92
gagaaggauu cugccaaggu u 21

<210> SEQ ID NO 93
<211> LENGTH: 21
<212> TYPE: RNA
<213> ORGANISM: Homo sapiens

<400> SEQUENCE: 93
uucucuuccu aagacgguuc c 21

<210> SEQ ID NO 94
<211> LENGTH: 21
<212> TYPE: DNA
<213> ORGANISM: Homo sapiens

<400> SEQUENCE: 94
caacacagcc tctacagaag g 21

<210> SEQ ID NO 95
<211> LENGTH: 21
<212> TYPE: RNA
<213> ORGANISM: Homo sapiens

<400> SEQUENCE: 95
acacagccuc uacagaaggu u 21

<210> SEQ ID NO 96
<211> LENGTH: 21
<212> TYPE: RNA
<213> ORGANISM: Homo sapiens

<400> SEQUENCE: 96
uuugugucgg agaugucuuc c 21

<210> SEQ ID NO 97
<211> LENGTH: 21
<212> TYPE: DNA

<213> ORGANISM: Homo sapiens

<400> SEQUENCE: 97
cacagcctct acagaaggtc t 21

<210> SEQ ID NO 98
<211> LENGTH: 21
<212> TYPE: RNA
<213> ORGANISM: Homo sapiens

<400> SEQUENCE: 98
cagccucuac agaaggucuu u 21

<210> SEQ ID NO 99
<211> LENGTH: 21
<212> TYPE: RNA
<213> ORGANISM: Homo sapiens

<400> SEQUENCE: 99
uugucggaga ugucuuccag a 21

<210> SEQ ID NO 100
<211> LENGTH: 21
<212> TYPE: DNA
<213> ORGANISM: Homo sapiens

<400> SEQUENCE: 100
cagcctctac agaaggtctt c 21

<210> SEQ ID NO 101
<211> LENGTH: 21
<212> TYPE: RNA
<213> ORGANISM: Homo sapiens

<400> SEQUENCE: 101
gccucuacag aaggucuucu u 21

<210> SEQ ID NO 102
<211> LENGTH: 21
<212> TYPE: RNA
<213> ORGANISM: Homo sapiens

<400> SEQUENCE: 102
uucggagaug ucuuccagaa g 21

<210> SEQ ID NO 103
<211> LENGTH: 21
<212> TYPE: DNA
<213> ORGANISM: Homo sapiens

<400> SEQUENCE: 103
cagaaggtct tcctgctaag g 21

<210> SEQ ID NO 104
<211> LENGTH: 21
<212> TYPE: RNA
<213> ORGANISM: Homo sapiens

<400> SEQUENCE: 104
gaaggucuuc cugcuaaggu u 21

<210> SEQ ID NO 105
<211> LENGTH: 21
<212> TYPE: RNA

<213> ORGANISM: Homo sapiens

<400> SEQUENCE: 105
uucuuccaga aggacgauuc c 21

<210> SEQ ID NO 106
<211> LENGTH: 21
<212> TYPE: DNA
<213> ORGANISM: Homo sapiens

<400> SEQUENCE: 106
cacactcaag gaggcttacg a 21

<210> SEQ ID NO 107
<211> LENGTH: 21
<212> TYPE: RNA
<213> ORGANISM: Homo sapiens

<400> SEQUENCE: 107
cacucaagga ggcuuacgau u 21

<210> SEQ ID NO 108
<211> LENGTH: 21
<212> TYPE: RNA
<213> ORGANISM: Homo sapiens

<400> SEQUENCE: 108
uugugaguuc cuccgaaugc u 21

<210> SEQ ID NO 109
<211> LENGTH: 21
<212> TYPE: DNA
<213> ORGANISM: Homo sapiens

<400> SEQUENCE: 109
cactcaagga ggcttacgac a 21

<210> SEQ ID NO 110
<211> LENGTH: 21
<212> TYPE: RNA
<213> ORGANISM: Homo sapiens

<400> SEQUENCE: 110
cucaaggagg cuuacgacau u 21

<210> SEQ ID NO 111
<211> LENGTH: 21
<212> TYPE: RNA
<213> ORGANISM: Homo sapiens

<400> SEQUENCE: 111
uugaguuccu ccgaaugcug u 21

<210> SEQ ID NO 112
<211> LENGTH: 21
<212> TYPE: DNA
<213> ORGANISM: Homo sapiens

<400> SEQUENCE: 112
cagcaacgac atcttccagg t 21

<210> SEQ ID NO 113
<211> LENGTH: 21
<212> TYPE: RNA

<213> ORGANISM: Homo sapiens

<400> SEQUENCE: 113
gcaacgacau cuuccagguu u 21

<210> SEQ ID NO 114
<211> LENGTH: 21
<212> TYPE: RNA
<213> ORGANISM: Homo sapiens

<400> SEQUENCE: 114
uucguugcug uagaagqucc a 21

<210> SEQ ID NO 115
<211> LENGTH: 21
<212> TYPE: DNA
<213> ORGANISM: Homo sapiens

<400> SEQUENCE: 115
catagaggta gcaggtgcca a 21

<210> SEQ ID NO 116
<211> LENGTH: 21
<212> TYPE: RNA
<213> ORGANISM: Homo sapiens

<400> SEQUENCE: 116
uagagguagc aggugccaau u 21

<210> SEQ ID NO 117
<211> LENGTH: 21
<212> TYPE: RNA
<213> ORGANISM: Homo sapiens

<400> SEQUENCE: 117
uuaucuccau cguccacggu u 21

<210> SEQ ID NO 118
<211> LENGTH: 21
<212> TYPE: DNA
<213> ORGANISM: Homo sapiens

<400> SEQUENCE: 118
cagcgagttc ctgctactct t 21

<210> SEQ ID NO 119
<211> LENGTH: 21
<212> TYPE: RNA
<213> ORGANISM: Homo sapiens

<400> SEQUENCE: 119
gcgaguuccu gcuacucuuu u 21

<210> SEQ ID NO 120
<211> LENGTH: 21
<212> TYPE: RNA
<213> ORGANISM: Homo sapiens

<400> SEQUENCE: 120
uucgcucaag gacgaugaga a 21

<210> SEQ ID NO 121
<211> LENGTH: 21
<212> TYPE: DNA

<213> ORGANISM: Homo sapiens

<400> SEQUENCE: 121
cagtgttcag cgagaactcc a 21

<210> SEQ ID NO 122
<211> LENGTH: 21
<212> TYPE: RNA
<213> ORGANISM: Homo sapiens

<400> SEQUENCE: 122
guguucagcg agaacuccau u 21

<210> SEQ ID NO 123
<211> LENGTH: 21
<212> TYPE: RNA
<213> ORGANISM: Homo sapiens

<400> SEQUENCE: 123
uucacaaguc gcucuugagg u 21

<210> SEQ ID NO 124
<211> LENGTH: 21
<212> TYPE: DNA
<213> ORGANISM: Homo sapiens

<400> SEQUENCE: 124
cagcgagaac tccatcgatg t 21

<210> SEQ ID NO 125
<211> LENGTH: 21
<212> TYPE: RNA
<213> ORGANISM: Homo sapiens

<400> SEQUENCE: 125
gcgagaacuc caucgauguu u 21

<210> SEQ ID NO 126
<211> LENGTH: 21
<212> TYPE: RNA
<213> ORGANISM: Homo sapiens

<400> SEQUENCE: 126
uucgcucuug agguagcuac a 21

<210> SEQ ID NO 127
<211> LENGTH: 21
<212> TYPE: DNA
<213> ORGANISM: Homo sapiens

<400> SEQUENCE: 127
catcgatgtg tttgacgtga g 21

<210> SEQ ID NO 128
<211> LENGTH: 21
<212> TYPE: RNA
<213> ORGANISM: Homo sapiens

<400> SEQUENCE: 128
ucgauguguu ugacgugagu u 21

<210> SEQ ID NO 129
<211> LENGTH: 21
<212> TYPE: RNA

<213> ORGANISM: Homo sapiens

<400> SEQUENCE: 129
uuagcuacac aaacugcacu c 21

<210> SEQ ID NO 130
<211> LENGTH: 21
<212> TYPE: DNA
<213> ORGANISM: Homo sapiens

<400> SEQUENCE: 130
cagagaagga cgagttcgac a 21

<210> SEQ ID NO 131
<211> LENGTH: 21
<212> TYPE: RNA
<213> ORGANISM: Homo sapiens

<400> SEQUENCE: 131
gagaaggacg aguucgacau u 21

<210> SEQ ID NO 132
<211> LENGTH: 21
<212> TYPE: RNA
<213> ORGANISM: Homo sapiens

<400> SEQUENCE: 132
uucucuuccu gcucaagcug u 21

<210> SEQ ID NO 133
<211> LENGTH: 21
<212> TYPE: DNA
<213> ORGANISM: Homo sapiens

<400> SEQUENCE: 133
caacttcaac cacctagtac a 21

<210> SEQ ID NO 134
<211> LENGTH: 21
<212> TYPE: RNA
<213> ORGANISM: Homo sapiens

<400> SEQUENCE: 134
acuucaacca ccuaguacau u 21

<210> SEQ ID NO 135
<211> LENGTH: 21
<212> TYPE: RNA
<213> ORGANISM: Homo sapiens

<400> SEQUENCE: 135
uuugaaguug guggaucaug u 21

<210> SEQ ID NO 136
<211> LENGTH: 21
<212> TYPE: DNA
<213> ORGANISM: Homo sapiens

<400> SEQUENCE: 136
gaaagaactg cgtctgcaga g 21

<210> SEQ ID NO 137
<211> LENGTH: 21
<212> TYPE: RNA

<213> ORGANISM: Homo sapiens

<400> SEQUENCE: 137
aagaacugcg ucugcagagu u 21

<210> SEQ ID NO 138
<211> LENGTH: 21
<212> TYPE: RNA
<213> ORGANISM: Homo sapiens

<400> SEQUENCE: 138
uuuucuugac gcagacgucu c 21

<210> SEQ ID NO 139
<211> LENGTH: 21
<212> TYPE: DNA
<213> ORGANISM: Homo sapiens

<400> SEQUENCE: 139
gaactgcgtc tgcagagaga t 21

<210> SEQ ID NO 140
<211> LENGTH: 21
<212> TYPE: RNA
<213> ORGANISM: Homo sapiens

<400> SEQUENCE: 140
acugcgucug cagagagauu u 21

<210> SEQ ID NO 141
<211> LENGTH: 21
<212> TYPE: RNA
<213> ORGANISM: Homo sapiens

<400> SEQUENCE: 141
uuugacgcag acgucucucu a 21

<210> SEQ ID NO 142
<211> LENGTH: 21
<212> TYPE: DNA
<213> ORGANISM: Homo sapiens

<400> SEQUENCE: 142
gagagatgac tttgagatct t 21

<210> SEQ ID NO 143
<211> LENGTH: 21
<212> TYPE: RNA
<213> ORGANISM: Homo sapiens

<400> SEQUENCE: 143
gagaugacuu ugagaucuuu u 21

<210> SEQ ID NO 144
<211> LENGTH: 21
<212> TYPE: RNA
<213> ORGANISM: Homo sapiens

<400> SEQUENCE: 144
uucucuacug aaacucuaga a 21

<210> SEQ ID NO 145
<211> LENGTH: 21
<212> TYPE: DNA

<213> ORGANISM: Homo sapiens

<400> SEQUENCE: 145
gagatgactt tgagatcttg a 21

<210> SEQ ID NO 146
<211> LENGTH: 21
<212> TYPE: RNA
<213> ORGANISM: Homo sapiens

<400> SEQUENCE: 146
gaugacuuug agaucuugau u 21

<210> SEQ ID NO 147
<211> LENGTH: 21
<212> TYPE: RNA
<213> ORGANISM: Homo sapiens

<400> SEQUENCE: 147
uucuacugaa acucuagaac u 21

<210> SEQ ID NO 148
<211> LENGTH: 21
<212> TYPE: DNA
<213> ORGANISM: Homo sapiens

<400> SEQUENCE: 148
gatgactttg agatcttgaa g 21

<210> SEQ ID NO 149
<211> LENGTH: 21
<212> TYPE: RNA
<213> ORGANISM: Homo sapiens

<400> SEQUENCE: 149
ugacuuugag aucuugaagu u 21

<210> SEQ ID NO 150
<211> LENGTH: 21
<212> TYPE: RNA
<213> ORGANISM: Homo sapiens

<400> SEQUENCE: 150
uuacugaaac ucuagaacuu c 21

<210> SEQ ID NO 151
<211> LENGTH: 21
<212> TYPE: DNA
<213> ORGANISM: Homo sapiens

<400> SEQUENCE: 151
gactttgaga tcttgaaggt g 21

<210> SEQ ID NO 152
<211> LENGTH: 21
<212> TYPE: RNA
<213> ORGANISM: Homo sapiens

<400> SEQUENCE: 152
cuuugagauc uugaaggugu u 21

<210> SEQ ID NO 153
<211> LENGTH: 21
<212> TYPE: RNA

<213> ORGANISM: Homo sapiens

<400> SEQUENCE: 153
uugaaacucu agaacuucca c 21

<210> SEQ ID NO 154
<211> LENGTH: 21
<212> TYPE: DNA
<213> ORGANISM: Homo sapiens

<400> SEQUENCE: 154
gagatcttga aggtgatcgg c 21

<210> SEQ ID NO 155
<211> LENGTH: 21
<212> TYPE: RNA
<213> ORGANISM: Homo sapiens

<400> SEQUENCE: 155
gaucuugaag gugaucggcu u 21

<210> SEQ ID NO 156
<211> LENGTH: 21
<212> TYPE: RNA
<213> ORGANISM: Homo sapiens

<400> SEQUENCE: 156
uucuagaacu uccacuagcc g 21

<210> SEQ ID NO 157
<211> LENGTH: 21
<212> TYPE: DNA
<213> ORGANISM: Homo sapiens

<400> SEQUENCE: 157
gaccactctg cactatgcct t 21

<210> SEQ ID NO 158
<211> LENGTH: 21
<212> TYPE: RNA
<213> ORGANISM: Homo sapiens

<400> SEQUENCE: 158
ccacucugca cuaugccuuu u 21

<210> SEQ ID NO 159
<211> LENGTH: 21
<212> TYPE: RNA
<213> ORGANISM: Homo sapiens

<400> SEQUENCE: 159
uuggugagac gugauacgga a 21

<210> SEQ ID NO 160
<211> LENGTH: 21
<212> TYPE: DNA
<213> ORGANISM: Homo sapiens

<400> SEQUENCE: 160
gacgaggagt acctgtacct t 21

<210> SEQ ID NO 161
<211> LENGTH: 21
<212> TYPE: RNA

<213> ORGANISM: Homo sapiens

<400> SEQUENCE: 161
cgaggaguac cuguaccuuu u 21

<210> SEQ ID NO 162
<211> LENGTH: 21
<212> TYPE: RNA
<213> ORGANISM: Homo sapiens

<400> SEQUENCE: 162
uugcuccuca uggacaugga a 21

<210> SEQ ID NO 163
<211> LENGTH: 21
<212> TYPE: DNA
<213> ORGANISM: Homo sapiens

<400> SEQUENCE: 163
gaggagtacc tgtaccttgt g 21

<210> SEQ ID NO 164
<211> LENGTH: 21
<212> TYPE: RNA
<213> ORGANISM: Homo sapiens

<400> SEQUENCE: 164
ggaguaccug uaccuugugu u 21

<210> SEQ ID NO 165
<211> LENGTH: 21
<212> TYPE: RNA
<213> ORGANISM: Homo sapiens

<400> SEQUENCE: 165
uuccucaugg acauggaaca c 21

<210> SEQ ID NO 166
<211> LENGTH: 21
<212> TYPE: DNA
<213> ORGANISM: Homo sapiens

<400> SEQUENCE: 166
gagtacctgt accttgtgat g 21

<210> SEQ ID NO 167
<211> LENGTH: 21
<212> TYPE: RNA
<213> ORGANISM: Homo sapiens

<400> SEQUENCE: 167
guaccuguac cuugugaugu u 21

<210> SEQ ID NO 168
<211> LENGTH: 21
<212> TYPE: RNA
<213> ORGANISM: Homo sapiens

<400> SEQUENCE: 168
uucauggaca uggaacacua c 21

<210> SEQ ID NO 169
<211> LENGTH: 21
<212> TYPE: DNA

<213> ORGANISM: Homo sapiens

<400> SEQUENCE: 169
gatggactac tatgctggtg g 21

<210> SEQ ID NO 170
<211> LENGTH: 21
<212> TYPE: RNA
<213> ORGANISM: Homo sapiens

<400> SEQUENCE: 170
uggacuacua ugcugguggu u 21

<210> SEQ ID NO 171
<211> LENGTH: 21
<212> TYPE: RNA
<213> ORGANISM: Homo sapiens

<400> SEQUENCE: 171
uuaccugaug auacgaccac c 21

<210> SEQ ID NO 172
<211> LENGTH: 21
<212> TYPE: DNA
<213> ORGANISM: Homo sapiens

<400> SEQUENCE: 172
gatgtcaagc cagacaacgt c 21

<210> SEQ ID NO 173
<211> LENGTH: 21
<212> TYPE: RNA
<213> ORGANISM: Homo sapiens

<400> SEQUENCE: 173
ugucaagcca gacaacgucu u 21

<210> SEQ ID NO 174
<211> LENGTH: 21
<212> TYPE: RNA
<213> ORGANISM: Homo sapiens

<400> SEQUENCE: 174
uuacaguucg gucuguugca g 21

<210> SEQ ID NO 175
<211> LENGTH: 21
<212> TYPE: DNA
<213> ORGANISM: Homo sapiens

<400> SEQUENCE: 175
gagtccttgg tggaaaccta c 21

<210> SEQ ID NO 176
<211> LENGTH: 21
<212> TYPE: RNA
<213> ORGANISM: Homo sapiens

<400> SEQUENCE: 176
guccuuggug gaaaccuacu u 21

<210> SEQ ID NO 177
<211> LENGTH: 21
<212> TYPE: RNA

<213> ORGANISM: Homo sapiens

<400> SEQUENCE: 177
uucaggaacc accuuuggau g 21

<210> SEQ ID NO 178
<211> LENGTH: 21
<212> TYPE: DNA
<213> ORGANISM: Homo sapiens

<400> SEQUENCE: 178
gaaacctacg gcaagatcat g 21

<210> SEQ ID NO 179
<211> LENGTH: 21
<212> TYPE: RNA
<213> ORGANISM: Homo sapiens

<400> SEQUENCE: 179
aaccuacggc aagaucaugu u 21

<210> SEQ ID NO 180
<211> LENGTH: 21
<212> TYPE: RNA
<213> ORGANISM: Homo sapiens

<400> SEQUENCE: 180
uuuuggaugc cguucuagua c 21

<210> SEQ ID NO 181
<211> LENGTH: 21
<212> TYPE: DNA
<213> ORGANISM: Homo sapiens

<400> SEQUENCE: 181
gatcatgaac cacgaggacc a 21

<210> SEQ ID NO 182
<211> LENGTH: 21
<212> TYPE: RNA
<213> ORGANISM: Homo sapiens

<400> SEQUENCE: 182
ucaugaacca cgaggaccau u 21

<210> SEQ ID NO 183
<211> LENGTH: 21
<212> TYPE: RNA
<213> ORGANISM: Homo sapiens

<400> SEQUENCE: 183
uuaguacuug gugcuccugg u 21

<210> SEQ ID NO 184
<211> LENGTH: 21
<212> TYPE: DNA
<213> ORGANISM: Homo sapiens

<400> SEQUENCE: 184
gatgacttcc ggaaccatcc t 21

<210> SEQ ID NO 185
<211> LENGTH: 21
<212> TYPE: RNA

<213> ORGANISM: Homo sapiens

<400> SEQUENCE: 185
ugacuuccgg aaccauccuu u 21

<210> SEQ ID NO 186
<211> LENGTH: 21
<212> TYPE: RNA
<213> ORGANISM: Homo sapiens

<400> SEQUENCE: 186
uuacugaagg ccuugguagg a 21

<210> SEQ ID NO 187
<211> LENGTH: 21
<212> TYPE: DNA
<213> ORGANISM: Homo sapiens

<400> SEQUENCE: 187
gacttccgga accatccttt c 21

<210> SEQ ID NO 188
<211> LENGTH: 21
<212> TYPE: RNA
<213> ORGANISM: Homo sapiens

<400> SEQUENCE: 188
cuuccggaac cauccuuucu u 21

<210> SEQ ID NO 189
<211> LENGTH: 21
<212> TYPE: RNA
<213> ORGANISM: Homo sapiens

<400> SEQUENCE: 189
uugaaggccu ugguaggaaa g 21

<210> SEQ ID NO 190
<211> LENGTH: 21
<212> TYPE: DNA
<213> ORGANISM: Homo sapiens

<400> SEQUENCE: 190
gaaccatcct ttcttcgaag g 21

<210> SEQ ID NO 191
<211> LENGTH: 21
<212> TYPE: RNA
<213> ORGANISM: Homo sapiens

<400> SEQUENCE: 191
accauccuuu cuucgaaggu u 21

<210> SEQ ID NO 192
<211> LENGTH: 21
<212> TYPE: RNA
<213> ORGANISM: Homo sapiens

<400> SEQUENCE: 192
uuugguagga aagaagcuuc c 21

<210> SEQ ID NO 193
<211> LENGTH: 21
<212> TYPE: DNA

<213> ORGANISM: Homo sapiens

<400> SEQUENCE: 193
gacacctcca actttgatgt g 21

<210> SEQ ID NO 194
<211> LENGTH: 21
<212> TYPE: RNA
<213> ORGANISM: Homo sapiens

<400> SEQUENCE: 194
caccuccaac uuugaugugu u 21

<210> SEQ ID NO 195
<211> LENGTH: 21
<212> TYPE: RNA
<213> ORGANISM: Homo sapiens

<400> SEQUENCE: 195
uuguggaggu ugaaacuaca c 21

<210> SEQ ID NO 196
<211> LENGTH: 21
<212> TYPE: DNA
<213> ORGANISM: Homo sapiens

<400> SEQUENCE: 196
gaatgatgag aaggtctcaa g 21

<210> SEQ ID NO 197
<211> LENGTH: 21
<212> TYPE: RNA
<213> ORGANISM: Homo sapiens

<400> SEQUENCE: 197
augaugagaa ggucucaagu u 21

<210> SEQ ID NO 198
<211> LENGTH: 21
<212> TYPE: RNA
<213> ORGANISM: Homo sapiens

<400> SEQUENCE: 198
uuuacuacuc uuccagaguu c 21

<210> SEQ ID NO 199
<211> LENGTH: 21
<212> TYPE: DNA
<213> ORGANISM: Homo sapiens

<400> SEQUENCE: 199
gatgagaagg tctcaagagg c 21

<210> SEQ ID NO 200
<211> LENGTH: 21
<212> TYPE: RNA
<213> ORGANISM: Homo sapiens

<400> SEQUENCE: 200
ugagaagguc ucaagaggcu u 21

<210> SEQ ID NO 201
<211> LENGTH: 21
<212> TYPE: RNA

<213> ORGANISM: Homo sapiens

<400> SEQUENCE: 201
uuacucuucc agaguucucc g 21

<210> SEQ ID NO 202
<211> LENGTH: 21
<212> TYPE: DNA
<213> ORGANISM: Homo sapiens

<400> SEQUENCE: 202
gagaaggtct caagaggcta c 21

<210> SEQ ID NO 203
<211> LENGTH: 21
<212> TYPE: RNA
<213> ORGANISM: Homo sapiens

<400> SEQUENCE: 203
gaaggucuca agaggcuacu u 21

<210> SEQ ID NO 204
<211> LENGTH: 21
<212> TYPE: RNA
<213> ORGANISM: Homo sapiens

<400> SEQUENCE: 204
uucuuccaga guucuccgau g 21

<210> SEQ ID NO 205
<211> LENGTH: 21
<212> TYPE: DNA
<213> ORGANISM: Homo sapiens

<400> SEQUENCE: 205
gaaggtctca agaggctacc t 21

<210> SEQ ID NO 206
<211> LENGTH: 21
<212> TYPE: RNA
<213> ORGANISM: Homo sapiens

<400> SEQUENCE: 206
aggucucaag aggcuaccuu u 21

<210> SEQ ID NO 207
<211> LENGTH: 21
<212> TYPE: RNA
<213> ORGANISM: Homo sapiens

<400> SEQUENCE: 207
uuuccagagu ucuccgaugg a 21

<210> SEQ ID NO 208
<211> LENGTH: 21
<212> TYPE: DNA
<213> ORGANISM: Homo sapiens

<400> SEQUENCE: 208
gagctcagag aaggattctg c 21

<210> SEQ ID NO 209
<211> LENGTH: 21
<212> TYPE: RNA

<213> ORGANISM: Homo sapiens

<400> SEQUENCE: 209
gcucagagaa ggauucugcu u 21

<210> SEQ ID NO 210
<211> LENGTH: 21
<212> TYPE: RNA
<213> ORGANISM: Homo sapiens

<400> SEQUENCE: 210
uucgagucuc uuccuaagac g 21

<210> SEQ ID NO 211
<211> LENGTH: 21
<212> TYPE: DNA
<213> ORGANISM: Homo sapiens

<400> SEQUENCE: 211
gagaaggatt ctgccaagga c 21

<210> SEQ ID NO 212
<211> LENGTH: 21
<212> TYPE: RNA
<213> ORGANISM: Homo sapiens

<400> SEQUENCE: 212
gaaggauucu gccaaggacu u 21

<210> SEQ ID NO 213
<211> LENGTH: 21
<212> TYPE: RNA
<213> ORGANISM: Homo sapiens

<400> SEQUENCE: 213
uucuuccuaa gacgguuccu g 21

<210> SEQ ID NO 214
<211> LENGTH: 21
<212> TYPE: DNA
<213> ORGANISM: Homo sapiens

<400> SEQUENCE: 214
gagctggaga acatagaggt a 21

<210> SEQ ID NO 215
<211> LENGTH: 21
<212> TYPE: RNA
<213> ORGANISM: Homo sapiens

<400> SEQUENCE: 215
gcuggagaac auagagguau u 21

<210> SEQ ID NO 216
<211> LENGTH: 21
<212> TYPE: RNA
<213> ORGANISM: Homo sapiens

<400> SEQUENCE: 216
uucgaccucu uguaucucca u 21

<210> SEQ ID NO 217
<211> LENGTH: 21
<212> TYPE: DNA

<213> ORGANISM: Homo sapiens

<400> SEQUENCE: 217
gagaacatag aggtagcagg t 21

<210> SEQ ID NO 218
<211> LENGTH: 21
<212> TYPE: RNA
<213> ORGANISM: Homo sapiens

<400> SEQUENCE: 218
gaacauagag guagcagguu u 21

<210> SEQ ID NO 219
<211> LENGTH: 21
<212> TYPE: RNA
<213> ORGANISM: Homo sapiens

<400> SEQUENCE: 219
uucuuguauc uccaucgucc a 21

<210> SEQ ID NO 220
<211> LENGTH: 21
<212> TYPE: DNA
<213> ORGANISM: Homo sapiens

<400> SEQUENCE: 220
gaacatagag gtagcaggtg c 21

<210> SEQ ID NO 221
<211> LENGTH: 21
<212> TYPE: RNA
<213> ORGANISM: Homo sapiens

<400> SEQUENCE: 221
acauagaggu agcaggugcu u 21

<210> SEQ ID NO 222
<211> LENGTH: 21
<212> TYPE: RNA
<213> ORGANISM: Homo sapiens

<400> SEQUENCE: 222
uuuguaucuc caucguccac g 21

<210> SEQ ID NO 223
<211> LENGTH: 21
<212> TYPE: DNA
<213> ORGANISM: Homo sapiens

<400> SEQUENCE: 223
gagttcctgc tactcttcac c 21

<210> SEQ ID NO 224
<211> LENGTH: 21
<212> TYPE: RNA
<213> ORGANISM: Homo sapiens

<400> SEQUENCE: 224
guuccugcua cucuucaccu u 21

<210> SEQ ID NO 225
<211> LENGTH: 21
<212> TYPE: RNA

<213> ORGANISM: Homo sapiens

<400> SEQUENCE: 225
uucaaggacg augagaagug g 21

<210> SEQ ID NO 226
<211> LENGTH: 21
<212> TYPE: DNA
<213> ORGANISM: Homo sapiens

<400> SEQUENCE: 226
gacagtgttc agcgagaact c 21

<210> SEQ ID NO 227
<211> LENGTH: 21
<212> TYPE: RNA
<213> ORGANISM: Homo sapiens

<400> SEQUENCE: 227
caguguucag cgagaacucu u 21

<210> SEQ ID NO 228
<211> LENGTH: 21
<212> TYPE: RNA
<213> ORGANISM: Homo sapiens

<400> SEQUENCE: 228
uugucacaag ucgcucuuga g 21

<210> SEQ ID NO 229
<211> LENGTH: 21
<212> TYPE: DNA
<213> ORGANISM: Homo sapiens

<400> SEQUENCE: 229
gagaactcca tcgatgtgtt t 21

<210> SEQ ID NO 230
<211> LENGTH: 21
<212> TYPE: RNA
<213> ORGANISM: Homo sapiens

<400> SEQUENCE: 230
gaacuccauc gauguguuuu u 21

<210> SEQ ID NO 231
<211> LENGTH: 21
<212> TYPE: RNA
<213> ORGANISM: Homo sapiens

<400> SEQUENCE: 231
uucuugaggu agcuacacaa a 21

<210> SEQ ID NO 232
<211> LENGTH: 21
<212> TYPE: DNA
<213> ORGANISM: Homo sapiens

<400> SEQUENCE: 232
gaactccatc gatgtgtttg a 21

<210> SEQ ID NO 233
<211> LENGTH: 21
<212> TYPE: RNA

<213> ORGANISM: Homo sapiens

<400> SEQUENCE: 233
acuccaucga uguguuugau u 21

<210> SEQ ID NO 234
<211> LENGTH: 21
<212> TYPE: RNA
<213> ORGANISM: Homo sapiens

<400> SEQUENCE: 234
uuugagguag cuacacaaac u 21

<210> SEQ ID NO 235
<211> LENGTH: 21
<212> TYPE: DNA
<213> ORGANISM: Homo sapiens

<400> SEQUENCE: 235
gatgtgtttg acgtgaggag g 21

<210> SEQ ID NO 236
<211> LENGTH: 21
<212> TYPE: RNA
<213> ORGANISM: Homo sapiens

<400> SEQUENCE: 236
uguguuugac gugaggaggu u 21

<210> SEQ ID NO 237
<211> LENGTH: 21
<212> TYPE: RNA
<213> ORGANISM: Homo sapiens

<400> SEQUENCE: 237
uuacacaaac ugcacuccuc c 21

<210> SEQ ID NO 238
<211> LENGTH: 21
<212> TYPE: DNA
<213> ORGANISM: Homo sapiens

<400> SEQUENCE: 238
gagaaggacg agttcgacat c 21

<210> SEQ ID NO 239
<211> LENGTH: 21
<212> TYPE: RNA
<213> ORGANISM: Homo sapiens

<400> SEQUENCE: 239
gaaggacgag uucgacaucu u 21

<210> SEQ ID NO 240
<211> LENGTH: 21
<212> TYPE: RNA
<213> ORGANISM: Homo sapiens

<400> SEQUENCE: 240
uucuuccugc ucaagcugua g 21

<210> SEQ ID NO 241
<211> LENGTH: 21
<212> TYPE: DNA

<213> ORGANISM: Homo sapiens

<400> SEQUENCE: 241
tatcaaaggt gaaagaactg c 21

<210> SEQ ID NO 242
<211> LENGTH: 21
<212> TYPE: RNA
<213> ORGANISM: Homo sapiens

<400> SEQUENCE: 242
ucaaagguga aagaacugcu u 21

<210> SEQ ID NO 243
<211> LENGTH: 21
<212> TYPE: RNA
<213> ORGANISM: Homo sapiens

<400> SEQUENCE: 243
uuaguuucca cuuucuugac g 21

<210> SEQ ID NO 244
<211> LENGTH: 21
<212> TYPE: DNA
<213> ORGANISM: Homo sapiens

<400> SEQUENCE: 244
tacctgtacc ttgtgatgga c 21

<210> SEQ ID NO 245
<211> LENGTH: 21
<212> TYPE: RNA
<213> ORGANISM: Homo sapiens

<400> SEQUENCE: 245
ccuguaccuu gugauggacu u 21

<210> SEQ ID NO 246
<211> LENGTH: 21
<212> TYPE: RNA
<213> ORGANISM: Homo sapiens

<400> SEQUENCE: 246
uuggacaugg aacacuaccu g 21

<210> SEQ ID NO 247
<211> LENGTH: 21
<212> TYPE: DNA
<213> ORGANISM: Homo sapiens

<400> SEQUENCE: 247
taccttgtga tggactacta t 21

<210> SEQ ID NO 248
<211> LENGTH: 21
<212> TYPE: RNA
<213> ORGANISM: Homo sapiens

<400> SEQUENCE: 248
ccuugugaug gacuacuauu u 21

<210> SEQ ID NO 249
<211> LENGTH: 21
<212> TYPE: RNA

<213> ORGANISM: Homo sapiens

<400> SEQUENCE: 249
uuggaacacu accugaugau a 21

<210> SEQ ID NO 250
<211> LENGTH: 21
<212> TYPE: DNA
<213> ORGANISM: Homo sapiens

<400> SEQUENCE: 250
tatgctgagt ccttggtgga a 21

<210> SEQ ID NO 251
<211> LENGTH: 21
<212> TYPE: RNA
<213> ORGANISM: Homo sapiens

<400> SEQUENCE: 251
ugcugagucc uugguggaau u 21

<210> SEQ ID NO 252
<211> LENGTH: 21
<212> TYPE: RNA
<213> ORGANISM: Homo sapiens

<400> SEQUENCE: 252
uuacgacuca ggaaccaccu u 21

<210> SEQ ID NO 253
<211> LENGTH: 21
<212> TYPE: DNA
<213> ORGANISM: Homo sapiens

<400> SEQUENCE: 253
tacggcaaga tcatgaacca c 21

<210> SEQ ID NO 254
<211> LENGTH: 21
<212> TYPE: RNA
<213> ORGANISM: Homo sapiens

<400> SEQUENCE: 254
cggcaagauc augaaccacu u 21

<210> SEQ ID NO 255
<211> LENGTH: 21
<212> TYPE: RNA
<213> ORGANISM: Homo sapiens

<400> SEQUENCE: 255
uugccguucu aguacuuggu g 21

<210> SEQ ID NO 256
<211> LENGTH: 21
<212> TYPE: DNA
<213> ORGANISM: Homo sapiens

<400> SEQUENCE: 256
tacagaaggt cttcctgcta a 21

<210> SEQ ID NO 257
<211> LENGTH: 21
<212> TYPE: RNA

<213> ORGANISM: Homo sapiens

<400> SEQUENCE: 257
cagaaggucu uccugcuaau u 21

<210> SEQ ID NO 258
<211> LENGTH: 21
<212> TYPE: RNA
<213> ORGANISM: Homo sapiens

<400> SEQUENCE: 258
uugucuucca gaaggacgau u 21

<210> SEQ ID NO 259
<211> LENGTH: 21
<212> TYPE: DNA
<213> ORGANISM: Homo sapiens

<400> SEQUENCE: 259
tacacactca aggaggctta c 21

<210> SEQ ID NO 260
<211> LENGTH: 21
<212> TYPE: RNA
<213> ORGANISM: Homo sapiens

<400> SEQUENCE: 260
cacacucaag gaggcuuacu u 21

<210> SEQ ID NO 261
<211> LENGTH: 21
<212> TYPE: RNA
<213> ORGANISM: Homo sapiens

<400> SEQUENCE: 261
uugugugagu uccuccgaau g 21

<210> SEQ ID NO 262
<211> LENGTH: 21
<212> TYPE: DNA
<213> ORGANISM: Homo sapiens

<400> SEQUENCE: 262
taccaacttc aaccacctag t 21

<210> SEQ ID NO 263
<211> LENGTH: 21
<212> TYPE: RNA
<213> ORGANISM: Homo sapiens

<400> SEQUENCE: 263
ccaacuucaa ccaccuaguu u 21

<210> SEQ ID NO 264
<211> LENGTH: 21
<212> TYPE: RNA
<213> ORGANISM: Homo sapiens

<400> SEQUENCE: 264
uugguugaag uugguggauc a 21

<210> SEQ ID NO 265
<211> LENGTH: 21
<212> TYPE: DNA

<213> ORGANISM: Homo sapiens

<400> SEQUENCE: 265
aacggcatgg tggattcatc a 21

<210> SEQ ID NO 266
<211> LENGTH: 21
<212> TYPE: RNA
<213> ORGANISM: Homo sapiens

<400> SEQUENCE: 266
cggcauggug gauucaucau u 21

<210> SEQ ID NO 267
<211> LENGTH: 21
<212> TYPE: RNA
<213> ORGANISM: Homo sapiens

<400> SEQUENCE: 267
uugccguacc accuaaguag u 21

<210> SEQ ID NO 268
<211> LENGTH: 21
<212> TYPE: DNA
<213> ORGANISM: Homo sapiens

<400> SEQUENCE: 268
aacctacggc aagatcatga a 21

<210> SEQ ID NO 269
<211> LENGTH: 21
<212> TYPE: RNA
<213> ORGANISM: Homo sapiens

<400> SEQUENCE: 269
ccuacggcaa gaucaugaau u 21

<210> SEQ ID NO 270
<211> LENGTH: 21
<212> TYPE: RNA
<213> ORGANISM: Homo sapiens

<400> SEQUENCE: 270
uuggaugccg uucuaguacu u 21

<210> SEQ ID NO 271
<211> LENGTH: 21
<212> TYPE: DNA
<213> ORGANISM: Homo sapiens

<400> SEQUENCE: 271
cactatgcct tccaagacga g 21

<210> SEQ ID NO 272
<211> LENGTH: 21
<212> TYPE: RNA
<213> ORGANISM: Homo sapiens

<400> SEQUENCE: 272
cuaugccuuc caagacgagu u 21

<210> SEQ ID NO 273
<211> LENGTH: 21
<212> TYPE: RNA

<213> ORGANISM: Homo sapiens

<400> SEQUENCE: 273
uugauacgga agguucugcu c 21

<210> SEQ ID NO 274
<211> LENGTH: 21
<212> TYPE: DNA
<213> ORGANISM: Homo sapiens

<400> SEQUENCE: 274
caacggcatg gtggattcat c 21

<210> SEQ ID NO 275
<211> LENGTH: 21
<212> TYPE: RNA
<213> ORGANISM: Homo sapiens

<400> SEQUENCE: 275
acggcauggu ggauucaucu u 21

<210> SEQ ID NO 276
<211> LENGTH: 21
<212> TYPE: RNA
<213> ORGANISM: Homo sapiens

<400> SEQUENCE: 276
uuugccguac caccuaagua g 21

<210> SEQ ID NO 277
<211> LENGTH: 21
<212> TYPE: DNA
<213> ORGANISM: Homo sapiens

<400> SEQUENCE: 277
catggtggat tcatcagtgg c 21

<210> SEQ ID NO 278
<211> LENGTH: 21
<212> TYPE: RNA
<213> ORGANISM: Homo sapiens

<400> SEQUENCE: 278
ugguggauuc aucaguggcu u 21

<210> SEQ ID NO 279
<211> LENGTH: 21
<212> TYPE: RNA
<213> ORGANISM: Homo sapiens

<400> SEQUENCE: 279
uuaccaccua aguagucacc g 21

<210> SEQ ID NO 280
<211> LENGTH: 21
<212> TYPE: DNA
<213> ORGANISM: Homo sapiens

<400> SEQUENCE: 280
cagcctctac agaaggtctt c 21

<210> SEQ ID NO 281
<211> LENGTH: 21
<212> TYPE: RNA

<213> ORGANISM: Homo sapiens

<400> SEQUENCE: 281
gccucuacag aaggucuucu u 21

<210> SEQ ID NO 282
<211> LENGTH: 21
<212> TYPE: RNA
<213> ORGANISM: Homo sapiens

<400> SEQUENCE: 282
uucggagaug ucuuccagaa g 21

<210> SEQ ID NO 283
<211> LENGTH: 21
<212> TYPE: DNA
<213> ORGANISM: Homo sapiens

<400> SEQUENCE: 283
cagcgagaac tccatcgatg t 21

<210> SEQ ID NO 284
<211> LENGTH: 21
<212> TYPE: RNA
<213> ORGANISM: Homo sapiens

<400> SEQUENCE: 284
gcgagaacuc caucgauguu u 21

<210> SEQ ID NO 285
<211> LENGTH: 21
<212> TYPE: RNA
<213> ORGANISM: Homo sapiens

<400> SEQUENCE: 285
uucgcucuug agguagcuac a 21

<210> SEQ ID NO 286
<211> LENGTH: 21
<212> TYPE: DNA
<213> ORGANISM: Homo sapiens

<400> SEQUENCE: 286
cagagaagga cgagttcgac a 21

<210> SEQ ID NO 287
<211> LENGTH: 21
<212> TYPE: RNA
<213> ORGANISM: Homo sapiens

<400> SEQUENCE: 287
gagaaggacg aguucgacau u 21

<210> SEQ ID NO 288
<211> LENGTH: 21
<212> TYPE: RNA
<213> ORGANISM: Homo sapiens

<400> SEQUENCE: 288
uucucuuccu gcucaagcug u 21

<210> SEQ ID NO 289
<211> LENGTH: 21
<212> TYPE: DNA

```
<213> ORGANISM: Homo sapiens

<400> SEQUENCE: 289

gagatcttga aggtgatcgg c                                              21


<210> SEQ ID NO 290
<211> LENGTH: 21
<212> TYPE: RNA
<213> ORGANISM: Homo sapiens

<400> SEQUENCE: 290

gaucuugaag gugaucggcu u                                              21


<210> SEQ ID NO 291
<211> LENGTH: 21
<212> TYPE: RNA
<213> ORGANISM: Homo sapiens

<400> SEQUENCE: 291

uucuagaacu uccacuagcc g                                              21


<210> SEQ ID NO 292
<211> LENGTH: 21
<212> TYPE: DNA
<213> ORGANISM: Homo sapiens

<400> SEQUENCE: 292

gaaggtctca agaggctacc t                                              21


<210> SEQ ID NO 293
<211> LENGTH: 21
<212> TYPE: RNA
<213> ORGANISM: Homo sapiens

<400> SEQUENCE: 293

aggucucaag aggcuaccuu u                                              21


<210> SEQ ID NO 294
<211> LENGTH: 21
<212> TYPE: RNA
<213> ORGANISM: Homo sapiens

<400> SEQUENCE: 294

uuuccagagu ucuccgaugg a                                              21


<210> SEQ ID NO 295
<211> LENGTH: 21
<212> TYPE: DNA
<213> ORGANISM: Homo sapiens

<400> SEQUENCE: 295

gagaacatag aggtagcagg t                                              21


<210> SEQ ID NO 296
<211> LENGTH: 21
<212> TYPE: RNA
<213> ORGANISM: Homo sapiens

<400> SEQUENCE: 296

gaacauagag guagcagguu u                                              21


<210> SEQ ID NO 297
<211> LENGTH: 21
<212> TYPE: RNA
```

<213> ORGANISM: Homo sapiens

<400> SEQUENCE: 297
uucuuguauc uccaucgucc a 21

<210> SEQ ID NO 298
<211> LENGTH: 21
<212> TYPE: DNA
<213> ORGANISM: Homo sapiens

<400> SEQUENCE: 298
gacagtgttc agcgagaact c 21

<210> SEQ ID NO 299
<211> LENGTH: 21
<212> TYPE: RNA
<213> ORGANISM: Homo sapiens

<400> SEQUENCE: 299
caguguucag cgagaacucu u 21

<210> SEQ ID NO 300
<211> LENGTH: 21
<212> TYPE: RNA
<213> ORGANISM: Homo sapiens

<400> SEQUENCE: 300
uugucacaag ucgcucuuga g 21

<210> SEQ ID NO 301
<211> LENGTH: 21
<212> TYPE: DNA
<213> ORGANISM: Homo sapiens

<400> SEQUENCE: 301
gagaaggacg agttcgacat c 21

<210> SEQ ID NO 302
<211> LENGTH: 21
<212> TYPE: RNA
<213> ORGANISM: Homo sapiens

<400> SEQUENCE: 302
gaaggacgag uucgacaucu u 21

<210> SEQ ID NO 303
<211> LENGTH: 21
<212> TYPE: RNA
<213> ORGANISM: Homo sapiens

<400> SEQUENCE: 303
uucuuccugc ucaagcugua g 21

<210> SEQ ID NO 304
<211> LENGTH: 21
<212> TYPE: DNA
<213> ORGANISM: Homo sapiens

<400> SEQUENCE: 304
tacggcaaga tcatgaacca c 21

<210> SEQ ID NO 305
<211> LENGTH: 21
<212> TYPE: RNA

-continued

```
<213> ORGANISM: Homo sapiens

<400> SEQUENCE: 305

cggcaagauc augaaccacu u                                       21


<210> SEQ ID NO 306
<211> LENGTH: 21
<212> TYPE: RNA
<213> ORGANISM: Homo sapiens

<400> SEQUENCE: 306

uugccguucu aguacuuggu g                                       21
```

COMPOSITION EMPLOYING A NOVEL HUMAN KINASE

The present invention incorporates by reference U.S. Provisional Application Ser. No. 60/429,381, filed Nov. 27, 2002 and entitled "Compositions, Organisms and Methodologies Employing A Novel Human Kinase."

FIELD OF THE INVENTION

The present invention relates to compositions, organisms and methodologies employing a novel human protein kinase, MRCK1, which has 65% sequence homology to rat myotonic dystrophy kinase-related Cdc42 binding kinase (MRCK). This invention can be used for diagnosing, prognosing and treating kinase-related diseases and, in particular, diseases associated with aberrant expression of MRCK1.

BACKGROUND OF THE INVENTION

Protein kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1,000 of the 10,000 proteins active in a typical mammalian cell are phosphorylated. As is well known in the art, the high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc.), cell cycle checkpoints, and environmental or nutritional stresses. The phosphorylation process is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups: those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250-300 amino acid catalytic domain. The primary structure of the kinase domains is conserved and can be further subdivided into 11 subdomains. The N-terminal of the kinase domain, which contains subdomains I-IV, generally folds into a lobe-like structure that binds and orients the ATP (or GTP) donor molecule. The C terminal of the kinase domain forms a larger lobe, which contains subdomains VI-XI, binds the protein substrate and carries out the transfer of the gamma phosphate from ATP to the hydroxyl group of a serine, threonine, or tyrosine residue. Subdomain V spans the two lobes. Each of the 11 subdomains contains specific residues and motifs or patterns of amino acids that are characteristic of that subdomain and are highly conserved.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein.

The presence or absence of a phosphate moiety modulates protein function in multiple ways. A common mechanism involves changes in the catalytic properties (Vmax and Km) of an enzyme, leading to its activation or inactivation.

A second widely recognized mechanism involves promoting protein-protein interactions. An example of this is the tyrosine autophosphorylation of the ligand-activated EGF receptor tyrosine kinase. This event triggers the high-affinity binding to the phosphotyrosine residue on the receptor's C-terminal intracellular domain to the SH2 motif of an adaptor molecule Grb2. Grb2, in turn, binds through its SH3 motif to a second adaptor molecule, such as SHC. The formation of this ternary complex activates the signaling events that are responsible for the biological effects of EGF. Serine and threonine phosphorylation events also have been recently recognized to exert their biological function through protein-protein interaction events that are mediated by the high-affinity binding of phosphoserine and phosphothreonine to the WW motifs present in a large variety of proteins.

A third important outcome of protein phosphorylation is changes in the subcellular localization of the substrate. As an example, nuclear import and export events in a large diversity of proteins are regulated by protein phosphorylation.

Many kinases are involved in regulatory cascades wherein their substrates may include other kinases whose activities are regulated by their phosphorylation state. Ultimately the activities of some downstream effectors are modulated by phosphorylation resulting from activation of such a pathway.

Myotonic dystrophy kinase-related Cdc42 binding kinases (MRCKs) are serine/threonine kinases. MRCKs have been implicated in the morphological activities of Cdc42 in non-neural cells and are suggest to be downstream effectors of Cdc42 in cytoskeletal reorganization. At least two types of MRCKs, MRCK alpha and MRCK beta, have been identified. MRCKs interact with the GTP-bound form of Cdc42 and, to a lesser extent, the GTP-bound form of Rac. The catalytic domain of MRCKs phosphorylates non-muscle myosin light chain 2 at serine 19. The phosphorylation is believed to be involved in myosin contractile activity and associated changes in the organization of actin microfilaments in intact cells.

MRCK alpha and Rho-binding kinase (ROK) alpha are believed to have contrasting roles in regulating neurite morphology. ROK alpha acts downstream of RhoA in inducing neurite retraction, while MRCK alpha acts downstream of Cdc42/Rac1 in promoting neurite outgrowth. The neurite outgrowth induced by either kinase-dead ROK alpha or nerve growth factor can be effectively blocked by a kinase-dead and p21-binding deficient MRCK alpha mutant. In addition, expression of kinase-dead MRCK alpha blocks $Cdc42^{V12}$-dependent formation of focal complexes and peripheral microspikes. Microinjection of a plasmid encoding MRCK alpha results in actin and myosin reorganization.

MRCKs have multiple functional domains. These domains include three coiled-coil alpha-helix domains, a cysteine-rich motif resembling those of protein kinase C and n-chimaerin, and a Pleckstrin homology domain. Native MRCK kinases tend to form high-molecular-weight multimers. The intermolecular interactions among the three coiled-coil domains and the N-terminal region preceding the kinase domain in MRCK alpha are believed to be responsible for the multimerization.

MRCK alpha can be activated by the N-terminus-mediated dimerization. The dimerization leads to trans-autophosphorylation of MRCK kinases. In addition, MRCK alpha kinases can be negatively regulated through intramolecular interactions between the two distal coiled-coil domains. Deletion of these coiled-coil domains leads to a more active kinase, showing the negative autoregulatory role of these domains. The N-terminus-mediated dimerization and the intramolecular interaction between the distal coiled-coil domains are considered to be two mutually exclusive events, which regulate the catalytic state of MRCK kinases.

SUMMARY OF THE INVENTION

The present invention discloses compositions, organisms and methodologies employing a novel human protein kinase. The new human protein kinase shares sequence homology with rat MRCK alpha. The gene encoding the new protein is localized at 11q13.1 in human chromosome 11. This new gene is hereinafter referred to as the MRCK1 gene, and its encoded protein(s) is referred to as MRCK1 or MRCK1 kinase. MRCK1 has multiple domains including at least a kinase domain, a protein kinase C terminal domain, a myosin tail domain, a phorbol esters/diacylglycerol binding domain (DAG_PE binding domain), a Pleckstrin homology domain, a CNH domain, and a P21-Rho-binding domain. The sequence and structure similarity between MRCK1 and rat MRCK alpha indicates that MRCK1 may be involved in Cdc42-mediated cytoskeleton reorganization in human cells.

The kinase domain in MRCK1 shows 100% sequence alignment with the consensus sequences of the catalytic domains of at least two subfamilies of protein kinases. The utility of various kinase domains is known in the art. The utilities of other domains, such as protein kinase C terminal domains, Phorbol esters/diacylglycerol binding domains, Pleckstrin homology domains, CNH domains, and P21-Rho-binding domains are also known in the art. The unique peptide sequences, and nucleic acid sequences that encode the peptides, can be used as models for the development of human therapeutic targets, aid in the identification of therapeutic proteins, and serve as targets for the development of human therapeutic agents that modulate kinase activity in cells and tissues that express the kinase.

In one aspect, the invention provides isolated polynucleotides comprising a nucleotide sequence encoding MRCK1 or a variant of MRCK1.

In another aspect, the invention provides isolated polypeptides comprising the amino acid sequence of MRCK1 or a variant of MRCK1.

In yet another aspect, the invention provides agents that modulate expression levels of the MRCK1 gene or an activity of MRCK1.

The invention also provides methods for (a) detecting polynucleotides comprising a nucleotide sequence encoding MRCK1 or a variant of MRCK1 and (b) detecting polypeptides comprising an amino acid sequence of MRCK1 or a variant of MRCK1 in a biological sample.

The invention further provides methods for screening agents that modulate expression level of the MRCK1 gene or an activity of MRCK1.

The invention further provides cell lines harboring the MRCK1 gene, animals transgenic for the MRCK1 gene, and animals with interrupted MRCK1 gene (MRCK1 knockout animals). These cell lines and animals can be used to study the functions of MRCK1.

In still another aspect, the invention provides polynucleotides capable of inhibiting MRCK1 gene expression by RNA interference.

The invention further provides methods of inhibiting MRCK1 gene expression by introducing siRNAs or other RNAi sequences into target cells.

The preferred embodiments of the invention are described below in the Detailed Description of the Invention. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase.

It is further intended that the invention not be limited only to the specific structure, material or methods that are described in the preferred embodiments, but include any and all structures, materials or methods that perform the claimed function, along with any and all known or later-developed equivalent structures, materials or methods for performing the claimed function.

Further examples exist throughout the disclosure, and it is not applicant's intention to exclude from the scope of the invention the use of structures, materials, or methods that are not expressly identified in the specification, but nonetheless are capable of performing the claimed function.

BRIEF DESCRIPTION OF THE DRAWINGS

The inventions of this application are better understood in conjunction with the following drawings, in which:

FIG. 1 is the sequence alignment between a fragment of MRCK1 and its corresponding sequence in rat MRCK alpha.

FIG. 2 depicts the sequence alignment between another fragment of MRCK1 and its corresponding sequence in rat MRCK alpha.

FIG. 3 compares MRCK1 's kinase domain to the catalytic domain of a family of Ser/Thr protein kinases.

FIG. 4 compares MRCK1 's kinase domain to the kinase domain of another family of protein kinases.

FIG. 5 shows the sequence alignment between the kinase domain of MRCK1 and the catalytic domain of a family of tyrosine kinases.

FIG. 6 illustrates the sequence alignment between amino acid residues 339 to 398 of MRCK1 and the extension to Ser/Thr-type protein kinases FIG. 7 compares amino acid residues 339 to 398 of MRCK1 to a protein kinase C terminal domain.

FIG. 8 shows the sequence alignment between the amino acid residues 882-920 of MRCK1 and a consensus sequence of the DAG_PE bind domains of other proteins.

FIG. 9 depicts the sequence alignment between the amino acid residues 953-1060 of MRCK1 and a consensus sequence of the PH bind domains.

FIG. 10 illustrates the sequence alignment between the amino acid residues 954-1060 of MRCK1 and another consensus sequence of the PH bind domain.

FIG. 11 compares the amino acid residues 1102-1345 of MRCK1 to a consensus sequence of the CNH domains.

FIG. 12 shows the sequence alignment between the amino acid residues 1440-1471 of MRCK1 and a consensus sequence of the P21-Rho-binding domains.

FIG. 13 compares the amino acid residues 648-786 of MRCK1 to a consensus sequence of the myosin tail domains.

DETAILED DESCRIPTION OF THE INVENTION

Figure 14:
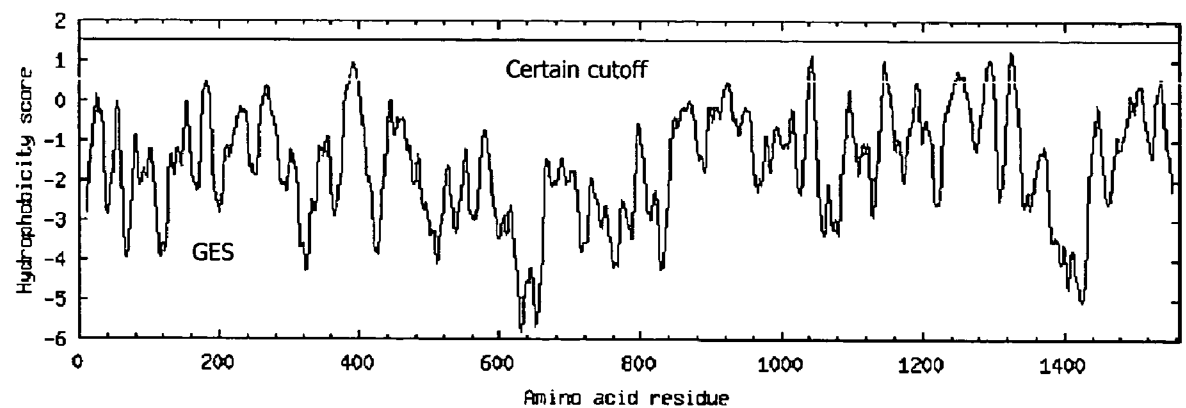
FIG. 14 shows the hydrophobicity profile of MRCK1.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

The present invention is based on the sequence information obtained from a newly-developed genomic prediction pipeline. Briefly, the X-ray crystal structures of the catalytic domains of protein kinases were collected and aligned together according to their structural identity/similarities. The alignment was converted into a "scoring matrix" which carried the structural profile of the kinase catalytic domains. This scoring matrix was then used to search the Celera Human Genome database and pull out sequences that have kinase catalytic domains.

Based on this analysis, the present invention provides the amino acid sequence of a human kinase peptide that is highly homologous to rat myotonic dystrophy kinase-related Cdc42 binding kinase (MRCK), cDNA sequences and genomic sequences that encode the kinase peptide, and information about the closest art known protein/peptide/domain that has structural or sequence homology to the kinase of the present invention.

In addition to being previously unknown, the peptide of the present invention is selected based on its ability to be used for the development of commercially important products and services. Specifically, the present peptides are selected based on homology to a known kinase protein of rat MRCK alpha.

Various aspects of the invention are described in detail in the following subsections. It should of course be understood that the use of subsections is not meant to limit the invention. Rather, each subsection applies to any aspect of the invention, as is appropriate.

Definitions and Terms

To facilitate the understanding of the present invention, a number of terms and phrases are defined below:

As used herein, a polynucleotide or a polypeptide is "isolated" if it is removed from its native environment. For instance, a polynucleotide or a polypeptide is isolated through a purification process such that the polynucleotide or polypeptide is substantially free of cellular material or free of chemical precursors. The polynucleotide/polypeptide of the present invention can be purified to homogeneity or other degrees of purity. The level of purification will be based on the intended use. As appreciated by one of ordinary skill in the art, a polynucleotide/polypeptide can perform its desired function(s) even in the presence of considerable amounts of other components or molecules.

In some uses, a polynucleotide/polypeptide that is "substantially free of cellular material" includes preparations which have less than about 30% (by weight) other polynucleotides/polypeptides including contaminating polynucleotides/polypeptides. For instance, the preparations can have less than about 20%, less than about 10%, or less than about 5% other polynucleotides/polypeptides. If a polynucleotide/polypeptide preparation is recombinantly produced, it can be substantially free of culture medium, i.e., culture medium components representing less than about 20% by weight of the polynucleotide/polypeptide preparation.

The language "substantially free of chemical precursors" includes preparations in which the polynucleotide/polypeptide is separated from chemical precursors or other chemicals that are involved in the synthesis of the polynucleotide/polypeptide. In one embodiment, the language "substantially free of chemical precursors" includes kinase preparations having less than about 30% (by weight), less than about 20% (by weight), less than about 10% (by weight), or less than about 5% (by weight) of chemical precursors or other chemicals used in the synthesis.

A "polynucleotide" can include any number of nucleotides. For instance, a polynucleotide can have at least 10, 20, 25, 30, 40, 50, 100 or more nucleotides. A polynucleotide can be DNA or RNA, double-stranded or single-stranded. A polynucleotide encodes a polypeptide if the polypeptide is capable of being transcribed and/or translated from the polynucleotide. Transcriptional and/or translational regulatory sequences, such as promoter and/or enhancer(s), can be added to the polynucleotide before said transcription and/or translation occurs. Moreover, if the polynucleotide is singled-stranded, the corresponding double-stranded DNA containing the original polynucleotide and its complementary sequence can be prepared before said transcription and/or translation.

As used herein, "a variant of a polynucleotide" refers to a polynucleotide that differs from the original polynucleotide by one or more substitutions, additions, and/or deletions. For instance, a variant of a polynucleotide can have 1, 2, 5, 10, 15, 20, 25 or more nucleotide substitutions, additions or deletions. Preferably, the modification(s) is in-frame, i.e., the modified polynucleotide can be transcribed and translated to the original or intended stop codon. If the original polynucleotide encodes a polypeptide with a biological activity, the polypeptide encoded by a variant of the original polynucleotide substantially retains such activity. Preferably, the biological activity is reduced/enhanced by less than 50%, or more preferably, less than 20%, relative to the original activity.

A variant of a polynucleotide can be a polynucleotide that is capable of hybridizing to the original polynucleotide, or the complementary sequence thereof, under reduced stringent conditions, preferably stringent conditions, or more preferably, highly stringent conditions. Examples of conditions of different stringency are listed in Table 1. Highly stringent conditions are those that are at least as stringent as conditions A-F; stringent conditions are at least as stringent as conditions G-L; and reduced stringency conditions are at least as stringent as conditions M-R. As used in Table 1, hybridization is carried out under a given hybridization condition for about 2 hours, followed by two 15-minute washes under the corresponding washing condition(s).

TABLE 1

Stringency Conditions

| Stringency Condition | Polynucleotide Hybrid | Hybrid Length (bp)[1] | Hybridization Temperature and Buffer[H] | Wash Temp. and Buffer[H] |
|---|---|---|---|---|
| A | DNA:DNA | >50 | 65° C.; 1 × SSC -or- 42° C.; 1 × SSC, 50% formamide | 65° C.; 0.3 × SSC |
| B | DNA:DNA | <50 | $T_B$*; 1 × SSC | $T_B$*; 1 × SSC |
| C | DNA:RNA | >50 | 67° C.; 1 × SSC -or- 45° C.; 1 × SSC, 50% formamide | 67° C.; 0.3 × SSC |
| D | DNA:RNA | <50 | $T_D$*; 1 × SSC | $T_D$*; 1 × SSC |
| E | RNA:RNA | >50 | 70° C.; 1 × SSC -or- 50° C.; 1 × SSC, 50% formamide | 70° C.; 0.3 × SSC |
| F | RNA:RNA | <50 | $T_F$*; 1 × SSC | $T_F$*; 1 × SSC |
| G | DNA:DNA | >50 | 65° C.; 4 × SSC -or- 42° C.; 4 × SSC, 50% formamide | 65° C.; 1 × SSC |
| H | DNA:DNA | <50 | $T_H$*; 4 × SSC | $T_H$*; 4 × SSC |
| I | DNA:RNA | >50 | 67° C.; 4 × SSC -or- 45° C.; 4 × SSC, 50% formamide | 67° C.; 1 × SSC |
| J | DNA:RNA | <50 | $T_J$*; 4 × SSC | $T_J$*; 4 × SSC |
| K | RNA:RNA | >50 | 70° C.; 4 × SSC -or- 50° C.; 4 × SSC, 50% formamide | 67° C.; 1 × SSC |
| L | RNA:RNA | <50 | $T_L$*; 2 × SSC | $T_L$*; 2 × SSC |
| M | DNA:DNA | >50 | 50° C.; 4 × SSC -or- 40° C.; 6 × SSC, 50% formamide | 50° C.; 2 × SSC |
| N | DNA:DNA | <50 | $T_N$*; 6 × SSC | $T_N$*; 6 × SSC |
| O | DNA:RNA | >50 | 55° C.; 4 × SSC -or- 42° C.; 6 × SSC, 50% formamide | 55° C.; 2 × SSC |
| P | DNA:RNA | <50 | $T_P$*; 6 × SSC | $T_P$*; 6 × SSC |
| Q | RNA:RNA | >50 | 60° C.; 4 × SSC -or- 45° C.; 6 × SSC, 50% formamide | 60° C.; 2 × SSC |
| R | RNA:RNA | <50 | $T_R$*; 4 × SSC | $T_R$*; 4 × SSC |

[1]The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.

[H]SSPE (1 × SSPE is 0.15 M NaCl, 10 mM $NaH_2PO_4$, and 1.25 mM EDTA, pH 7.4) can be substituted for SSC (1 × SSC is 0.15 M NaCl and 15 mM sodium citrate) in the hybridization and wash buffers.

$T_B$*-$T_R$*: The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.) = 2 (# of A + T bases) + 4(# of G + C bases). For hybrids between 18 and 49base pairs in length, $T_m$(° C.) = 81.5 + 16.6 ($\log_{10}Na^+$) + 0.41 (% G + C) − (600/N), where N is the number of bases in the hybrid, and $Na^+$ is the concentration of sodium ions in the hybridization buffer ($Na^+$ for 1 × SSC = 0.165 M).

It will be appreciated by those of ordinary skill in the art that, as a result of the degeneracy of the genetic code, there are many polynucleotide variants that encode the same polypeptide. Some of these polynucleotide variants bear minimal sequence homology to the original polynucleotide. Nonetheless, polynucleotides that vary due to differences in codon usage are specifically contemplated by the present invention.

As used herein, a "polypeptide" can include any number of amino acid residues. For instance, a polypeptide can have at least 5, 10, 15, 20, 30, 40, 50 or more amino acid residues.

As used herein, a "variant of a polypeptide" is a polypeptide that differs from the original polypeptide by one or more substitutions, deletions, and/or insertions. Preferably, these modifications do not substantially change (e.g. reduce or enhance) the original biological function of the polypeptide. For instance, a variant can reduce or enhance or maintain the biological activities of the original polypeptide. Preferably, the biological activities of the variant are reduced or enhanced by less than 50%, or more preferably, less than 20%, relative to the original polypeptide.

Similarly, the ability of a variant to react with antigen-specific antisera can be enhanced or reduced by less than 50%, preferably less than 20%, relative to the original polypeptide. These variants can be prepared and evaluated by modifying the original polypeptide sequence and then determining the reactivity of the modified polypeptide with the antigen-specific antibodies or antisera.

Preferably, a variant polypeptide contains one or more conservative substitutions. A "conservative substitution" is one in which an amino acid is substituted for another amino acid which has similar properties, such that one skilled in the art would expect that the secondary structure and hydropathic nature of the substituted polypeptide will not be substantially changed. Conservative amino acid substitutions can be made on the basis of similarity in polarity, charge, solubility, hydrophobicity, hydrophilicity and/or the amphipathic nature of the residues. Negatively charged amino acids include aspartic acid and glutamic acid, and positively charged amino acids include lysine and arginine. Amino acids having uncharged polar head groups and similar hydrophilicity values include leucine, isoleucine and valine, or glycine and alanine, or asparagine and glutamine, or serine, threonine, phenylalanine and tyrosine. Other groups of amino acids that can produce conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A polypeptide variant can also contain nonconservative changes.

Polypeptide variants can be prepared by the deletion and/or addition of amino acids that have minimal influence on the biological activity, immunogenicity, secondary structure and/or hydropathic nature of the polypeptide. Variants can be for instance by substituting, modifying, deleting or adding one or more amino acids residues in the original sequence. Polypeptide variants preferably exhibit at least 96%, more preferably at least 97%, and most preferably at least 98% sequence homology to the original polypeptide.

Polypeptide variants include polypeptides that are modified from the original polypeptides either by a natural process, such as a post-translational modification, or by a chemical modification. These modifications are well-known in the art. Modifications can occur anywhere in the polypeptide, including the backbone, the amino acid side-chains and the amino or carboxyl termini. It will be appreciated that the same type of modification can be present in the same or varying degrees at several sites in a given polypeptide. Also, a given polypeptide can contain many types of modifications. Polypeptides may be branched, for example, as a result of ubiquitination, and they may be cyclic, with or without branching. Cyclic, branched, and branched cyclic polypeptides can result from natural post-translational processes or be made through synthetic methods. Suitable modifications for this invention include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

As used herein, the term "modulation" includes up-regulation, induction, stimulation, potentiation, inhibition, down-regulation or suppression, or relief of inhibition.

A nucleotide sequence is "operably linked" to another nucleotide sequence if the two sequences are placed into a functional relationship. For example, a coding sequence is operably linked to a 5' regulatory sequence if the 5' regulatory sequence can initiate transcription of the coding sequence in an in vitro transcription/translation system or in a host cell. "Operably linked" does not require that the DNA sequences being linked are contiguous to each other. Intervening sequences may exist between two operably linked sequences.

As used herein, a "disease-free" human refers to a human who does not have MRCK1-related diseases. Disease-free, tissues or samples refer to cells, tissues or samples obtained from disease-free human(s).

A polynucleotide is "capable of hybridizing" to a gene if the polynucleotide can hybridize to at least one of the following sequences: (1) the sequence of an RNA transcript of the gene, (2) the complementary sequence of an RNA transcript of the gene, (3) the cDNA sequence of an RNA transcript of the gene, (4) the complementary sequence of the cDNA sequence of an RNA transcript of the gene, (5) a genomic sequence of the gene, and (6) the complementary sequence of a genomic sequence of the gene.

As used herein, sequence "identity" or "percentage alignment" in an alignment can be determined by the standard protein-protein or nucleotide-nucleotide BLAST programs (i.e., blastp or blastn, respectively). Sequence identity can also be determined by the BLAST2 program. Suitable BLAST program can be found at the BLAST web site maintained by the National Center of Biotechnology Information (NCBI) (National Library of Medicine)

Human MRCK1 Gene and MRCK1 Kinase

The present invention identifies a new human gene (MRCK1 gene) that encodes a protein that is highly homologous to rat MRCK alpha. The nucleotide and amino acid sequences of the protein encoded by the MRCK1 gene are depicted in SEQ ID NOS:1 and 2, respectively. FIGS. 1 and 2 show the sequence alignment between SEQ ID NO:2 (denoted as "Query") and the amino acid sequence of rat MRCK alpha (denoted as "Sbjct"). The alignment is a result of blast search of the "all non-redundant GenBank CDS database" in Entrez. The blast search uses BLASTP 2.2.3 algorithm [Apr. 24, 2002], which is described in Altschul et al., Nucleic Acids Res., 25: 3389-3402 (1997).

FIG. 1 shows that the sequence consisting of amino acid residues 40 to 434 of MRCK1 (Query) and the sequence consisting of amino acid residues 46 to 463 of rat MRCK alpha (Sbjct) have 65% sequence identity with 78% positives, a score of 588 bits (1516) and an E value of $1\times10^{-172}$. FIG. 2 shows that the sequence consisting of amino acid residues 551 to 1457 of MRCK1 (Query) and the sequence consisting of amino acid residues 684 to 1588 of rat MRCK alpha (Sbjct) have 38% sequence identity with 54% positives, a score of 615 bits (1586) and an E value of $1\times10^{-166}$. The rat MRCK alpha sequence used in the alignment has Entrez Database accession number AAC02941.1 or NP_446109.1.

The same approach is used to compare MRCK1 to a predicted mouse protein, which is similar to Ser/Thr protein kinase related to the myotonic dystrophy protein kinase. The sequence of the mouse protein has Entrez Database accession number XP_140553.1. Alignment shows that amino acid residues 40 to 1574 of the mouse sequence (Sbjct) and the sequence consisting of amino acid residues 40 to 1548 of MRCK1 (Query) have 70% sequence identity with 73% positives, a score of 1981 bits (5133) and an E value of 0.0.

The same blast search also identifies sequence similarity between MRCK1 and other proteins. These proteins include, but are not limited to, human Cdc42-binding protein kinase beta (Entrez accession number: NM_006035) and *C. elegans* serine/threonine-protein kinase (Entrez accession number: NM_072198).

In addition, the kinase domain of MRCK1 (including amino acid residues 77 to 337, see below) has sequence homology to the catalytic domains of various protein kinases. These protein kinases include, but are not limited to, human myotonic dystrophy kinase (Entrez accession number: AAC14450.1 or L08835, 62% sequence identity), human dystrophia myotonica-protein (Entrez accession number: NM_004409, 61% sequence identity), human myotonin-protein kinase, Form VI (Entrez accession number: AAA75239.1 or L00727, 62% sequence identity), and human myotonin-protein kinase, Form VIII (Entrez accession number: AAA75237.1 or L00727, 62% sequence identity).

The sequence consisting of amino acid residues 113 to 399 of MRCK1 (Query) also alignsto the amino acid sequence having Entrez Protein Database accession number CAA73006.1 (Sbjct). These two sequences are 100% identical to each other. Sequence CAA73006.01 was disclosed in Kedra et al., Hum. Genet. 100: 611-619 (1997), and is localized to 11q13 in human chromosome 11.

MRCK1 gene is also localized near or at 11q13 in human chromosome 11. Specifically, the MRCK1 gene is located between genes LOC256612 and EHD1, and overlaps with gene LOC196205. The MRCK1 gene encompasses nucleotides 979139 to 999235 in human chromosome 11. The nucleotide numbering in human chromosome 11 is based on Entrez Human Genome Sequence Database maintained by NCBI. The minus-strand sequence of human chromosome 11 that consists of nucleotides 979139 to 999235 is shown in SEQ ID NO:3. The genomic sequence in SEQ ID NO:3 is listed from 5' to 3', i.e. from nucleotide 999235 to nucleotide 979139 in the minus strand of human chromosome 11.

Human chromosome loci near or at 11q13 harbor multiple disease-related genes. These diseases include insulin-dependent diabetes mellitus, familial paraganglioma type 2, spinocerebellar ataxia type 5, Bardet-Biedl syndrome, and multiple endocrine neoplasia type 1. In addition, there is a report of a translocation, t(11;17), at this loci in B-cell non-Hodgkin's lymphoma.

Human MRCK1 gene has at least 35 exons. Table 2 lists the location of each of these 35 exons in the genomic sequence SEQ ID NO:3. SEQ ID NO:1 shows an MRCK1-coding sequence produced by fusing the 35 exons in consecutive order. Translation of SEQ ID NO:1 produces the amino acid sequence SEQ ID NO:2. Table 2 also illustrates the corresponding location of each exon in the MRCK1-coding sequence SEQ ID NO:1.

TABLE 2

Exons in Human MRCK1 Gene

| Exon Numbers | Corresponding Sequence in SEQ ID NO: 3 Comprised in Human Chromosome 11 | Corresponding Sequence in SEQ ID NO: 1 |
|---|---|---|
| 1 | 1-160 | 1-160 |
| 2 | 2,666-2,757 | 161-252 |
| 3 | 2,837-2,920 | 253-336 |
| 4 | 3,922-4,017 | 337-432 |
| 5 | 4,302-4,450 | 433-581 |
| 6 | 4,999-5,092 | 582-675 |
| 7 | 5,337-5,537 | 676-876 |
| 8 | 5,668-5,916 | 877-1,125 |
| 9 | 6,408-6,487 | 1,126-1,205 |
| 10 | 7,551-7,648 | 1,206-1,303 |
| 11 | 7,692-7,831 | 1,304-1,443 |
| 12 | 8,276-8,455 | 1,444-1,623 |
| 13 | 8,721-8,810 | 1,624-1,713 |
| 14 | 8,951-9,072 | 1,714-1,835 |
| 15 | 9,153-9,225 | 1,836-1,908 |
| 16 | 9,419-9,525 | 1,909-2,015 |
| 17 | 9,609-9,723 | 2,016-2,130 |
| 18 | 9,995-10,143 | 2,131-2,279 |
| 19 | 10,218-10,306 | 2,280-2,368 |
| 20 | 10,595-10,647 | 2,369-2,421 |
| 21 | 10,736-10,834 | 2,422-2,520 |
| 22 | 10,913-10,972 | 2,521-2,580 |
| 23 | 11,182-11,341 | 2,581-2,740 |
| 24 | 11,613-11,746 | 2,741-2,874 |
| 25 | 11,829-11,968 | 2,875-3,014 |
| 26 | 12,063-12,144 | 3,015-3,096 |
| 27 | 12,851-13,067 | 3,097-3,313 |
| 28 | 14,317-14,379 | 3,314-3,376 |
| 29 | 14,503-15,102 | 3,377-3,976 |
| 30 | 16,786-16,883 | 3,977-4,074 |
| 31 | 16,958-17,042 | 4,075-4,159 |
| 32 | 17,171-17,291 | 4,160-4,280 |
| 33 | 17,402-17,519 | 4,281-4,398 |

TABLE 2-continued

Exons in Human MRCK1 Gene

| Exon Numbers | Corresponding Sequence in SEQ ID NO: 3 Comprised in Human Chromosome 11 | Corresponding Sequence in SEQ ID NO: 1 |
|---|---|---|
| 34 | 17,857-18,099 | 4,399-4,641 |
| 35 | 20,041-20,097 | 4,642-4,698 |

MRCK1 kinase depicted by SEQ ID NO:2 comprises multiple structural/functional domains. These structural/functional domains include at least a kinase domain (comprising amino acid residues 71 to 337), a protein kinase C terminal domain (comprising amino acid residues 339 to 398), a myosin tail domain (comprising amino acid residue 648 to 786), a DAG_PE binding domain (comprising amino acid residues 882 to 920), a Pleckstrin homology domain (comprising amino acid residues 953 to 1060), a CNH domain (comprising amino acid residues 1102 to 1345), and a P21-Rho-binding domain (comprising amino acid residues 1440 to 1471).

FIGS. 3, 4, and 5 illustrate the sequence alignments between MRCK1's kinase domain and various protein kinase domains. As used in other figures of this invention, "Query" denotes to the sequence of MRCK1, and "Sbjct" refers to the sequence being compared to the MRCK1 sequence.

FIG. 3 is the alignment between MRCK1's kinase domain and the consensus sequence of the catalytic domains of a subfamily of Serine/Threonine protein kinases. This subfamily includes C-Jun N-terminal kinase (JNK3), abelson tyrosine kinase, a calmodulin-binding, vesicle-associated, protein kinase-like protein (1 G5), serine/threonine-protein kinase prp4, Cdc2/Cdc28 subfamily of Ser/Thr protein kinases in *Caenorhabditis elegans*, and ribosomal S6 kinase of *C. elegans*. The consensus sequence has CD NO: smart00220.4, S_TKc, and can be retrieved from the Conserved Domain Database maintained by NCBI. The alignment was performed using standard protein-protein BLAST (blastp) algorithm provided by NCBI. MRCK1 's kinase domain has 100% sequence identities to the consensus sequence smart00220.4, with a score of 263 bits and an E value of $3\times10^{-71}$.

FIG. 4 shows the alignment between MRCK1 's kinase domain and the consensus sequence of the catalytic domains of another subfamily of protein kinases. This subfamily includes protein kinase Ck2, weel-like protein kinase (WEElhu), and tyrosine-protein kinase RYK. The consensus sequence has CD NO: pfam00069.4, pkinase. MRCK1 's kinase domain has 100% sequence identities to pfam00069.4, with a score of 213 bits and an E value of $2\times10^{-56}$.

FIG. 5 shows the alignment between MRCK1 's kinase domain and the catalytic domain (CD NO: smart00219.4, TyrKc) of a subfamily of tyrosine kinases. This subfamily includes the tyrosine kinase domain of fibroblast growth factor receptor 1, tyrosine-protein kinase (KIN15/KIN16 subfamily), and a Drosophila receptor protein-tyrosine kinase family member (dr1-P1). The amino acid residues 72-303 in MRCK1 's kinase domain has 89.1% sequence identities to smart00219.4, with a score of 112 bits and an E value of $9\times10^{-26}$.

FIG. 6 illustrates the sequence alignment between the amino acid residues 339-398 of MRCK1 and the consensus sequence for the extension to a family of Ser/Thr-type protein kinases. The consensus sequence has CD NO: smart00133.4, S_TK_X. This family of protein kinases includes cAMP-Dependent protein kinase, protein kinase cek1, and cell cycle protein kinase DBF2. The two sequences share 95.2% sequence identities with a score of 57.7 bits and an E value of $3\times10^{-9}$.

The amino acid residues 339-398 of MRCK1 further aligned to a consensus sequence (CD NO: pfam00433.4, pkinase_C) of the protein kinase C terminal domain. FIG. 7 shows 91% sequence identities between these two sequences. The alignment has a score of 40.6 bits and an E value of 4×10-° 4. Ribosomal protein S6 kinase (S6K), serine/threonine-protein kinase YPK1, and protein kinase C, zeta type (NPKC-ZETA) share the consensus sequence pfam00433.4, pkinase_C.

FIG. 8 demonstrates the sequence alignment between the amino acid residues 882-920 and a consensus sequence of the DAG_PE binding domains. The two sequences show 78% sequence identities with a score of 51.9 bits and an E value of $2\times10^{-07}$. The CD number for the consensus sequence is pfam00130.4. The DAG_PE binding domain is also known as the protein kinase C conserved region 1 (C1 or cysteine-rich) domain.

In addition, MRCK1 shows sequence homology to the Pleckstrin homology domain (PH domain). PH domains are commonly found in eukaryotic signaling proteins. The domain family possesses multiple functions including the abilities to bind inositol phosphates and various other proteins. PH domains have been found to possess inserted domains (such as in PLC gamma, syntrophins) and/or to be inserted within other domains. Mutations in Brutons tyrosine kinase (Btk) within its PH domain cause X-linked agammaglobulinaemia (XLA) in patients.

FIG. 9 shows the comparison of the amino acid residues 953-1060 of MRCK to the consensus sequence of the PH domains of a family of proteins which include Rac1 and GTPase activating protein BEM2/IPL2. The consensus sequence has CD NO: smart00233.4, PH. The comparison indicates 87.5% sequence identities with a score of 47.8 bits and an E value of $2\times10^{-6}$.

FIG. 10 depicts the comparison between the amino acid residues 954-1060 of MRCK1 and another consensus sequence of the PH domains. The consensus sequence has CD NO: pfam00169.4, PH, which is shared by proteins including Still life protein type 1 (SIF type 1) and *C. elegans* LET-502 protein. The comparison shows 88% sequence identities with a score of 42.6 bits and an E value of $9\times10^{-5}$.

FIG. 11 shows the comparison between the amino acid residues 1102-1345 of MRCK1 and a consensus CNH domain sequence (CD NO: pfam00780.4, CNH). The alignment shows 85.7% sequence identities with a score of 60.0 bits and an E value of $6\times10^{-10}$. The consensus CNH domain sequence is found in NIK1-like kinase, mouse citron (Rho-interacting, serine/threonine kinase 21), and yeast ROM 1 and ROM2.

FIG. 12 shows the sequence alignment between the amino acid residues 1440-1475 of MRCK1 and the consensus sequence of other P21-Rho-binding domain (CD NO: smart00285, PBD). The two sequences have 86.1% sequence identities with a score of 38.3 bits and an E value of 0.002. P21-Rho-binding domain is a domain that binds Cdc42p-and/or Rho-like small GTPases. The domain also knows as the Cdc42/Rac interactive binding domain (CRIB domain).

The amino acid residues 648 to 786 in MRCK1 also weakly resemble a myosin tail domain (CD NO: pfam01576). The myosin molecule is a multi-subunit complex made up of two heavy chains and four light chains. It is a fundamental contractile protein found in all eukaryotic cell types. The myosin tail domain consists of the coiled-coil myosin heavy chain tail region. The coiled-coil is composed of the tail from two molecules of myosin. These can then assemble into the macromolecular thick filament. The coiled-coil region provides the structural backbone the thick filament. The alignment shows in FIG. 13. The two sequences being compared have 17.8% sequence identities with a score of 39.9 bits and an E value of $7\times10^{-4}$.

The MCRK1 sequence also shows high homology to PKIN20, a human kinase disclosed in PCT patent application No. WO 02/08399. The two proteins share 90% sequence identities in amino acids and 95% identities at the cDNA level.

Hydrophobicity analysis indicates that MRCK1 kinase is not likely a membrane or transmembrane protein. The hydrophobicity profile of MRCK1 is illustrated in FIG. 14.

The existence and expression of the MRCK1 gene in humans are supported by various EST sequences. For instance, nucleotides 289-1205 of SEQ ID NO:1 are supported by the EST sequence disclosed under GenBank accession number BF994269; nucleotides 2449-2798 of SEQ ID NO:1 are supported by the EST sequences disclosed under GenBank accession numbers BF869661, BF357216, BF357213, BG952299, and BG014499; nucleotides 3042-3313 of SEQ ID NO:1 are supported by the EST sequence disclosed under GenBank accession number BF991223; nucleotides 4043-4403 of SEQ ID NO:1 are supported by the EST sequences disclosed under GenBank accession numbers BE793390, BG752641, and AW814108; nucleotides 4398-4440 of SEQ ID NO:1 are supported by the EST sequences disclosed under GenBank accession numbers BG752641, AW516225, BE793390, B1792977, and B1793270; nucleotides 4556-4698 of SEQ ID NO:1 are supported by the EST sequences disclosed under GenBank accession numbers BG752641, B1793270, BE793390, AW516225, B1792977, and AA809737.

Two transcripts of MRCK1, a 4 kb and a 6 kb transcript, were detected in human brain, heart, skeletal muscle, colon, thymus, spleen, kidney, liver, small intestine, placenta, lung, and peripheral blood leukocyte by Multiple Tissue Northern analysis (MTN). The highest expression was in placenta while the lowest expression was in small intestine. The MRCK1 expression was confirmed by an multiple tissue expression array (MTA), in which MRCK1 expression was found in all 76 tissues contained in the array.

Utility of Protein Kinases

Protein kinases are involved in the regulation of many critical biological processes such as signal transduction pathways. Malfunctions of cellular signaling have been associated with many diseases. Regulation of signal transduction by cytokines and association of signal molecules with protooncogenes and tumor suppressor genes have been the subjects of intense research. Many therapeutic strategies can now be developed through the synthesis of compounds which activate or inactivate protein kinases.

The importance of kinases in the etiology of diseases has been well established. Kinase proteins are a major target for drug action and development. A January 2002 survey of ongoing clinical trials in the USA revealed more than 100 clinical trials involving the modulation of kinases. Trials are ongoing in a wide variety of therapeutic indications including asthma, Parkinson's, inflammation, psoriasis, rheumatoid arthritis, spinal cord injuries, muscle conditions, osteoporosis, graft versus host disease, cardiovascular disorders, autoimmune disorders, retinal detachment, stroke, epilepsy, ischemia/reperfusion, breast cancer, ovarian cancer, glioblastoma, non-Hodgkin's lymphoma, colorectal cancer, non-small cell lung cancer, brain cancer, Kaposi's sarcoma, pancreatic cancer, liver cancer, and other tumors. Numerous kinds of modulators of kinase activity are currently in clinical trials including antisense molecules, antibodies, small molecules, and even gene therapy. Accordingly, it is valuable to the field of pharmaceutical development to identify and characterize previously unknown members of the kinase family proteins. The present invention advances the state of the art by providing novel human kinase proteins which are structurally related to MRCKs.

Many therapeutic strategies are aimed at critical components in signal transduction pathways. Approaches for regulating kinase gene expression include specific antisense oligonucleotides for inhibiting post-transcriptional processing of the messenger RNA, naturally occurring products and their chemical derivatives to inhibit kinase activity and monoclonal antibodies to inhibit receptor linked kinases. In some cases, kinase inhibitors also allow other therapeutic agents additional time to become effective and act synergistically with current treatments.

Among the areas of pharmaceutical research that are currently receiving a great deal of attention are the role of phosphorylation in transcriptional control, apoptosis, protein degradation, nuclear import and export, cytoskeletal regulation, and checkpoint signaling. The accumulating knowledge about signaling networks and the proteins involved will be put to practical use in the development of potent and specific pharmacological modulators of phosphorylation-dependent signaling. The rational structure-based design and development of highly specific kinase modulators is becoming routine and drugs that intercede in signaling pathways are becoming a major class of drug. The functions of some of the kinases are described below.

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intra-cellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease.

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR. CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues, such as brain, heart, spleen, and lung, than expected. This distribution suggests that AMPK's functions may extend beyond regulation of lipid metabolism alone.

The mitogen-activated protein kinases (MAP) are also members of the STK family. MAP kinases also regulate intra-cellular signaling pathways. They mediate signal transduction from the cell surface to the nucleus via phosphorylation cascades. Several subgroups have been identified, and each manifests different substrate specificities and responds to distinct extracellular stimuli. MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines, such as tumor necrosis factor (TNF) and interleukin-1 (IL-1).

EGF receptor is found in over half of breast tumors unresponsive to hormone. EGF is found in many tumors, and EGF may be required for tumor cell growth. Antibody to EGF blocked the growth of tumor xenografts in mice. An antisense oligonucleotide for amphiregulin inhibited growth of a pancreatic cancer cell line.

Tamoxifen, a protein kinase C inhibitor with anti-estrogen activity, is currently a standard treatment for hormone-dependent breast cancer. The use of this compound may increase the risk of developing cancer in other tissues such as the endometrium. Raloxifene, a related compound, has been shown to protect against osteoporosis. The tissue specificity of inhibitors must be considered when identifying therapeutic targets.

Signal transduction to the nucleus in response to extracellular stimulus by a growth factor involves the mitogen activated protein (MAP) kinases. MAP kinases are a family of protein serine/threonine kinases which mediate signal transduction from extracellular receptors or heat shock, or UV radiation. Cell proliferation and differentiation in normal cells are under the regulation and control of multiple MAP kinase cascades. Aberrant and deregulated functioning of MAP kinases can initiate and support carcinogenesis. Insulin and IGF—1 also activate a mitogenic MAP kinase pathway that may be important in acquired insulin resistance occurring in type 2 diabetes.

Many cancers become refractory to chemotherapy by developing a survival strategy involving the constitutive activation of the phosphatidylinositol 3-kinase-protein kinase B/Akt signaling cascade. This survival signaling pathway thus becomes an important target for the development of specific inhibitors that would block its function. PI-3 kinase/Akt signaling is equally important in diabetes. The pathway activated by RTKs subsequently regulates glycogen synthase 3 (GSK3) and glucose uptake. Since AKT has decreased activity in type 2 diabetes, it provides a therapeutic target.

Protein kinase inhibitors provide much of our knowledge about in vivo regulation and coordination of physiological functions of endogenous peptide inhibitors. A pseudosubstrate sequence within PKC acts to inhibit the kinase in the absence of its lipid activator. A PKC inhibitor, such as chelerythrine, acts on the catalytic domain to block substrate interaction, while calphostin acts on the regulatory domain to mimic the pseudosubstrate sequence and block ATPase activity, or to inhibit cofactor binding.

Although some protein kinases have, to date, no known system of physiological regulation, many are activated or inactivated by autophosphorylation or phosphorylation by upstream protein kinases. The regulation of protein kinases also occurs during the transcription, post-transcription, and post-translation processes. The mechanism of post-transcriptional regulation is alternative splicing of precursor mRNA. For example, protein kinase C βI and βII are two isoforms of a single PKCβ gene derived from differences in the splicing of the exon encoding the C-terminal 50-52 amino acids. Splicing can be regulated by a kinase cascade in response to peptide hormones, such as insulin and IGF-1. PKC βI and βII have different specificities for phosphorylating members of the mitogen activated protein (MAP) kinase family, for glycogen synthase 3β, for nuclear transcription factors, such as TLS/Fus, and for other nuclear kinases. By inhibiting the post-transcriptional alternative splicing of PKC βII mRNA, PKC βII-dependent processes are inhibited.

The development of antisense oligonucleotides to inhibit the expression of various protein kinases has been successful. Antisense oligonucleotides are short lengths of synthetically manufactured, chemically modified DNA or RNA designed to specifically interact with mRNA transcripts encoding target proteins. The interaction of the antisense moiety with mRNA inhibits protein translation and, in some cases, post-transcriptional processing (e.g., alternative splicing and stability) of mRNA. Antisense oligonucleotides have been developed to alter alternative splicing of mRNA forms for inhibiting the translation of PKCα.

Protein kinase C isoforms have been implicated in cellular changes observed in the vascular complications of diabetes. Hyperglycemia is associated with increased levels of PKCα and β isoforms in renal glomeruli of diabetic rats. Oral administration of a PKCβ inhibitor prevented the increased mRNA expression of TGF-β1 and extracellular matrix component genes. Administration of the specific PKCβ inhibitor (LY333531) also normalized levels of cytokines, caldesmon, and hemodynamics of retinal and renal blood flow. Overexpression of the PKCβ isoform in the myocardium resulted in cardiac hypertrophy and failure. The use of LY333531 to prevent adverse effects of cardiac PKCβ overexpression in diabetic subjects is under investigation. The compound is also in Phase I/II clinical trials for diabetic retinopathy and diabetic macular edema indicating that it may be pharmacodynamically active.

PRK (proliferation-related kinase) is a serum/cytokine inducible STK that is involved in regulation of the cell cycle and cell proliferation in human megakaroytic cells. PRK is related to the polo (derived from humans polo gene) family of STKs implicated in cell division. PRK is down-regulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

DNA-dependent protein kinase (DNA-PK) is involved in the repair of double-strand breaks in mammalian cells. This enzyme requires ends of double-stranded DNA or transitions from single-stranded to double-stranded DNA in order to act as a serine/threonine kinase. Cells with defective or deficient DNA-PK activity are unable to repair radiation induced DNA double-strand breaks and are consequently very sensitive to the lethal effects of ionizing radiation. Inhibition of DNA-PK has the potential to increase the efficacy of antitumor treatment with radiation or chemotherapeutic agents.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Cellular inhibitors of CDKs also play a major role in cell cycle progression. Alterations in the expression, function, and structure of cyclin and CDK are encountered in the cancer phenotype. Therefore CDKs may be important targets for new cancer therapeutic agents.

Chemotherapy resistant cells tend to escape apoptosis. Under certain circumstances, inappropriate CDK activation may even promote apoptosis by encouraging the progression of the cell cycle under unfavorable conditions, i.e., attempting mitosis while DNA damage is largely unrepaired.

Purines and purine analogs act as CDK inhibitors. Flavopiridol is a flavonoid that causes 50% growth inhibition of tumor cells at 60 nM. It also inhibits EGFR and protein kinase A. Flavopiridel induces apoptosis and inhibits lymphoid, myeloid, colon, and prostate cancer cells grown in vivo as tumor xenografts in nude mice.

Staurosporine and its derivative, UCN-01, in addition to inhibiting protein kinase C, inhibit cyclin B/CDK ($IC_{50}$=3 to 6 nM). Staurosporine is toxic, but its derivative 7-hydroxystaurosporine (UCN-01) has anti-tumor properties and is in clinical trials. UCN-01 affects the phosphorylation of CDKs and alters the cell cycle checkpoint functioning. These compounds illustrate that multiple intra-cellular targets may be affected as the concentration of an inhibitor is increased within cells.

Protein tyrosine kinases, PTKs, specifically phosphorylate tyrosine residues on their target proteins and may be divided into transmembrane, receptor PTKs and non-transmembrane, non-receptor PTKs. Transmembrane protein tyrosine kinases are receptors for most growth factors. Binding of a growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Since RTKs stimulate tumor cell proliferation, inhibitors of RTKs may inhibit the growth and proliferation of such cancers. Inhibitors of RTKs are also useful in preventing tumor angiogenesis and can eliminate support from the host tissue by targeting RTKs located on vascular cells, such as blood vessel endothelial cells and stromal fibroblasts. For example, VEGF stimulates endothelial cell growth during angiogenesis, and increases the permeability of tumor vasculature so that proteins and other growth factors become accessible to the tumor. Broad-spectrum antitumor efficacy of an oral dosage form of an inhibitor of VEGF signaling has been reported. Thus, inhibition of VEGF receptor signaling presents an important therapeutic target. An extracellular receptor can also be a target for inhibition. For example, the EGF receptor family and its ligands are overexpressed and exist as an autocrine loop in many tumor types.

Increasing knowledge of the structure and activation mechanism of RTKs and the signaling pathways controlled by tyrosine kinases provided the possibility for the development of target specific drugs and new anti-cancer therapies. Approaches towards the prevention or interception of deregulated RTK signaling include the development of selective components that target either the extracellular ligand-binding domain or the intra-cellular substrate binding region.

The most successful strategy to selectively kill tumor cells is the use of monoclonal antibodies (mAbs) that are directed against the extracellular domain of RTKs which are critically involved in cancer and are expressed at the surface of tumor cells. In the past years, recombinant antibody technology has made an enormous progress in the design, selection and production of newly engineered antibodies. It is also possible to generate humanized antibodies, human-mouse chimeric or bispecific antibodies for targeted cancer therapy. Mechanistically, anti-RTK mAbs might work by blocking the ligand-receptor interaction and therefore inhibiting ligand-induced RTK signaling and increasing RTK down-regulation and internalization. In addition, binding of mAbs to certain epitopes on the cancer cells may induce immune-mediated responses, such as opsonization and complement-mediated lysis, and trigger antibody-dependent cellular cytotoxicity by macrophages or natural killer cells. In recent years, it became evident that mAbs control tumor growth by altering the intra-cellular signaling pattern inside the targeted tumor cell, leading to growth inhibition and/or apoptosis. In addition, bispecific antibodies can bridge selected surface molecules on a target cell with receptors on an effector cell, thus triggering cytotoxic responses against the target cell. Despite the toxicity that has been seen in clinical trials of bispecific antibodies, advances in antibody engineering, characterization of tumor antigens and immunology might help to produce rationally designed bispecific antibodies for anti-cancer therapy.

Another promising approach to inhibiting aberrant RTK signaling is to develop small molecule drugs that selectively interfere with the intrinsic tyrosine kinase activity and thereby block receptor autophosphorylation and activation of downstream signal transducers. The tyrphostins, which belong to the quinazolines, are one important group of such inhibitors that compete with ATP for the ATP binding site at the receptor's tyrosine kinase domain and some members of the group have been shown to specifically inhibit the EGFR. Potent and selective inhibitors of receptors involved in neovascularization have been developed and are now undergoing clinical evaluation. New classes of tyrosine kinase inhibitors (TKIs) with increased potency and selectivity, higher in vitro and in vivo efficacy and decreased toxicity have been developed using the advantages of structure-based drug design, crystallographic structure information, combinatorial chemistry and high-throughput screening.

Recombinant immunotoxins provide another possibility of target-selective drug design. Recombinant immunotoxins are composed of a bacterial or plant toxin either fused or chemically conjugated to a specific ligand, such as the variable domains of the heavy and light chains of mAbs or to a growth factor. Immunotoxins may contain bacterial toxins, such as Pseudomouas exotoxin A or diphtheria toxin, or plant toxins, such as ricin A or clavin. These recombinant molecules can selectively kill their target cells when internalized after binding to cell surface receptors of the target cells.

The use of antisense oligonucleotides represents another strategy to inhibit the activation of RTKs. Antisense oligonucleotides are short pieces of synthetic DNA or RNA that are designed to interact with the mRNA to block the transcription and thus the expression of the target proteins. Antisense oligonucleotides interact with the mRNA by Watson-Crick base-pairing and are therefore highly specific to the target protein. Several preclinical and clinical studies suggest that antisense therapy might be therapeutically useful for the treatment of solid tumors.

The potential of RTKs and their relevant signaling as selective anti-cancer targets for therapeutic intervention has been recognized. As a consequence, a variety of successful target specific drugs such as mAbs and RTK inhibitors have been developed and are currently being evaluated in clinical trials. Table 3 summarizes the most successful drugs against receptor tyrosine kinase signaling which are currently evaluated in clinical phases or have already been approved by the FDA.

TABLE 3

RTK Drugs Currently Under Clinical Evaluation

| RTK | Drug | Company | Description | Status |
|---|---|---|---|---|
| EGFR | ZA 18539 Iressa | AstraZeneca | TKI that inhibits EGFR signaling | Phase III |
| EGFR | Cetuximab C225 | ImClone Systems | Mab directed against EGFR | Phase III |
| EGFR | EGF fusion protein | Seragen | Recombinant diphtheria toxin-hEGF fusion protein | Phase II |
| HER2 | Trastuzumab Herceptin | Genetech | Mab directed against HER2 | Approved by the FDA in 1998 |
| IGF-IR | INX-4437 | INEX USA | Antisense oligonucleotides targeting IGR-IR | Phase I |
| VEGFR | SU5416 | SUGEN | TKI that inhibits VEGFR2 | Phase II |
| VEGFR/ FGFR/ PDGFR | SU6668 | SUGEN | RTK inhibition of VEGFR, FGFR, and PDGFR | Phase I |

Non-receptor PTKs lack transmembrane regions and, instead, form complexes with the intra-cellular regions of cell surface receptors. Receptors that function through non-receptor PTKs include those for cytokines, hormones (growth hormone and prolactin) and antigen-specific receptors on T and B lymphocytes.

Many of the PTKs were first identified as the products of mutant oncogenes in cancer cells where their activation was no longer subject to normal cellular controls. In fact, about one third of the known oncogenes encode PTKs, and it is well-known that cellular transformation (oncogenesis) is often accompanied by increased tyrosine phosphorylation activity.

Many tyrosine kinase inhibitors, such as flavopiridol, genistem, erbstatin, lavendustin A, staurosporine, and UCN-01, are derived from natural products. Inhibitors directed to the ATP binding site are also available. Signals from RTKs can also be inhibited at other target sites such as nuclear tyrosine kinases, membrane anchors (inhibition of farnesylation) and transcription factors.

Targeting the signaling potential of growth promoting tyrosine kinases such as EGFR, HER2, PDGFR, src, and abl, will block tumor growth while blocking IGF-I and TRK will interfere with tumor cell survival. Inhibition of these kinases will lead to tumor shrinkage and apoptosis. FklI/KDR and src are kinases necessary for neovascularization (angiogenesis) of tumors. Inhibition of these kinases will slow tumor growth and decrease metastases.

Inhibitors of RTKs suppress tumor development by preventing cell migration, invasion and metastases. These drugs are likely to increase the time required for tumor progression, and may inhibit or attenuate the aggressiveness of the disease but may not initially result in measurable tumor regression.

An example of cancer arising from a defective tyrosine kinase is a class of ALK positive lymphomas referred to as "ALKomas" which display inappropriate expression of a neural-specific tyrosine kinase, anaplastic lymphoma kinase (ALK).

Iressa (ZD1839) is an orally active selective EGF-R inhibitor. This compound disrupts signaling involved in cancer cell proliferation. The clinical efficacy of this agent shows that it is well tolerated by patients undergoing Phase I/II clinical trials. The compound has shown promising cytotoxicity towards several cancer cell lines.

Since the majority of protein kinases are expressed in the brain, often in a neuron-specific fashion, protein phosphorylation must play a key role in the development and function of the vertebrate central nervous system. Thus neuron-specific kinases are well established as targets for the development of pharmacologically active modulators.

In summary, kinase proteins are a major target for drug action and development. Accordingly, it is valuable to the field of pharmaceutical development to identify and characterize previously unknown members of kinase proteins. The present invention advances the state of the art by providing a previously unidentified human kinase protein that has homology to rat MRCK.

Utility of the MRCK1 Gene and MRCK1 Kinase

MRCKs are serine/threonine kinases with multiple functional domains. MRCKs are thought to act as a downstream effector of Cdc42 in cytoskeletal reorganization. Cdc42 is an essential GTPase that belongs to the Rho/Rac subfamily of Ras-like GTPases. These proteins act as molecular switches by responding to exogenous and/or endogenous signals and relaying those signals to activate downstream components of a biological pathway. The 11 current members of the Cdc42 family display between 75 and 100% amino acid identity and are functional, as well as structural, homologs. Cdc42 transduces signals to the actin cytoskeleton to initiate and maintain polarized growth and to mitogen-activated protein morphogenesis. In the budding yeast *Saccharomyces cerevisiae*, Cdc42 plays an important role in multiple actin-dependent morphogenetic events such as bud emergence, mating-projection formation, and pseudohyphal growth. In mammalian cells, Cdc42 regulates a variety of actin-dependent events and induces the JNK/SAPK protein kinase cascade, which leads to the activation of transcription factors within the nucleus. Cdc42 mediates these processes through interactions with a myriad of downstream effectors. In addition, Cdc42 has been implicated in a number of human diseases through interactions with its regulators and downstream effectors.

The MRCK family includes at least two related protein kinases: MRCK alpha and MRCK beta, which were isolated from a human brain cDNA library using a monoclonal antibody directed against myotonic dystrophy protein kinase (DMPK). The epitope shared by DMPK and MRCKs was located at the catalytic site of DMPK using a phage-displayed random peptide library (Lam LT, Hum Mol Genet 9:2167-2173, 2000).

MRCKs are involved in Cdc42-mediated myosin light chain phosphorylation (Dong et al., Eur J Cell Biol 81:231-42, 2002). Specifically, MRCK alpha was implicated in Cdc42-mediated peripheral actin formation and neurite outgrowth in HeLa and PC 12 cells, respectively. It was suggest that MRCK alpha may act as a downstream effector of Cdc42 in cytoskeletal reorganization (Leung et al., Mol Cell Biol 18:130-40, 1998).

The native MRCK exists in high-molecular-weight complexes. The three independent coiled-coil (CC) domains and the N-terminal region preceding the kinase domain are responsible for intermolecular interactions leading to MRCK alpha multimerization. N-terminus-mediated dimerization and consequent trans-autophosphorylation are critical processes regulating MRCK alpha catalytic activities. A region containing the two distal CC domains (CC2 and CC3; residues 658 to 930) was found to interact intramolecularly with the kinase domain and negatively regulates its activity. Its deletion also resulted in an active kinase, confirming a negative auto-regulatory role. The N-terminus-mediated dimerization and activation of MRCK and the negative kinase-distal CC domain interaction are two mutually exclusive events that tightly regulate the catalytic state of the kinase. Disruption of this interaction by a mutant kinase domain resulted in increased kinase activity. MRCK kinase activity was also elevated when cells were treated with phorbol ester, which can interact directly with a cysteine-rich domain next to the distal CC domain. It therefore appears that binding of phorbol ester to MRCK releases its auto-inhibition, allowing N-terminal dimerization and subsequent kinase activation. (Tan et al., Mol. Cell. Biol., 21:2767-78, 2001)

The approximately 190-kD MRCK kinases preferentially phosphorylate non-muscle myosin light chain at serine 19, which is known to be crucial for activating actin-myosin contractility. The p21-binding domain binds GTP-Cdc42 but not GDP-Cdc42. The multidomain structure includes a cysteine-rich motif resembling those of protein kinase C and n-chimaerin and a putative Pleckstrin homology domain. MRCK alpha and Cdc42$^{V12}$ co-localize, particularly at the cell periphery in transfected HeLa cells. Microinjection of a plasmid encoding MRCK alpha resulted in actin and myosin reorganization. Expression of kinase-dead MRCK alpha blocked Cdc42$^{V12}$-dependent formation of focal complexes and peripheral microspikes. This was not due to possible sequestration of the p21, as a kinase-dead MRCK alpha mutant defective in Cdc42 binding was an equally effective blocker. Coinjection of an MRCK alpha plasmid with a Cdc42 plasmid, at concentrations where Cdc42 plasmid by itself elicited no effect, led to the formation of the peripheral structures associated with a Cdc42-induced morphological phenotype. These Cdc42-type effects were not promoted upon coinjection with plasmids of kinase-dead or Cdc42-binding-deficient MRCK alpha mutants. These results suggest that MRCK alpha may act as a downstream effector of Cdc42 in cytoskeletal reorganization (Leung et al., Mol. Cell. Biol., 18:130-40, 1998).

Two major substrates, p130 and p85, for MRCK alpha-kinase have been identified. P130 is identified as the myosin binding subunit p1130, whereas p85 is a novel related protein. P85 contains N-terminal ankyrin repeats, an alpha-helical C terminus with leucine repeats, and a centrally located conserved motif with the MRCK alpha kinase phosphorylation site. Like MBS130, p85 is specifically associated with protein phosphatase Idelta (PPIdelta), and this requires the N-terminus, including the ankyrin repeats. This association is required for the regulation of both the catalytic activities and the assembly of actin cytoskeleton. The N-terminus, in association with PP1 delta, is essential for actin depolymerization, whereas the C-terminus antagonizes this action. The C-terminal effects consist of two independent events that involved both a conserved phosphorylation inhibitory motif and an alpha-helical leucine repeats. The former was able to interact with PP1 delta only in the phosphorylated state and result in inactivation of PP1 delta activity. This provides further evidence that phosphorylation of a myosin binding subunit protein by specific kinases confers conformational changes in a highly conserved region that plays an essential role in the regulation of its catalytic subunit activities (Tan et al., J. Biol. Chem., 276: 21209-16, 2001).

Taken together, MRCKs appear to be an important player in cytoskeletal reorganization, neuronal differentiation, and myotonic dystrophy. MRCKs may serve as a major target for drug action and development.

The present invention provides a new human kinase (MRCK1) which has sequence and structure similarities to rat MRCK alpha and other kinases. The multiple domains in MRCK1 share high sequence identities with the corresponding domains in other kinases. Each of these domains, either in its native form or in a mutant form, can be used to affect the function of the corresponding domain in other kinases. The kinase domain in MRCK1 can be used to phosphorylate suitable substrates, including p130 and p85 or substrate peptides containing MRCK alpha phosphorylation sites. The substrate peptides can be conjugated to antibodies, and the phosphate groups added to the substrate peptides can be radioactively or fluorescently labeled. Antibodies thus labeled can be used in various detection assays, as appreciated by one of skilled in the art.

The MRCK1 gene and gene products can be used as molecular markers for diagnosing, prognosing, and monitoring the treatment of disorders related to the aberrant expression of MRCK1. In addition, the MRCK1 gene can be used to screen for potential agents or drugs capable of enhancing or inhibiting the MRCK1 gene expression in human cells. The MRCK1 gene products (polynucleotide and polypeptide) can be used to screen for potential agents or drugs capable of enhancing or inhibiting MRCK1 activity. Furthermore, various therapeutic methods for treating disorders related to the aberrant expression of MRCK1 can be designed based on the MRCK1 gene, its variants, or the agents/drugs that affect the expression of the MRCK1 gene or the activity of the MRCK1 gene products.

The following subsections illustrate examples of the utilities of human MRCK1 gene and MRCK1 kinase. Various changes and modifications within the spirit and scope of the present invention will become apparent to those skilled in the art from the present description.

Polynucleotides and Variants Thereof

One aspect of the invention pertains to isolated polynucleotide probes capable of hybridizing to the MRCK1 gene or its transcripts, such as MRCK1 mRNAs. These probes can be used to detect the expression level of the MRCK1 gene in human tissue or cells. The present invention also contemplates polynucleotide fragments for use as PCR primers for the amplification or mutation of the MRCK1 gene or the MRCK1 kinase-coding sequences. Another aspect of the invention pertains to isolated polynucleotides that encode MRCK1, or a fragment or mutant thereof. These polynucleotides can be used for expressing MRCK1, or a fragment or mutant thereof. The protein products thus expressed can be used to screen for agents/drugs that modulate an activity of MRCK1. In addition, these polynucleotides can be used to designing gene therapy vectors which target the expression of the MRCK1 gene or an activity of MRCK1 in humans.

A polynucleotide comprising SEQ ID NO:1 or SEQ ID NO:3 can be prepared using standard molecular biology techniques as appreciated by one of ordinary skill in the art. For instance, primers derived from the 5' and 3' ends of SEQ ID NO:1 can be used to amplify mRNAs isolated from human tissues. The cDNA thus produced contains SEQ ID NO:1. Likewise, primers for amplifying the human genomic sequence containing SEQ ID NO:3 can be designed and used to prepare the genomic sequence of the MRCK1 gene. A variant (such as a homolog) or a fragment of SEQ ID NO:1 or SEQ ID NO:3 can be similarly prepared. Alternatively, probes can be designed to screen for cDNA or genomic sequence libraries in order to identify polynucleotide molecules comprising the full-length or fragments of SEQ ID NO:1 or SEQ ID NO:3. The molecules thus identified can be used to create suitable vectors comprising the full-length SEQ ID NO:1 or SEQ ID NO:3.

Polynucleotides capable of hybridizing to the MRCK1 gene can be prepared by standard synthetic techniques, e.g., using an automated DNA synthesizer. Preferably, the polynucleotide probes can hybridize to the MRCK1 gene under reduced stringent conditions, stringent conditions, or highly stringent conditions. In one embodiment, the polynucleotides comprise at least 15, 20, 25, 30, 50, 100, 150, 200, 250, 300, 350, 400, 450, 500, 550, 600, 650, 700, 750, 800, 850, 900, 950, 1000 or more consecutive nucleotides of SEQ ID NO:1. Any fragments of SEQ ID NO:1 and SEQ ID NO:3 may be used as hybridization probes or PCR primers for the MRCK1 gene or its transcripts. The probes/primers can be substantially purified.

In a preferred embodiment, the hybridization probes for the MRCK1 gene comprise a label group. The label group can be a radioisotope, a fluorescent compound, an enzyme, or an enzyme co-factor. Probes thus labeled can be used as part of a diagnostic kit for determining the expression level of the MRCK1 gene in human tissues.

This invention encompasses human MRCK1 gene homologs in other species. These homologs can be determined by search different sequence databases, such as the Entrez/GenBank sequence databases maintained by the NCBI. The invention also encompasses polynucleotide molecules which are structurally different from the molecules described above, but have the substantially same properties as the molecules described above. Such molecules include allelic variants, which will be described below in greater detail.

DNA sequence polymorphism in human MRCK1 gene exists among different individuals due to natural allelic variations. An allele is one of a group of genes which occur alternatively at a given genetic locus. DNA polymorphisms that affect the RNA expression level of the MRCK1 gene can also exist, e.g. through affecting the regulation or degradation of expression of the gene. The present invention contemplates all allelic variants of human MRCK1 gene. Allelic variants and other homologs of the MRCK1 gene can be isolated using probes/primers derived from SEQ ID NO:1 or SEQ ID NO:3.

It should, of course, be understood that SEQ ID NO:1 and SEQ ID NO:3 can be modified. The modified polynucleotides can comprise one or more mutations. These mutations can be substitutions, additions or deletions of 1, 2, 3, 5, 10, 15, 20 or more nucleotide residues in SEQ ID NO:1 or SEQ ID NO:3. Standard techniques can be used, such as site-directed mutagenesis or PCR-mediated mutagenesis. Preferably, these mutations create conservative amino acid substitutions. Alternatively, mutations can be introduced randomly along all or part of the MRCK1 gene or its cDNA, such as by saturation mutagenesis. Following mutagenesis, the encoded proteins can be expressed recombinantly and their activities can be determined.

In one embodiment, nucleotide substitutions leading to amino acid substitutions at "non-essential" amino acid residues can be introduced. A "non-essential" amino acid residue is a residue that can be altered without changing the biological activity of the protein. In contrast, an "essential" amino acid residue is required for the biological activity of the protein. Amino acid residues that are conserved among allelic variants or homologs of the MRCK1 gene from different species preferably are not changed in the present invention.

Accordingly, another aspect of the invention pertains to MRCK1 proteins that contain changes in amino acid residues that are not essential for the biological activity of MRCK1. These proteins differ in amino acid sequence from the original human MRCK1 kinase, but retain its biological activity. In one embodiment, the modified protein comprises an amino acid sequence at least about 91%, 95%, 98%, 99% or more homologous to SEQ ID NO:2.

In another embodiment, MRCK1 proteins contain mutations in amino acid residues which result in inhibition of MRCK1 activity. These mutated MRCK1 proteins can be used to inhibit MRCK1 activity in patients with disorders related to the aberrant expression of MRCK1.

A polynucleotide of this invention can be further modified to increase its stability in vivo. Possible modifications include, but are not limited to, the addition of flanking sequences at the 5' and/or 3' ends; the use of phosphorothioate or 2-o-methyl rather than phosphodiester linkages in the backbone; and/or the inclusion of nontraditional bases such as inosine, queosine and wybutosine, as well as acetyl-methyl-, thio- and other modified forms of adenine, cytidine, guanine, thymine and uridine.

Polynucleotide molecules which are antisense to the MRCK1 gene can be prepared. An "antisense" polynucleotide comprises a nucleotide sequence which is complementary to a "sense" polynucleotide which encodes a protein. An antisense polynucleotide can bind via hydrogen bonds to the sense polynucleotide.

Antisense polynucleotides of the invention can be designed according to the rules of Watson and Crick base pairing. The antisense polynucleotide molecule can be complementary to the entire coding region or part of the coding region of the MRCK1 gene. The antisense polynucleotide molecule can also be complementary to a "noncoding region" in the coding strand of the MRCK1 gene. Preferably, the antisense polynucleotide is an oligonucleotide which is antisense to only a portion of the MRCK1 gene. An antisense polynucleotide can be, for example, about 5, 10, 15, 20, 25, 30, 35, 40, 45 or 50 nucleotides in length. An antisense polynucleotide of the invention can be constructed using chemical synthesis and enzymatic ligation reactions as appreciated by one of ordinary skill in the art. For example, an antisense polynucleotide can be chemically synthesized using naturally occurring nucleotides or variously modified nucleotides designed to increase the biological stability of the molecules or to increase the physical stability of the duplex formed between the antisense and sense polynucleotides. Examples of modified nucleotides which can be used to generate the antisense polynucleotide include 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyl adenosine, uracil-5-oxyacetic acid, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, (acp3)w, and 2,6-diaminopurine. Phosphorothioate derivatives and acridine substituted nucleotides can also be used. Alternatively, the antisense polynucleotide can be produced biologically using an expression vector into which a polynucleotide has been subcloned in an antisense orientation (i.e., RNA transcribed from the inserted polynucleotide will be of an antisense orientation to the target polynucleotide of interest).

The antisense polynucleotides of the invention can be administered to a subject or applied in situ such that they hybridize or bind to cellular mRNAs and/or genomic DNA's that encode MRCK1 kinase, thereby inhibiting the expression of MRCK1 kinase. The hybridization can result in a stable duplex via conventional nucleotide complementarity. An example route for administering antisense polynucleotides includes direct injection at a tissue site. Antisense polynucleotides can also be modified first, and then administered systemically. For example, for systemic administration, antisense molecules can be modified such that they specifically bind to receptors or antigens expressed on a selected cell surface. Suitable modifications include linking the antisense polynucleotides to peptides or antibodies which bind to the cell surface receptors or antigens. In addition, the antisense polynucleotides can be delivered to cells using vectors. To achieve sufficient intra-cellular concentrations of the antisense molecules, strong pol II or pol III promoters may be used in the vectors.

In one embodiment, the antisense polynucleotides are α-anomeric polynucleotides. An α-anomeric polynucleotide molecule forms specific double-stranded hybrid with a complementary RNA in which, contrary to the usual β-units, the strands run parallel to each other. The antisense polynucleotide molecule can also comprise a 2-o-methylribonucleotide or a chimeric RNA-DNA analog.

In another embodiment, the antisense polynucleotide is a ribozyme. Ribozymes are catalytic RNA molecules with ribonuclease activity which are capable of cleaving a single-stranded polynucleotide, such as an mRNA, to which they have a complementary region. Thus, ribozymes (e.g., hammerhead ribozymes described in Haselhoif and Gerlach Nature 334:585-591, 1988) can be used to catalytically cleave mRNA transcripts of MRCK1 in order to inhibit its expression. A ribozyme having specificity for the MRCK1 gene or its transcripts can be designed based upon SEQ ID NO:1 or 3. mRNAs transcribed from the MRCK1 gene can be used to select from a pool of RNA molecules a catalytic RNA having a specific ribonuclease activity.

Alternatively, the expression of the MRCK1 gene can be inhibited by using nucleotide sequences complementary to the regulatory region (e.g., the promoter and/or enhancers). These nucleotide sequences can form triple helical structures that prevent transcription of the gene in the target cells.

Expression of the MRCK1 gene can also be inhibited using RNA interference ("RNAi"). RNAi is a phenomenon in which the introduction of double-stranded RNA (dsRNA) into certain organisms or cell types causes degradation of the homologous mRNA. First discovered in the nematode *Caenorhabditis elegans*, RNAi has since been found to operate in a wide range of organisms. For example, in mammalian cells, introduction of long dsRNA (>30 nucleotides) can initiate a potent antiviral response, exemplified by nonspecific inhibition of protein synthesis and RNA degradation. RNA interference provides a mechanism of gene silencing at the mRNA level. In recent years, RNAi has become an endogenous and potent gene-specific silencing technique that uses double-stranded RNAs (dsRNA) to mark a particular transcript for degradation in vivo. It also offers an efficient and broadly applicable approach for gene knock-out. In addition, RNAi technology can be used for therapeutic purposes. For example, RNAi targeting Fas-mediated apoptosis has been shown to protect mice from fulminant hepatitis. RNAi technology has been disclosed in numerous publications, such as U.S. Pat. Nos. 5,919,619, 6,506,559 and PCT Publication Nos. WO99/14346, WO01/70949, WO01/36646, WO00/63364, WO00/44895, WO01/75164, WO01/92513, WO01/68836 and WO01/29058.

A sequence capable of inhibiting gene expression by RNA interference can have any length. For instance, the sequence can have at leats 10, 15, 20, 25, 30, 35, 40, 45, 50, 100 or more consecutive nucleotides. The sequence can be dsRNA or any other type of polynucleotide, provided that the sequence can form a functional silencing complex to degrade the target mRNA transcript.

In one embodiment, the sequence comprises or consists of a short interfering RNAs (siRNA). The siRNA can be dsRNA having 19-25 nucleotides. siRNAs can be produced endogenously by degradation of longer dsRNA molecules by an RNase III-related nuclease called Dicer. siRNAs can also be introduced into a cell exogenously, or by transcription of an expression construct. Once formed, the siRNAs assemble with protein components into endoribonuclease-containing complexes known as RNA-induced silencing complexes (RISCs). An ATP-generated unwinding of the siRNA activates the RISCs, which in turn target the complementary mRNA transcript by Watson-Crick base-pairing, thereby cleaving and destroying the mRNA. Cleavage of the mRNA takes place near the middle of the region bound by the siRNA strand. This sequence specific mRNA degradation results in gene silencing.

At least two ways can be employed to achieve siRNA-mediated gene silencing. First, siRNAs can be synthesized in vitro and introduced into cells to transiently suppress gene expression. Synthetic siRNA provides an easy and efficient way to achieve RNAi. siRNA are duplexes of short mixed oligonucleotides which can include, for example, 19 RNAs nucleotides with symmetric dinucleotide 3' overhangs. Using synthetic 21 bp siRNA duplexes (e.g., 19 RNA bases followed by a UU or dTdT 3' overhang), sequence specific gene silencing can be achieved in mammalian cells. These siRNAs can specifically suppress targeted gene translation in mammalian cells without activation of DNA-dependent protein kinase (PKR) by longer dsRNA, which may result in non-specific repression of translation of many proteins.

Second, siRNAs can be expressed in vivo from vectors. This approach can be used to stably express siRNAs in cells or transgenic animals. In one embodiment, siRNA expression vectors are engineered to drive siRNA transcription from polymerase III (pol III) transcription units. Pol III transcription units are suitable for hairpin siRNA expression, since they deploy a short AT rich transcription termination site that leads to the addition of 2 bp overhangs (e.g., UU) to hairpin siRNAs—a feature that is helpful for siRNA function. The Pol III expression vectors can also be used to create transgenic mice that express siRNA.

In another embodiment, siRNAs can be expressed in a tissue-specific manner. Under this approach, long double-stranded RNAs (dsRNAs) are first expressed from a promoter (such as CMV (pol II)) in the nuclei of selected cell lines or transgenic mice. The long dsRNAs are processed into siRNAs in the nuclei (e.g., by Dicer). The siRNAs exit from the nuclei and mediate gene-specific silencing. A similar approach can be used in conjunction with tissue-specific (pol II) promoters to create tissue-specific knock-down mice.

Any 3' dinucleotide overhang, such as UU, can be used for siRNA design. In some cases, G residues in the overhang are avoided because of the potential for the siRNA to be cleaved by RNase at single-stranded G residues.

With regard to the siRNA sequence itself, it has been found that siRNAs with 30-50% GC content can be more active than those with a higher G/C content in certain cases. Moreover, since a 4-6 nucleotide poly(T) tract may act as a termination signal for RNA pol III, stretches of >4 Ts or As in the target sequence may be avoided in certain cases when designing sequences to be expressed from an RNA pol III promoter. In addition, some regions of mRNA may be either highly structured or bound by regulatory proteins. Thus, it may be helpful to select siRNA target sites at different positions along the length of the gene sequence. Finally, the potential target sites can be compared to the appropriate genome database (human, mouse, rat, etc.). Any target sequences with more than 16-17 contiguous base pairs of homology to other coding sequences may be eliminated from consideration in certain cases.

In one embodiment, siRNA can be designed to have two inverted repeats separated by a short spacer sequence and end with a string of Ts that serve as a transcription termination site. This design produces an RNA transcript that is predicted to fold into a short hairpin siRNA. The selection of siRNA target sequence, the length of the inverted repeats that encode the stem of a putative hairpin, the order of the inverted repeats, the length and composition of the spacer sequence that encodes the loop of the hairpin, and the presence or absence of 5'-overhangs, can vary to achieve desirable results.

The siRNA targets can be selected by scanning an mRNA sequence for AA dinucleotides and recording the 19 nucleotides immediately downstream of the AA. Other methods can also been used to select the siRNA targets. In one example, the selection of the siRNA target sequence is purely empirically determined (see e.g., Sui et al., Proc. Natl. Acad. Sci. USA 99: 5515-5520, 2002), as long as the target sequence starts with GG and does not share significant sequence homology with other genes as analyzed by BLAST search. In another example, a more elaborate method is employed to select the siRNA target sequences. This procedure exploits an observation that any accessible site in endogenous mRNA can be targeted for degradation by synthetic oligodeoxyribonucleotide/RNase H method (Lee et al., Nature Biotechnology 20:500-505, 2002).

In another embodiment, the hairpin siRNA expression cassette is constructed to contain the sense strand of the target, followed by a short spacer, the antisense strand of the target, and 5-6 Ts as transcription terminator. The order of the sense and antisense strands within the siRNA expression constructs can be altered without affecting the gene silencing activities of the hairpin siRNA. In certain instances, the reversal of the order may cause partial reduction in gene silencing activities.

The length of nucleotide sequence being used as the stem of siRNA expression cassette can range, for instance, from 19 to 29. The loop size can range from 3 to 23 nucleotides. Other lengths and/or loop sizes can also be used.

In yet another embodiment, a 5' overhang in the hairpin siRNA construct can be used, provided that the hairpin siRNA is functional in gene silencing. In one specific example, the 5' overhang includes about 6 nucleotide residues.

In still yet another embodiment, the target sequence for RNAi is a 21-mer sequence fragment selected from SEQ ID NO:1. The 5' end of the target sequence has dinucleotide "NA," where "N" can be any base and "A" represents adenine. The remaining 19-mer sequence has a GC content of between 35% and 55%. In addition, the remaining 19-mer sequence does not include any four consecutive A or T (i.e., AAAA or TTTT), three consecutive G or C (i.e., GGG or CCC), or seven "GC" in a role. Exemplary RNAi target sequences identified according to the above-described criteria ("relaxed" criteria) are illustrated in Table 4. The siRNA sequences for each target sequence (listed in the same row as the target sequence and including the sense strand and the antisense strand) are also indicated in Table 4.

Additional criteria can also be used for selecting RNAi target sequences. For instance, the GC content of the remaining 19-mer sequence can be limited to between 45% and 55%. Moreover, any 19-mer sequence having three consecutive identical bases (i.e., GGG, CCC, TTT, or AAA) or a palindrome sequence with 5 or more bases is excluded. Furthermore, the remaining 19-mer sequence can be selected to have low sequence homology to other human genes. In one specific example, potential target sequences are searched by BLASTN against NCBI's human UniGene cluster sequence database. The human UniGene database contains non-redundant sets of gene-oriented clusters. Each UniGene cluster includes sequences that represent a unique gene. 19-mer sequences producing no hit to other human genes under the BLASTN search can be selected. During the search, the e-value may be set at a stringent value (such as "1"). Exemplary target sequences derived using these additional conditions ("stringent" criteria) are shown in Table 5. The siRNA sequences for each target sequence (listed in the same row as the target sequence and including the sense strand and the antisense strand) are also indicated in Table 5.

The effectiveness of the siRNA sequences listed in Tables 4 and 5, as well as any other RNAi sequence derived according to the present invention, can be evaluated using various methods known in the art. For instance, an siRNA sequence of the present invention can be introduced into a cell that expresses the MRCK1 gene. The polypeptide or mRNA level of the MRCK1 gene in the cell can be detected. A substantial change in the expression level of the MRCK1 gene before and after the introduction of the siRNA sequence is indicative of the effectiveness of the siRNA sequence in suppressing the expression of the MRCK1 gene. In one specific example, the expression levels of other genes are also monitored before and after the introduction of the siRNA sequence. An siRNA sequence which has inhibitory effect on MRCK1 gene expression but does not significantly affect the expression of other genes can be selected. In another specific example, multiple siRNA or other RNAi sequences can be introduced into the same target cell. These siRNA or RNAi sequences specifically inhibit MRCK1 gene expression but not the expression of other genes. In yet another specific example, siRNA or other RNAi sequences that inhibit the expression of both the MRCK1 gene and other gene or genes can be used.

TABLE 4

Exemplary RNAi Target Sequences in the MRCK1 Gene and the Corresponding siRNAs (Under Relaxed Criteria)

| Target Sequence | siRNA Sense Strand | siRNA Antisense Strand |
|---|---|---|
| SEQ ID NO: 10 | SEQ ID NO: 11 | SEQ ID NO: 12 |
| SEQ ID NO: 13 | SEQ ID NO: 14 | SEQ ID NO: 15 |
| SEQ ID NO: 16 | SEQ ID NO: 17 | SEQ ID NO: 18 |
| SEQ ID NO: 19 | SEQ ID NO: 20 | SEQ ID NO: 21 |
| SEQ ID NO: 22 | SEQ ID NO: 23 | SEQ ID NO: 24 |
| SEQ ID NO: 25 | SEQ ID NO: 26 | SEQ ID NO: 27 |
| SEQ ID NO: 28 | SEQ ID NO: 29 | SEQ ID NO: 30 |
| SEQ ID NO: 31 | SEQ ID NO: 32 | SEQ ID NO: 33 |
| SEQ ID NO: 34 | SEQ ID NO: 35 | SEQ ID NO: 36 |
| SEQ ID NO: 37 | SEQ ID NO: 38 | SEQ ID NO: 39 |
| SEQ ID NO: 40 | SEQ ID NO: 41 | SEQ ID NO: 42 |
| SEQ ID NO: 43 | SEQ ID NO: 44 | SEQ ID NO: 45 |
| SEQ ID NO: 46 | SEQ ID NO: 47 | SEQ ID NO: 48 |
| SEQ ID NO: 49 | SEQ ID NO: 50 | SEQ ID NO: 51 |
| SEQ ID NO: 52 | SEQ ID NO: 53 | SEQ ID NO: 54 |
| SEQ ID NO: 55 | SEQ ID NO: 56 | SEQ ID NO: 57 |
| SEQ ID NO: 58 | SEQ ID NO: 59 | SEQ ID NO: 60 |
| SEQ ID NO: 61 | SEQ ID NO: 62 | SEQ ID NO: 63 |
| SEQ ID NO: 64 | SEQ ID NO: 65 | SEQ ID NO: 66 |
| SEQ ID NO: 67 | SEQ ID NO: 68 | SEQ ID NO: 69 |
| SEQ ID NO: 70 | SEQ ID NO: 71 | SEQ ID NO: 72 |
| SEQ ID NO: 73 | SEQ ID NO: 74 | SEQ ID NO: 75 |
| SEQ ID NO: 76 | SEQ ID NO: 77 | SEQ ID NO: 78 |
| SEQ ID NO: 79 | SEQ ID NO: 80 | SEQ ID NO: 81 |
| SEQ ID NO: 82 | SEQ ID NO: 83 | SEQ ID NO: 84 |
| SEQ ID NO: 85 | SEQ ID NO: 86 | SEQ ID NO: 87 |
| SEQ ID NO: 88 | SEQ ID NO: 89 | SEQ ID NO: 90 |
| SEQ ID NO: 91 | SEQ ID NO: 92 | SEQ ID NO: 93 |
| SEQ ID NO: 94 | SEQ ID NO: 95 | SEQ ID NO: 96 |
| SEQ ID NO: 97 | SEQ ID NO: 98 | SEQ ID NO: 99 |
| SEQ ID NO: 100 | SEQ ID NO: 101 | SEQ ID NO: 102 |
| SEQ ID NO: 103 | SEQ ID NO: 104 | SEQ ID NO: 105 |
| SEQ ID NO: 106 | SEQ ID NO: 107 | SEQ ID NO: 108 |
| SEQ ID NO: 109 | SEQ ID NO: 110 | SEQ ID NO: 111 |
| SEQ ID NO: 112 | SEQ ID NO: 113 | SEQ ID NO: 114 |
| SEQ ID NO: 115 | SEQ ID NO: 116 | SEQ ID NO: 117 |

TABLE 4-continued

Exemplary RNAi Target Sequences in the MRCK1 Gene and the Corresponding siRNAs (Under Relaxed Criteria)

| Target Sequence | siRNA Sense Strand | siRNA Antisense Strand |
|---|---|---|
| SEQ ID NO: 118 | SEQ ID NO: 119 | SEQ ID NO: 120 |
| SEQ ID NO: 121 | SEQ ID NO: 122 | SEQ ID NO: 123 |
| SEQ ID NO: 124 | SEQ ID NO: 125 | SEQ ID NO: 126 |
| SEQ ID NO: 127 | SEQ ID NO: 128 | SEQ ID NO: 129 |
| SEQ ID NO: 130 | SEQ ID NO: 131 | SEQ ID NO: 132 |
| SEQ ID NO: 133 | SEQ ID NO: 134 | SEQ ID NO: 135 |
| SEQ ID NO: 136 | SEQ ID NO: 137 | SEQ ID NO: 138 |
| SEQ ID NO: 139 | SEQ ID NO: 140 | SEQ ID NO: 141 |
| SEQ ID NO: 142 | SEQ ID NO: 143 | SEQ ID NO: 144 |
| SEQ ID NO: 145 | SEQ ID NO: 146 | SEQ ID NO: 147 |
| SEQ ID NO: 148 | SEQ ID NO: 149 | SEQ ID NO: 150 |
| SEQ ID NO: 151 | SEQ ID NO: 152 | SEQ ID NO: 153 |
| SEQ ID NO: 154 | SEQ ID NO: 155 | SEQ ID NO: 156 |
| SEQ ID NO: 157 | SEQ ID NO: 158 | SEQ ID NO: 159 |
| SEQ ID NO: 160 | SEQ ID NO: 161 | SEQ ID NO: 162 |
| SEQ ID NO: 163 | SEQ ID NO: 164 | SEQ ID NO: 165 |
| SEQ ID NO: 166 | SEQ ID NO: 167 | SEQ ID NO: 168 |
| SEQ ID NO: 169 | SEQ ID NO: 170 | SEQ ID NO: 171 |
| SEQ ID NO: 172 | SEQ ID NO: 173 | SEQ ID NO: 174 |
| SEQ ID NO: 175 | SEQ ID NO: 176 | SEQ ID NO: 177 |
| SEQ ID NO: 178 | SEQ ID NO: 179 | SEQ ID NO: 180 |
| SEQ ID NO: 181 | SEQ ID NO: 182 | SEQ ID NO: 183 |
| SEQ ID NO: 184 | SEQ ID NO: 185 | SEQ ID NO: 186 |
| SEQ ID NO: 187 | SEQ ID NO: 188 | SEQ ID NO: 189 |
| SEQ ID NO: 190 | SEQ ID NO: 191 | SEQ ID NO: 192 |
| SEQ ID NO: 193 | SEQ ID NO: 194 | SEQ ID NO: 195 |
| SEQ ID NO: 196 | SEQ ID NO: 197 | SEQ ID NO: 198 |
| SEQ ID NO: 199 | SEQ ID NO: 200 | SEQ ID NO: 201 |
| SEQ ID NO: 202 | SEQ ID NO: 203 | SEQ ID NO: 204 |
| SEQ ID NO: 205 | SEQ ID NO: 206 | SEQ ID NO: 207 |
| SEQ ID NO: 208 | SEQ ID NO: 209 | SEQ ID NO: 210 |
| SEQ ID NO: 211 | SEQ ID NO: 212 | SEQ ID NO: 213 |
| SEQ ID NO: 214 | SEQ ID NO: 215 | SEQ ID NO: 216 |
| SEQ ID NO: 217 | SEQ ID NO: 218 | SEQ ID NO: 219 |
| SEQ ID NO: 220 | SEQ ID NO: 221 | SEQ ID NO: 222 |
| SEQ ID NO: 223 | SEQ ID NO: 224 | SEQ ID NO: 225 |
| SEQ ID NO: 226 | SEQ ID NO: 227 | SEQ ID NO: 228 |
| SEQ ID NO: 229 | SEQ ID NO: 230 | SEQ ID NO: 231 |
| SEQ ID NO: 232 | SEQ ID NO: 233 | SEQ ID NO: 234 |
| SEQ ID NO: 235 | SEQ ID NO: 236 | SEQ ID NO: 237 |
| SEQ ID NO: 238 | SEQ ID NO: 239 | SEQ ID NO: 240 |
| SEQ ID NO: 241 | SEQ ID NO: 242 | SEQ ID NO: 243 |
| SEQ ID NO: 244 | SEQ ID NO: 245 | SEQ ID NO: 246 |
| SEQ ID NO: 247 | SEQ ID NO: 248 | SEQ ID NO: 249 |
| SEQ ID NO: 250 | SEQ ID NO: 251 | SEQ ID NO: 252 |
| SEQ ID NO: 253 | SEQ ID NO: 254 | SEQ ID NO: 255 |
| SEQ ID NO: 256 | SEQ ID NO: 257 | SEQ ID NO: 258 |
| SEQ ID NO: 259 | SEQ ID NO: 260 | SEQ ID NO: 261 |
| SEQ ID NO: 262 | SEQ ID NO: 263 | SEQ ID NO: 264 |

TABLE 5

Exemplary RNAi Target Sequences in the MRCK1 Gene and the Corresponding siRNAs (Under Stringent Criteria)

| Target Sequence | siRNA Sense Strand | siRNA Antisense Strand |
|---|---|---|
| SEQ ID NO: 265 | SEQ ID NO: 266 | SEQ ID NO: 267 |
| SEQ ID NO: 268 | SEQ ID NO: 269 | SEQ ID NO: 270 |
| SEQ ID NO: 271 | SEQ ID NO: 272 | SEQ ID NO: 273 |
| SEQ ID NO: 274 | SEQ ID NO: 275 | SEQ ID NO: 276 |
| SEQ ID NO: 277 | SEQ ID NO: 278 | SEQ ID NO: 279 |
| SEQ ID NO: 280 | SEQ ID NO: 281 | SEQ ID NO: 282 |
| SEQ ID NO: 283 | SEQ ID NO: 284 | SEQ ID NO: 285 |
| SEQ ID NO: 286 | SEQ ID NO: 287 | SEQ ID NO: 288 |
| SEQ ID NO: 289 | SEQ ID NO: 290 | SEQ ID NO: 291 |
| SEQ ID NO: 292 | SEQ ID NO: 293 | SEQ ID NO: 294 |
| SEQ ID NO: 295 | SEQ ID NO: 296 | SEQ ID NO: 297 |
| SEQ ID NO: 298 | SEQ ID NO: 299 | SEQ ID NO: 300 |

TABLE 5-continued

Exemplary RNAi Target Sequences in the MRCK1 Gene and the Corresponding siRNAs (Under Stringent Criteria)

| Target Sequence | siRNA Sense Strand | siRNA Antisense Strand |
|---|---|---|
| SEQ ID NO: 301 | SEQ ID NO: 302 | SEQ ID NO: 303 |
| SEQ ID NO: 304 | SEQ ID NO: 305 | SEQ ID NO: 306 |

In yet another embodiment, the polynucleotides of the present invention can be modified at the base moiety, sugar moiety or phosphate backbone to improve the stability, hybridization, or solubility of the molecules. For instance, the deoxyribose phosphate backbone of the polynucleotide molecules can be modified to generate peptide polynucleotides (see, Hyrup et al, Bioorganic & Medicinal Chemistry, 4:523, 1996). As used herein, the terms "peptide polynucleotides" or "PNAs" refer to polynucleotide mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. PNA oligomers can be synthesized using standard solid phase peptide synthesis protocols.

PNAs can be used in therapeutic and diagnostic applications. For example, PNAs can be used as antisense agents for sequence-specific modulation of the MRCK1 gene expression. PNAs can also be used in the analysis of single base pair mutations in a gene, (e.g., by PNA-directed PCR clamping); as artificial restriction enzymes when used in combination with other enzymes, (e.g., S1 nucleases); or as probes or primers for DNA sequencing or hybridization.

In one embodiment, PNAs can be modified to enhance their stability or cellular uptake by attaching lipophilic or other helper groups to PNA, by the formation of PNA-DNA chimeras, or by the use of liposomes or other drug delivery techniques known in the art. For example, PNA-DNA chimeras of the polynucleotides of the invention can be generated. These chimeras allow DNA recognition enzymes, such as RNase H and DNA polymerases, to interact with the DNA portion while the PNA portion provides high binding affinity and specificity. PNA-DNA chimeras can be linked using linkers of appropriate lengths which are selected based on base stacking, number of bonds between the nucleobases, and orientations. The PNA-DNA chimeras can be synthesized as follows. A DNA chain is synthesized on a solid support using standard phosphoramidite coupling chemistry and modified nucleoside analogs. PNA monomers are then coupled in a stepwise manner to produce a chimeric molecule with a 5' PNA segment and a 3' DNA segment. Alternatively, chimeric molecules can be synthesized with a 5' DNA segment and a 3' PNA segment.

In other embodiments, the polynucleotides of this invention may include other appended groups such as peptides (e.g., for targeting host cell receptors in vivo), or agents facilitating transportation across the cell membrane or the blood-kidney barrier (see, e.g., PCT Publication No. WO89/10134). In addition, polynucleotides can be modified using hybridization-triggered cleavage agents or intercalating agents. To this end, the polynucleotides can be conjugated to another molecule (e.g., a peptide, hybridization triggered cross-linking agent, transport agent, or hybridization-triggered cleavage agent). Furthermore, the polynucleotide can be detectably labeled.

Polypeptides and Variants Thereof

Several aspects of the invention pertain to isolated MRCK1 polypeptides and mutated MRCK1 polypeptides capable of inhibiting normal MRCK1 activity. The present invention also contemplates immunogenic polypeptide fragments suitable for raising anti-MRCK1 antibodies.

In one embodiment, native MRCK1 polypeptides can be isolated from cells or tissue sources by using standard protein purification techniques. Standard purification methods include electrophoresis, molecular, immunological and chromatographic techniques. Specific examples include ion exchange, hydrophobic, affinity or reverse-phase HPLC chromatography, and chromatofocusing. In one embodiment, MRCK1 polypeptides are purified using a standard affinity column coupled with anti-MRCK1 antibodies. Ultrafiltration and diafiltration techniques can also be used. The degree of purification depends on the purpose of the use of the MRCK1 polypeptides. In some instances, purification is not necessary.

In another embodiment, MRCK1 polypeptides or mutated MRCK1 polypeptides capable of inhibiting normal MRCK1 activity are produced by recombinant DNA techniques. Alternative to recombinant expression, MRCK1 polypeptides or mutated MRCK1 polypeptides can be synthesized chemically using standard peptide synthesis techniques.

The invention provides MRCK1 polypeptides encoded by the human MRCK1 gene, or homologs thereof. The polypeptides of this invention can be substantially homologous to human MRCK1 kinase (SEQ ID NO:2). Preferably, these polypeptides retain the biological activity of the native MRCK1 kinase. In one embodiment, the polypeptides comprise an amino acid sequence which is at least about 91%, 95%, 98%, 99% or more homologous to SEQ ID NO:2.

Comparison of sequences and determination of percent identity between two sequences can be accomplished using a mathematical algorithm. The percent identity between two amino acid sequences can be determined using the Needleman and Wunsch (J. Mol. Biol. 48:444-453, 1970) algorithm, or the GAP program in the GCG software package which uses either a Blossom 62 matrix or a PAM250 matrix, and a gap weight of 16, 14, 12, 10, 8, 6, or 4 and a length weight of 1, 2, 3, 4, 5, or 6. The percent identity between two nucleotide sequences can be determined using the GAP program in the GCG software package, which uses a NWSgapdna.CMP matrix and a gap weight of 40, 50, 60, 70, or 80 and a length weight of 1, 2, 3, 4, 5, or 6. The percent identity between two amino acid or nucleotide sequences can also be determined using the algorithm of E. Meyers and W. Miller (CABIOS, 4:11-17, 1989) which has been incorporated into the ALIGN program (version 2.0), or the pairwise BLAST program available at NCBI's BLAST web site.

The polypeptide and polynucleotide sequences of the present invention can be used as query sequences for searching public databases in order to identify similar sequences. The search can be conducted using BLAST programs, such as the protein BLAST, nucleotide BLAST, pairwise BLAST, and genomic BLAST, that are available at the BLAST web site maintained by the NCBI. When using BLAST programs, the default parameters of the respective programs can also be used.

The invention further provides chimeric or fusion MRCK1 polypeptides. A fusion MRCK1 polypeptide contains an MRCK1-related polypeptide and a non-MRCK1 polypeptide. The MRCK1-related polypeptides include all or a portion of SEQ ID NO:2 or its variant. A peptide linker sequence can be employed to separate the MRCK1-related polypeptide from the non-MRCK1 polypeptide components by a distance sufficient to ensure that each polypeptide folds into its native secondary and tertiary structures. Such a peptide linker sequence is incorporated into the fusion protein using standard techniques well-known in the art. Suitable peptide linker sequences can be chosen based on the following factors: (1) their ability to adopt a flexible extended conformation; (2) their inability to adopt a secondary structure that could interact with functional epitopes on the MRCK1-related polypeptide and non-MRCK1 polypeptide; and (3) the lack of hydrophobic or charged residues that might react with the polypeptide functional epitopes. Preferred peptide linker sequences contain Gly, Asn and Ser residues. Other near neutral amino acids, such as Thr and Ala can also be used in the linker sequence. Amino acid sequences suitable as linkers include those disclosed in Maratea et al., Gene, 40:39-46, 1985; Murphy et al., Proc. Natl. Acad. Sci. USA, 83:8258-8262, 1986; and U.S. Pat. Nos. 4,935,233 and 4,751,180. The linker sequences may be from 1 to about 50 amino acids in length. Linker sequences are not required when the MRCK1-related polypeptide or the non-MRCK1 polypeptide has non-essential N-terminal amino acid regions that can be used to separate the respective functional domains and thereby prevent steric interference.

In one embodiment, the fusion protein is a GST-MRCK1 fusion protein in which an MRCK1-related sequence, such as SEQ ID NO:2, is fused to the C-terminus of the GST sequence. This fusion protein can facilitate the purification of the recombinant MRCK1.

The MRCK1-fusion proteins of the invention can be incorporated into pharmaceutical compositions and administered to a subject. The MRCK1-fusion proteins can be used to affect the bioavailability of an MRCK1 substrate. The MRCK1-fusion proteins can also be used for the treatment or prevention of damages caused by (i) aberrant modification or mutation of MRCK1, or (ii) aberrant post-translational modification of MRCK1. It is also conceivable that a fusion protein containing a normal or mutated MRCK1 polypeptide, or a fragment thereof, can be used to inhibit MRCK1 activity in a human subject.

Moreover, the MRCK1-fusion proteins can be used as immunogens to produce anti-MRCK1 antibodies. They can also be used to purify MRCK1 ligands and to screen for molecules capable of inhibiting the interaction between MRCK1 and its substrates.

Preferably, the MRCK1-chimeric or fusion proteins of the invention are produced using standard recombinant DNA techniques. Commercially available expression vectors which encode a fusion moiety (e.g., a GST polypeptide) can be used.

A signal sequence can be used to facilitate secretion and isolation of the secreted protein or other proteins of interest. Signal sequences are typically characterized by a core of hydrophobic amino acids which are generally cleaved from the mature protein. Such signal peptides contain processing sites that allow cleavage of the signal sequence from the mature proteins as they pass through the secretory pathway. The present invention encompasses MRCK1 polypeptides having a signal sequence, or the polynucleotide sequences encoding the same.

The present invention also pertains to MRCK1 mutants which function as antagonists to MRCK1. In one embodiment, antagonists of MRCK1 are used as therapeutic agents. For example, a mutant of MRCK1 that forms a nonfunctional dimer with a wide-type MRCK1 (the so-called dominant negative mutant) can decrease the activity of MRCK1 and may ameliorate diseases in a subject wherein MRCK1 are abnormally increased in level or activity. Dominant negative MRCK1 mutants can be generated by mutagenesis, as appreciated by one skilled in the art.

MRCK1 mutants which function as either MRCK1 agonists or antagonists can be identified by screening combinatorial libraries of mutants. A variegated library of MRCK1 mutants can be produced by, for example, enzymatically ligating a mixture of synthetic oligonucleotides into gene sequences such that a degenerate set of potential MRCK1 sequences is expressible as individual polypeptides, or alternatively, as a set of larger fusion proteins containing the set of MRCK1 sequences therein. There are a variety of methods which can be used to produce libraries of potential MRCK1 mutants from a degenerate oligonucleotide sequence. A degenerate gene sequence can be chemically synthesized using an automatic DNA synthesizer. The synthetic gene can then be ligated into an appropriate expression vector.

In one embodiment, a library of coding sequences can be generated using nucleases. For instance, double-stranded PCR fragments of the MRCK1 coding sequence can be treated by a nuclease which produces about one nick per molecule. The double-stranded DNAs then are subject to a cycle of denaturing and re-naturing. The newly reformed DNAs, which may include sense/antisense pairs from different nicked products, are treated with S1 nuclease to remove single-stranded portions. Using this method, an expression library which encodes N-terminal, C-terminal or internal fragments of MRCK1 can be derived.

In addition, recursive ensemble mutagenesis (REM), a technique which enhances the frequency of functional mutants in the libraries, can be used to prepare MRCK1 mutants (Delgrave et al., Protein Engineering, 6:327-331, 1993).

MRCK1 fragments, or variants thereof, can also be generated using synthetic means, such as solid-phase synthesis methods. Preferably, the synthesized fragment has less than about 100 amino acids, or preferably, less than about 50 amino acids.

Antibodies

In accordance with another aspect of the present invention, antibodies specific to MRCK1 or its variants are prepared. An antibody is considered to bind "specifically" to an antigen if the binding affinity between the antibody and the antigen is equal to, or greater than $10^5$ $M^{-1}$. The antibodies can be monoclonal or polyclonal. Preferably, the antibodies are monoclonal. More preferably, the antibodies are humanized antibodies.

Polyclonal anti-MRCK1 antibodies can be prepared by immunizing a suitable subject with MRCK1 or fragments thereof. The anti-MRCK1 antibody titer in the immunized subject can be monitored over the time using standard techniques, such as ELISA. The anti-MRCK1 antibody can be isolated from the immunized subject using well-known techniques.

In one embodiment, hybridomas capable of producing anti-MRCK1 antibodies are prepared. Purified MRCK1 or its variants, or fragments thereof, are used to immunize a vertebrate, such as a mammal. Suitable mammals include mice, rabbits and sheep. Preferably, the fragment used for immunization comprises at least 8 amino acid residues, more preferably at least 12 amino acid residues, highly preferably at least 16 amino acid residues, and most preferably at least 20 amino acid residues.

Immunogenic fragments (epitopes) of MRCK1 can be identified using well-known techniques. In general, any fragment of SEQ ID NO:2 can be used to raise antibodies specific to MRCK1. Preferred epitopes are regions that are located on the surface of MRCK1. These regions are usually hydrophilic.

Splenocytes are isolated from the immunized vertebrate and fused with an immortalized cell line (such as a myeloma) to form hybridomas. Preferably, the immortal cell line is derived from the same mammalian species as the lymphocytes. For example, murine hybridomas can be made by fusing an immortalized mouse cell line with lymphocytes isolated from a mouse that is immunized with an immunogenic preparation of the present invention. Preferred immortalized cell lines include mouse myeloma cell lines that are sensitive to culture medium containing hypoxanthine, aminopterin and thymidine ("HAT medium"). Suitable myeloma cell lines include, but are not limited to, the P3-NS1/1-Ag4-1, P3-x63-Ag8.653 or Sp210-Ag14 myeloma lines, all of which are available from ATCC. In one embodiment, HAT-sensitive mouse myeloma cells are fused to mouse splenocytes using polyethylene glycol ("PEG"). Hybridoma cells thus produced are selected against HAT medium, which kills unfused or unproductively fused myeloma cells. Hybridoma cells which produce monoclonal anti-MRCK1 antibodies are then detected by screening the hybridoma culture supernatants.

A monoclonal anti-MRCK1 antibody can also be prepared by screening a recombinant combinatorial immunoglobulin library (e.g., an antibody phase display library). Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612).

The anti-MRCK1 antibodies of the present invention also include "single-chain Fv" or "scFv." The scFv fragments comprise the $V_H$ and $V_L$ domains of an antibody. Generally, the scFv polypeptide further comprises a polypeptide linker between the $V_H$ and $V_L$ domains. The polypeptide linker enables the scFv to form the desired structure for antigen binding. Additionally, recombinant anti-MRCK1 antibodies, such as chimeric and humanized monoclonal antibodies, can be prepared, as appreciated by one of ordinary skill in the art.

Humanized antibodies are particularly desirable for therapeutic treatment of human subjects. Humanized forms of non-human (e.g., murine) antibodies are chimeric immunoglobulins, immunoglobulin chains, or fragments thereof (such as Fv, Fab, Fab', $F(ab')_2$ or other antigen-binding subsequences of antibodies) which contain minimal sequence derived from non-human immunoglobulin. Humanized antibodies are derived from human immunoglobulins in which the residues forming the complementary determining regions (CDRs) are replaced by the residues from CDRs of a non-human antibody, such as a mouse, rat or rabbit antibody having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. The humanized antibody can comprise at least one or two variable domains, in which all or substantially all of the CDR regions correspond to those of a non-human immunoglobulin and all or substantially all of the constant regions are those of a human immunoglobulin consensus sequence.

The humanized antibody preferably comprises at least a portion of an immunoglobulin constant region (Fc) of a human immunoglobulin.

Humanized antibodies can be produced using transgenic mice which are incapable of expressing endogenous immunoglobulin heavy and light chains but can express human heavy and light chains. The transgenic mice are immunized in the normal fashion with a selected antigen. Monoclonal antibodies directed against the antigen can be obtained using conventional hybridoma technology. The human immunoglobulin transgenes harbored in the transgenic mice rearrange during B cell differentiation, and subsequently undergo class switching and somatic mutation. Using this technique, therapeutically useful IgG, IgA and IgE antibodies can be prepared.

In addition, humanized antibodies which recognize a selected epitope can be generated using a technique referred to as "guided selection." In this approach a selected non-human monoclonal antibody, e.g., a murine antibody, is used to guide the selection of a humanized antibody recognizing the same epitope.

In a preferred embodiment, the antibodies to MRCK1 are capable of reducing or eliminating the biological function of MRCK1. Preferably, the antibodies reduce at least 25% of MCRK1 activity. More preferably, the antibodies reduce at least about 50% of the activity. Highly preferably, the antibodies reduce about 95-100% of MRCK1 activity.

Anti-MRCK1 antibodies can be used to isolate MRCK1. Suitable methods include affinity chromatography and immunoprecipitation. Moreover, anti-MRCK1 antibodies can be used to evaluate the expression level of MRCK1. Anti-MRCK1 antibodies can also be used to monitor MRCK1 level as part of a clinical testing procedure, or to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive materials include $^{125}I$, $^{131}I$, $^{35}S$ or $^{3}H$.

Anti-MRCK1 antibodies are also useful for targeting a therapeutic agent/drug to a particular cell or tissue. The therapeutic agent/drug may be coupled to an antibody, either covalently or non-covalently. For instance, a therapeutic agent can be coupled to an antibody via a linker group. A linker group can function as a spacer to separate the antibody from the agent so as to avoid interference with antibody's binding capabilities. The linker group can also serve to increase the chemical reactivity of a substituent on the agent or the antibody, and thus increase the coupling efficiency. A variety of bifunctional or polyfunctional reagents, either homo- or hetero-functional (such as those described in the catalog of the Pierce Chemical Co., Rockford, Ill.), can be employed as the linker group. Coupling may be effected, for example, through amino groups, carboxyl groups, sulfhydryl groups or oxidized carbohydrate residues. There are numerous references describing this methodology. See e.g., U.S. Pat. No. 4,671,958.

Where a therapeutic agent is more potent when free from the antibody, it may be desirable to use a linker group which is cleavable during or upon internalization into the target cell. A number of different cleavable linker groups have been described. The mechanisms for the intra-cellular release of an agent from these linker groups include cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), or by acid-catalyzed hydrolysis (e.g., U.S. Pat. No. 4,569,789).

It may also be desirable to couple more than one agent to an antibody. In one embodiment, multiple agents are coupled to one antibody molecule. In another embodiment, at least two different types of agents are coupled to one antibody. Regardless of the particular embodiment, immunoconjugates coupled with more than one agent can be prepared in a variety of ways, as appreciated by one of ordinary skill in the art.

Vectors, Expression Vectors and Gene Delivery Vectors

Another aspect of the invention pertains to vectors containing a polynucleotide encoding MRCK1 or a portion thereof. One type of vector is a "plasmid," which includes a circular double-stranded DNA into which additional DNA segments can be introduced. Vectors also include expression vectors and gene delivery vectors.

The expression vectors of the present invention comprise a polynucleotide encoding MRCK1 or a portion thereof. The expression vectors also include one or more regulatory sequences operably linked to the polynucleotide being expressed. These regulatory sequences are selected based on the type of host cells. It will be appreciated by those skilled in the art that the design of the expression vector depends on such factors as the choice of the host cells and the desired expression levels. MRCK1 can be expressed in bacterial cells such as *E. coli*, insect cells (using baculovirus expression vectors), yeast cells or mammalian cells. The expression vector can also be transcribed and translated in vitro, for example, by using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of the recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Suitable cleavage enzymes include Factor Xa, thrombin and enterokinase. Examples of fusion expression vectors include pGEX (Pharmacia Piscataway, N.J.), pMAL (New England Biolabs, Beverly, Mass.) and pRITS (Pharmacia, Piscataway, N.J.). Purified fusion proteins can be utilized in MRCK1 activity assays, or to generate antibodies specific for MRCK1.

Examples of suitable inducible non-fusion *E. coli* expression vectors include pTrc and pET 11d. Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HSLE174(DE3) from a resident prophage harboring a T7 gnl gene under the transcriptional control of the lacUV 5 promoter.

One strategy to maximize recombinant protein expression in *E. coli* is to express the protein in host bacteria that have an impaired capacity to proteolytically cleave the recombinant protein. Another strategy is to alter the polynucleotide sequence encoding the protein so that the individual codons for each amino acid are those preferentially utilized in *E. coli.*

In another embodiment, the MRCK1 expression vector is a yeast expression vector. Examples of yeast expression vectors include pYepSec1, pMFa, pJRY88, pYES2 (Invitrogen Corporation, San Diego, Calif.), and picZ (Invitrogen Corp, San Diego, Calif.).

Alternatively, MRCK1 or its variant can be expressed in insect cells using baculovirus expression vectors. Suitable baculovirus vectors include the pAc series and the $pV_L$ series.

In yet another embodiment, MRCK1 or its variant is expressed in mammalian cells using a mammalian expression vector. Examples of mammalian expression vectors include pCDM8 and pMT2PC. When used in mammalian cells, the expression vector's control functions are often provided by viral regulatory elements. For example, commonly used promoters are derived from polyoma, adenovirus 2, cytomegalovirus and Simian Virus 40.

In another embodiment, the mammalian expression vector contains tissue-specific regulatory elements. Examples of suitable tissue-specific promoters include the liver-specific albumin promoter, lymphoid-specific promoters, promoters of T cell receptors and immunoglobulins, neuron-specific promoters (e.g., the neurofilament promoter), pancreas-specific promoters, and mammary gland-specific promoters (e.g., milk whey promoter). Developmentally-regulated promoters are also contemplated, which include, for example, the α-fetoprotein promoter.

The present invention also provides a recombinant expression vector comprising a polynucleotide which encodes MRCK1 but is cloned into the expression vector in an antisense orientation. Regulatory sequences that are operatively linked to the antisense-oriented polynucleotide can be chosen to direct continuous expression of the antisense RNA molecule in a variety of cell types. Suitable regulatory sequences include viral promoters and/or enhancers. Regulatory sequences can also be chosen to direct constitutive, tissue specific or cell type specific expression of the antisense RNA. The antisense expression vector can be in the form of a recombinant plasmid, phagemid, or attenuated virus in which antisense polynucleotides are produced under the control of a highly efficient regulatory region.

The present invention further provides gene delivery vehicles for delivering polynucleotides to mammals. A polynucleotide sequence of the invention can be administered either locally or systemically via a gene delivery vehicle. Expression of the polynucleotide can be induced using endogenous mammalian or heterologous promoters. Expression of the polynucleotide in vivo can be either constituted or regulated. The gene delivery vehicles preferably are viral vectors, including retroviral, lentiviral, adenoviral, adeno-associated viral (AAV), herpes viral, or alphavirus vectors. The viral vectors can also be astrovirus, coronavirus, orthomyxovirus, papovavirus, paramyxovirus, parvovirus, picomavirus, poxvirus, or togavirus vectors.

Delivery of gene therapy constructs is not limited to the above mentioned viral vectors. Other delivery methods can also be employed. These methods include nucleic acid expression vectors, polycationic condensed DNA linked or unlinked to killed adenovirus, ligand linked DNA, liposome-DNA conjugates, gene guns, ionizing radiation, nucleic charge neutralization, or fusion with cell membranes. Naked DNA can also be employed. Uptake efficiency of the naked DNA may be improved using biodegradable latex beads. This method can be further improved by treating the beads to increase their hydrophobicity.

Regulatable Expression Systems

Another aspect of the present invention pertains to the use of regulatable expression systems to express desirable polynucleotides or polypeptides in cells. Systems suitable for this invention are briefly described below:

Tet-on/off system. The Tet-system is based on two regulatory elements derived from the tetracycline-resistance operon of the *E. coli* Tn10 transposon: the tet repressor protein (TetR) and the Tet operator DNA sequence (tetO) to which TetR binds (Gossen et al., Science, 268: 1766-1769, 1995). The system consists of two components, a "regulator" and a "reporter" plasmid. The "regulator" plasmid encodes a hybrid protein containing a mutated Tet repressor (rtetR) fused to the VP 16 activation domain of herpes simplex virus. The "reporter" plasmid contains a tet-responsive element (TRE), which controls the "reporter" gene of choice. The rtetR-VP16 fusion protein can only bind to the TRE, therefore activating the transcription of the "reporter" gene in the presence of tetracycline. The system has been incorporated into a number of viral vectors including retrovirus, adenovirus and AAV.

Ecdysone system. The ecdysone system is based on the molting induction system found in Drosophila, but modified for inducible expression in mammalian cells. The system uses an analog of the Drosophila steroid hormone ecdysone, muristerone A, to activate expression of the gene of interest via a heterodimeric nuclear receptor. Expression levels have been reported to exceed 200-fold over basal levels with no effect on mammalian cell physiology (No et al., Proc. Natl. Acad. Sci. USA, 93: 3346-3351, 1996).

Progesterone-system. The progesterone receptor is normally stimulated to bind to a specific DNA sequence and to activate transcription through an interaction with its hormone ligand. Conversely, the progesterone antagonist mifepristone (RU486) is able to block hormone-induced nuclear transport and subsequent DNA binding. A mutant form of the progesterone receptor that can be stimulated to bind through an interaction with RU486 has been generated. To generate a specific, regulatable transcription factor, the RU486-binding domain of the progesterone receptor has been fused to the DNA-binding domain of the yeast transcription factor GAL4 and the transactivation domain of the HSV protein VP 16. The chimeric factor is inactive in the absence of RU486. The addition of hormone, however, induces a conformational change in the chimeric protein, and this change allows binding to a GAL4-binding site and the activation of transcription from promoters containing the GAL4-binding site (Wang et al., Nat. Biotech., 15: 239-243, 1997).

Rapamycin-system. Immunosuppressive agents, such as FK506 and rapamycin, act by binding to specific cellular proteins and facilitating their dimerization. For example, the binding of rapamycin to FK506-binding protein (FKBP) results in its heterodimerization with another rapamycin binding protein FRAP, which can be reversed by removal of the drug. The ability to bring two proteins together by addition of a drug potentiates the regulation of a number of biological processes, including transcription. A chimeric DNA-binding domain has been fused to the FKBP, which enables binding of the fusion protein to a specific DNA-binding sequence. A transcriptional activation domain also has been fused to FRAP. When these two fusion proteins are co-expressed in the same cell, a fully functional transcription factor can be formed by heterodimerization mediated by addition of rapamycin. The dimerized chimeric transcription factor can then bind to a synthetic promoter sequence containing copies of the synthetic DNA-binding sequence. This system has been successfully integrated into adenoviral and AAV vectors. Long term regulatable gene expression has been achieved in both mice and baboons (Ye et al., Science, 283: 88-91, 1999).

Detection Methods

In patients with disorders related to the aberrant expression of MRCK1. The expression level of MRCK1 can be used as an indicator for detecting the presence of MRCK1-related diseases in humans. Detection and measurement of the relative amount of the MRCK1 gene product can be carried out using various methods known in the art.

Typical methodologies for detecting the transcription level of a gene include extracting RNA from a cell or tissue sample, hybridizing a labeled probe to the extracted RNA or derivative thereof (such as cDNA or cRNA), and detecting the probe. Suitable methods include Northern Blot and quantitative PCR or RT-PCR. In situ hybridization can also be used to detect the transcription level of the MRCK1 gene in human tissues.

Typical methodologies for detecting a polypeptide include extracting proteins from a cell or tissue sample, binding an antibody to the target polypeptide and detecting the antibody. Suitable methods include enzyme linked immunosorbent assays (ELISAs), Western blots, immunoprecipitations, and immunofluorescence. The antibody can be polyclonal, or preferably, monoclonal. The antibody can be an intact antibody, or a fragment thereof (e.g. Fab or $F(ab')_2$). The antibody can be labeled with a radioisotope, a fluorescent compound, an enzyme, an enzyme co-factor, or a detectable ligand. The term "labeled," with regard to a probe or antibody, is intended to encompass direct labeling such as through covalent coupling, as well as indirect labeling such as being mediated by another reagent which is directly labeled. Examples of indirect labeling include labeling a primary antibody using a fluorescently labeled secondary antibody, or attaching a DNA probe with a biotin which can be detected, for example, by a fluorescence-labeled streptavidin.

Preferably, the binding affinity of the antibody to MRCK1 is at least 105 M-1. More preferably, the binding affinity is at least $10^6$ $M^{-1}$. Other methods such as electrophoresis, chromatography or direct sequencing can also be used to detect the amount of a polypeptide in a biological sample. Anti-MRCK1 antibodies can also be directly introduced into a subject. The antibody can be labeled with a radioactive marker whose presence and location in the subject can be detected using standard imaging techniques.

In one embodiment, the genomic copies of the MRCK1 gene in the genome of a human subject may indicate the presence or predisposition of a disease. Detection of the presence or number of copies of the MRCK1 gene in the genome can be performed using methods known in the art. For instance, it can be assessed using Southern Blot. The probes for Southern Blot can be labeled with a radioisotope, a fluorescent compound, an enzyme, or an enzyme co-factor.

In the field of diagnostic assays, the above-described detection methods can be used to determine the severity of MRCK1-related diseases. A biological sample is isolated from a test subject, and the presence, quantity and/or activity of MRCK1 in the sample relative to a normal or control sample is evaluated. The expression level of MRCK1 in the biological sample can indicate the presence or severity of MRCK1-related diseases in the test subject. The term "biological sample" is intended to include tissues, cells or biological fluids isolated from the subject. A preferred biological sample is a serum sample isolated from the subject using conventional means.

Screening Methods

The present invention also provides methods for identifying MRCK1 modulators. The activity of MRCK1 can be evaluated using various methods, such as those disclosed in Leung et al., Mol. Cell Biol., 18:130-140, 1998, and Chen et al., J. Biol. Chem., 274: 19901-19905, 1999, both of which are incorporated herein by reference.

Suitable modulators include compounds or agents comprising therapeutic moieties, such as peptides, peptidomimetics, peptoids, polynucleotides, small molecules or other drugs. These moieties can either bind to MRCK1, or have a modulatory (e.g., stimulatory or inhibitory) effect on the activity of MRCK1. In one embodiment, the moieties have a modulatory effect on the interactions of MRCK1 with one or more of its natural substrates. These moieties can also exert a modulatory effect on the expression of MRCK1. The screen assays of the present invention comprise detecting the interactions between MRCK1 and test components.

The test compounds of the present invention can be either small molecules or bioactive agents. In a preferred embodiment, the test compound is a small organic or inorganic molecule. In another preferred embodiment, the test compound is a polypeptides, oligopeptides, polysaccharides, nucleotides or polynucleotides.

In accordance with one aspect of this invention, methods for screening for compounds that inhibit the biological activities of MRCK1 are provided. Pharmaceutical compositions comprising these compounds can subsequently be prepared. The screening method comprises (1) contacting a sample with a compound, and (2) comparing expression profile or biological activity of MRCK1 in the sample to determine whether the compound substantially decreases the expression level or activities of MRCK1. The screening method can be carried out either in vivo or in vitro.

The present invention further includes a method for screening for compounds capable of modulating the binding between MRCK1 and a binding partner. As used herein, the term "binding partner" refers to a bioactive agent which serves as either a substrate for MRCK1, or a ligand having a binding affinity to MRCK1. The bioactive agent may be selected from a variety of naturally-occurring or synthetic compounds, proteins, peptides, polysaccharides, nucleotides or polynucleotides.

Inhibitors of the expression, activity or binding ability of MRCK1 may be used as therapeutic compositions. These inhibitors can be formulated in suitable pharmaceutical compositions, as described herein below.

The present invention also provides methods for conducting high-throughput screening for compounds capable of inhibiting activity or expression of MRCK1. In one embodiment, the high-throughput screening method involves contacting test compounds with MRCK1, and then detecting the effect of the test compounds on MRCK1. Functional assays, such as cytosensor microphysiometer-based assays, calcium flux assays (e.g. FLIPR®, Molecular Devices Corp, Sunnyvale, Calif.), or the TUNEL assay, can be employed to measure MRCK1 cellular activity. Fluorescence-based techniques can be used for high-throughput and ultra high-throughput screening. They include, but are not limited to, BRET® and FRET® (both by Packard Instrument Co., Meriden, Conn.).

In a preferred embodiment, the high-throughput screening assay uses label-free plasmon resonance technology as provided by BIACORE® systems (Biacore International AB, Uppsala, Sweden). Plasmon free resonance occurs when surface plasmon waves are excited at a metal/liquid interface. By reflecting directed light from the surface as a result of contact with a sample, the surface plasmon resonance causes a change in the refractive index at the surface layer. The refractive index change for a given change of mass concentration at the surface layer is similar for many bioactive agents (including proteins, peptides, lipids and polynucleotides), and since the BIACORE® sensor surface can be functionalized to bind a variety of these bioactive agents, detection of a wide selection of test compounds can thus be accomplished.

Monitorin Efficacy of a Drug During Clinical Trials

Using the MRCK1 detection methods of this invention, the efficacy of a therapeutic agent for MRCK1-related diseases can be monitored during clinical trials. The therapeutic agent may be a drug, small molecule, agonist, antagonist, peptidomimetic, protein, peptide, or polynucleotide. The changes in the expression or activity of the MRCK1 gene in response to the treatment of the agent can be used to evaluate the therapeutic effect of the agent on patients with MRCK1-related diseases. In addition, the expression or activity of MRCK1 in response to the agent can be measured at various points during the clinical trial.

In a preferred embodiment, the method for monitoring the effectiveness of the therapeutic agent includes the steps of (i) obtaining a pre-administration sample from a subject; (ii) detecting the level of expression or activity of MRCK1 in the pre-administration sample; (iii) obtaining one or more post-administration samples from the subject; (iv) detecting the level of expression or activity of MRCK1 in the post-administration samples; (v) comparing the level of expression or activity of MRCK1 in the pre-administration sample to the level of expression or activity of MRCK1 in the post administration samples. The dose or frequency of the administration of the agent may be adjusted based on the effectiveness of the agent in a particular patient. Therefore, MRCK1 expression or activity can be used as an indicator of the effectiveness of a therapeutic agent for MRCK1-related diseases, even if the agent does not produce an observable phenotypic response.

Prognostic Assays

The detection methods described herein can be used to identify subjects having or at risk of developing MRCK1-related diseases. In addition, the detection methods can be used to determine whether an agent (e.g., an agonist, antagonist, peptidomimetic, protein, peptide, polynucleotide, small molecule, or other drug candidate) can be administered to a subject for effectively treating or preventing MRCK1-related diseases.

MRCK1 expression profiles at different progression stages of MRCK1-related diseases can be established. In addition, MRCK1 expression profiles in different patients who have different responses to a drug treatment are determined. A pattern may emerge such that a particular expression profile may be correlated to an increased likelihood of a poor prognosis. Therefore, the prognostic assay of the present invention may be used to determine whether a subject undergoing a treatment for an MRCK1-related disease has a poor outlook for long term survival or disease progression. Preferably, prognosis is performed shortly after diagnosis, such as within a few days after diagnosis. The result of prognosis can then be used to devise individualized treatment program, thereby enhancing the effectiveness of the treatment as well as the likelihood of long-term survival and well being.

The method of the invention can also be used to detect genetic alterations in the MRCK1 gene, thereby determining if a subject with the altered gene is at risk for damages characterized by aberrant regulation in MRCK1 activity or expression. In a preferred embodiment, the method includes detecting the presence or absence of a genetic alteration that affects the integrity of the MRCK1 gene, or detecting the aberrant expression of the MRCK1 gene. The genetic alteration can be detected by ascertaining the existence of at least one of the following: 1) deletion of one or more nucleotides from the MRCK1 gene; 2) addition of one or more nucleotides to the MRCK1 gene; 3) substitution of one or more nucleotides of the MRCK1 gene, 4) a chromosomal rearrangement in the MRCK1 gene; 5) alteration in the level of a messenger RNA transcript of the MRCK1 gene, 6) aberrant modification of the MRCK1 gene, 7) the presence of a non-wild-type splicing pattern of a messenger RNA transcript of the MRCK1 gene, 8) non-wild-type level MRCK1, 9) allelic loss of an MRCK1 gene, and 10) inappropriate post-translational modification of MRCK1.

In one embodiment, detection of the alteration involves the use of a probe/primer in a polymerase chain reaction (such as anchor PCR or RACE PCR) or alternatively, in a ligation chain reaction (LCR). LCR can be particularly useful for detecting point mutations in the MRCK1 gene. This method includes the steps of collecting a sample from a subject, isolating polynucleotides (e.g., genomic DNA, mRNA, or both) from the sample, contacting the polynucleotide with one or more primers which specifically hybridize to the MRCK1 gene or gene product, and detecting the presence or absence of an amplification product, or detecting the size of the amplification product and comparing its length to a control. It is understood that PCR and/or LCR can be used as a preliminary amplification step in conjunction with any other techniques described herein.

Alternative amplification methods include: self sustained sequence replication (Guatelli et al., Proc. Natl. Acad. Sci. USA, 87:1874-1878, 1990), transcriptional amplification system (Kwoh et al., Proc. Natl. Acad. Sci. USA, 86:1173-1177, 1989), and Q-Beta Replicase (Lizardi et al., Bio-Technology, 6:1197, 1988).

In another embodiment, mutations in the MRCK1 gene can be identified using restriction enzymes. Differences in restriction enzyme digestion patterns indicates mutation(s) in the MRCK1 gene or its transcripts. Moreover, sequence specific ribozymes can be used to detect the presence of specific mutations. See e.g., U.S. Pat. No. 5,498,531.

In yet another embodiment, genetic mutations in the MRCK1 gene can be identified using high density arrays which contain a large number of oligonucleotides probes. For example, genetic mutations in the MRCK1 gene can be identified in two dimensional arrays. In this example, a first hybridization array of probes is used to scan through long stretches of DNA in a sample and a control in order to identify base changes between the two sequences. This step allows the identification of point mutations. This step is followed by a second hybridization array that allows the characterization of specific mutations by using smaller and specialized probe arrays which are complementary to all variants or mutations detected. Each mutation array is composed of parallel probe sets, one complementary to the wild-type gene and the other complementary to the mutant gene.

In still another embodiment, any sequencing reactions known in the art can be used to directly sequence the MRCK1 gene in order to detect mutations. It is contemplated that any automated sequencing procedures can be utilized, including sequencing by mass spectrometry.

In one embodiment, protection from cleavage agents is used to detect mismatched bases in RNA/RNA or RNA/DNA heteroduplexes. In general, the "mismatch cleavage" technique involves forming heteroduplexes by hybridizing an RNA or DNA (labeled) containing the wild-type MRCK1 gene sequence to a potentially mutant RNA or DNA obtained from a tissue sample. The double-stranded duplexes are treated with an agent which cleaves single-stranded regions of the duplex. The agent may be RNase (for RNA/DNA duplexes), or S1 nuclease (for DNA/DNA hybrids). In one case, either DNA/DNA or RNA/DNA duplexes are treated with piperidine and hydroxylamine, or piperidine and osmium tetroxide, in order to digest mismatched regions. After the digestion, the resulting material is separated by size on a denaturing polyacrylamide gel from which the site(s) of mutation may be determined.

In a preferred embodiment, the mismatch cleavage reaction employs one or more proteins that recognize mismatched base pairs in double-stranded DNA. Examples of these proteins include "DNA mismatch repair" enzymes. For instance, the mutY enzyme of *E. coli* cleaves A at G/A mismatches, and the thymidine DNA glycosylase from HeLa cells cleaves T at G/T mismatches. In one case, cDNAs are prepared from mRNAs isolated from test cells. The cDNAs are then hybridized to a probe derived from the MRCK1 gene. The duplex thus formed is treated with a DNA mismatch repair enzyme, and the cleavage products, if any, can be detected from electrophoresis protocols or the like. See e.g., U.S. Pat. No. 5,459,039.

In another embodiment, alterations in electrophoretic mobility are used to identify mutations in the MRCK1 gene. Differences in electrophoretic mobility between mutant and wild-type polynucleotides can be detected using single strand conformation polymorphism (SSCP). The resulting alteration in electrophoretic mobility enables the detection of a single base change. The DNA fragments can be labeled or detected with probes. In one case, the sensitivity of the assay is enhanced by using RNA, in which the secondary structure is more sensitive to a change in sequence. In a preferred embodiment, the assay utilizes heteroduplex analysis to separate double-stranded heteroduplex molecules on the basis of changes in electrophoretic mobility (Keen et al., Trends Genet., 7:5, 1991).

In yet another embodiment, the movement of mutant or wild-type fragments is evaluated using denaturing gradient gel electrophoresis (DGGE). For this purpose, DNA fragments can be modified to insure that they do not completely denature. For instance, a GC clamp of approximately 40 GC-rich base pairs can be added to the DNA fragment using PCR. In a further embodiment, a temperature gradient is used in place of a denaturing gradient (Rosenbaum and Reissner Biophys Chem, 265:12753, 1987).

Examples of other techniques for detecting point mutations include, but are not limited to, selective oligonucleotide hybridization, selective amplification, or selective primer extension. In one embodiment, oligonucleotide primers for specific amplification carry the mutation of interest in the center of the molecule (so that amplification depends on differential hybridization) or at the extreme 3'end of one primer where, under appropriate conditions, mismatch can prevent or reduce polymerase extension. See e.g., Saiki et al., Proc. Natl. Acad. Sci USA, 86:6230, 1989. In addition, it may be desirable to introduce a novel restriction site in the region of the mutation to create cleavage-based detection.

The methods described herein can be performed using prepackaged diagnostic kits which comprise at least one polynucleotide probe or one antibody of the present invention. These kits can be used in clinical settings to diagnose subjects exhibiting symptoms or family history of an MRCK1-related disease. Any cell type or tissue in which MRCK1 is expressed can be used for prognostic or diagnostic purposes.

Prophylactic Methods

This invention also provides methods for preventing diseases associated with aberrant MRCK1 expression or activity. The methods comprise administering to a target subject an agent which modulates MRCK1 expression or activity.

Subjects at risk of diseases which are caused by or attributed to aberrant MRCK1 expression or activity can be identified using the diagnostic or prognostic assays described herein. A prophylactic agent can be administered prior to the manifestation of MRCK1-related disease symptoms in order to prevent or delay MRCK1-related diseases. Suitable prophylactic agents include mutant MRCK1 proteins, MRCK1 antagonist agents, or MRCK1 antisense polynucleotides.

The prophylactic methods of this invention can be specifically tailored or modified, based on knowledge obtained from the study of pharmacogenomics. Pharmacogenomics includes the application of genomics technologies, such as gene sequencing, statistical genetics, and gene expression analysis, to drugs which are either in clinical development or on the market. Pharmacogenomics can be used to determine a subject's response to a drug (e.g., a subject's "drug response phenotype" or "drug response genotype"). Thus, another aspect of this invention is to provide methods for tailoring an individual's prophylactic or therapeutic treatment using MRCK1 modulators according to the individual's drug response genotype. Pharmacogenomics allows a clinician or physician to target prophylactic or therapeutic treatments to subjects who will most benefit from the treatment and to avoid treatment of subjects who will experience toxic drug-related side effects.

One pharmacogenomics approach to identify genes that predict drug response, known as "a genome-wide association," relies primarily on a high-resolution map of the human genome consisting of already known gene-related sites (e.g., a "bi-allelic" gene marker map which consists of 60,000-100,000 polymorphic or variable sites on the human genome, each of which has two variants). Such a high-resolution genetic map can be compared to a map of the genome of each of a statistically substantial number of subjects taking part in a Phase 11/111 drug trial in order to identify genes associated with a particular observed drug response or side effect. Alternatively, such a high resolution map can be generated from a combination of some ten-million known single nucleotide polymorphisms (SNPs) in the human genome. A "SNP" is a common alteration that occurs in a single nucleotide base in a stretch of DNA. For example, a SNP may occur once per every 1000 bases of DNA. A SNP may be involved in a disease process. However, the vast majority of SNPs may be not related to diseases. Given a genetic map based on the occurrence of SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals. Thus, mapping of the MRCK1 gene to SNP maps of patients with MRCK1-related diseases may facilitate the identification of drug-response-prediction genes.

Alternatively, the "candidate gene approach" can be utilized to identify genes that predict drug response. According to this method, if a gene that encodes a drug target is known, all common variants of that gene can be easily identified in the population. It then can be determined if a particular drug response is associated with one version of the gene versus another.

The activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYPZC19) has provided an explanation as to why some subjects do not obtain the expected drug effects or show exaggerated drug response and serious toxicity after taking the standard and safe dose of a drug. These polymorphisms are expressed in two phenotypes in the population, extensive metabolizer and poor metabolizer. The prevalence of poor metabolizer phenotypes is different among different populations. For example, the gene coding for CYP2D6 is highly polymorphic and several mutations have been identified in poor metabolizers, which all lead to the absence of functional CYP2D6. Poor metabolizers of CYP2D6 and CYP2C 19 quite frequently experience exaggerated drug response and side effects when they receive standard doses. If a metabolite is the active therapeutic moiety, poor metabolizers show no therapeutic response. The other extreme are the so called ultra-rapid metabolizers who do not respond to standard doses. Recently, the molecular basis of ultra-rapid metabolism has been identified to be due to CYP2D6 gene amplification.

In one embodiment, the "gene expression profiling" method can be utilized to identify genes that predict drug response. In this regard, the gene expression profile of an animal dosed with a drug can give an indication of whether the gene pathways related to toxicity have been turned on.

Information generated from the above pharmacogenomics approaches can be used to determine the appropriate dosage or treatment regimen suitable for a particular individual. This knowledge can avoid adverse reactions or therapeutic failure, and therefore enhance therapeutic or prophylactic efficiency when treating a subject with an MRCK1 modulator.

Therapeutic Methods

As described above, the present invention includes therapeutic methods for treating a subject at risk for, susceptible to, or diagnosed with MRCK1-related diseases. The therapeutic methods can be individually tailored based on the subject's drug response genotype. Typically, the therapeutic methods comprise modulating the expression or activity of MRCK1 in the subject. In one embodiment, the method comprises contacting a plurality of cells in the subject with an agent that inhibits the expression or activity of MRCK1. Suitable agents include polynucleotides (e.g., an antisense oligonucleotides of MRCK1), polypeptides (e.g., a dominant negative mutant of MRCK1), or polysaccharides, naturally-occurring target molecules of MRCK1 protein (e.g., an MRCK1 protein substrate or receptor), anti-MRCK1 antibodies, MRCK1 antagonists, or other small organic and inorganic molecule. They may also include vectors comprising polynucleotides encoding MRCK1 inhibitors or antisense sequences. Moreover, the agents can be anti-MRCK1 antibodies conjugated with therapeutic moieties. Suitable agents can be identified using the screening assays of the present invention.

Pharmaceutical Compositions

The present invention is further directed to pharmaceutical compositions comprising an MRCK1 modulator and a pharmaceutically acceptable carrier. As used herein, a "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active modulator (e.g., an anti-MRCK1 antibody, an MRCK1 activity inhibitor, or a gene therapy vector expressing antisense nucleotide to MRCK1) in the required amount in an appropriate solvent, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active, ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the bioactive compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the therapeutic moieties, which may contain a bioactive compound, are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

Kits

The invention also encompasses kits for detecting the presence of an MRCK1 gene product in a biological sample. An example kit comprises reagents for assessing expression of MRCK1 at mRNA or protein level. Preferably, the reagents include an antibody or fragment thereof, wherein the antibody or fragment specifically binds to MRCK1. Optionally, the kits may comprise a polynucleotide probe capable of specifically binding to a transcript of the MRCK1 gene. The kit may also contain means for determining the amount of MRCK1 protein or mRNA in the test sample, and/or means for comparing the amount of MRCK1 protein or mRNA in the test sample to a control or standard. The compound or agent can be packaged in a suitable container.

The invention further provides kits for assessing the suitability of each of a plurality of compounds for inhibiting MRCK1-related diseases in cells or human subjects. Such kits include a plurality of compounds to be tested, and a reagent (such as an antibody specific to MRCK1 proteins, or a polynucleotide probe or primer capable of hybridizing to the MRCK1 gene) for assessing expression of MRCK1.

It should be understood that the above-described embodiments are given by way illustration, not limitation. Various changes and modifications within the spirit and scope of the present invention will become apparent to those skilled in the art from the present description.

Host Cells

Another aspect of the invention pertains to host cells into which a polynucleotide molecule of the invention is introduced, e.g., an MRCK1 gene or homolog thereof, within an expression vector, a gene delivery vector, or a polynucleotide molecule of the invention containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an MRCK1 gene can be expressed in bacterial cells such as *E. coli*, insect cells, yeast or mammalian cells (e.g., Chinese hamster ovary cells (CHO), COS cells, Fischer 344 rat cells, HLA-B27 rat cells, HeLa cells, A549 cells, or 293 cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign polynucleotide (e.g., DNA) into a host cell, including calcium phosphate or calcium chloride co-precipitation, DEAE-dextran-mediated transfection, lipofection, or electoporation.

For stable transfection of mammalian cells, it is known that, depending upon the expression vector and transfection technique used, only a small fraction of cells may integrate the foreign DNA into their genome. In order to identify and select these integrants, a gene that encodes a selectable flag (e.g., resistance to antibiotics) is generally introduced into the host cells along with the gene of interest. Preferred selectable flags include those which confer resistance to drugs, such as G418, hygromycin and methotrexate. Polynucleotides encoding a selectable flag can be introduced into a host cell by the same vector as that encoding MRCK1 or can be introduced by a separate vector. Cells stably transfected with the introduced polynucleotide can be identified by drug selection (e.g., cells that have incorporated the selectable flag gene will survive, while the other cells die).

A host cell of the invention, such as a prokaryotic or eukaryotic host cell in culture, can be used to produce (i.e., express) MRCK1. Accordingly, the invention further provides methods for producing MRCK1 using the host cells of the invention. In one embodiment, the method comprises culturing the host cell of invention (into which a recombinant expression vector containing an MRCK1 gene has been introduced) in a suitable medium such that MRCK1 is produced. In another embodiment, the method further comprises isolating MRCK1 from the medium or the host cell.

Transgenic and Knockout Animals

The host cells of the invention can also be used to produce non-human transgenic animals. For example, in one embodiment, a host cell of the invention is a fertilized oocyte or an embryonic stem cell into which MRCK1-coding sequences have been introduced. Such host cells can then be used to create non-human transgenic animals in which exogenous sequences encoding MRCK1 have been introduced into their genome or homologous recombinant animals in which endogenous sequences encoding MRCK1 have been altered. Such animals are useful for studying the function and/or activity of MRCK1 and for identifying and/or evaluating modulators of MRCK1 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" or "knockout animal" is a non-human animal, preferably a mammal, more preferably a mouse, in which an endogenous MRCK1 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing an MRCK1-encoding polynucleotide into the mate pronuclei of a fertilized oocyte, e.g., by microinjection or retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to a transgene to direct expression of MRCK1 to particular cells. Methods for generating transgenic animals via embryo manipulation and microinjection, particularly animals such as mice, have become conventional in the art. Similar methods are used for production of other transgenic animals. A transgenic founder animal can be identified based upon the presence of a transgene of the invention in its genome and/or expression of mRNA corresponding to a gene of the invention in tissues or cells of the animals. A transgenic founder animal can then be used to breed additional animals carrying the transgene. Moreover, transgenic animals carrying a transgene encoding MRCK1 can further be bred to other transgenic animals carrying other transgenes.

To create a homologous recombinant animal (knockout animal), a vector is prepared which contains at least a portion of a gene of the invention into which a deletion, addition or substitution has been introduced to thereby alter, e.g., functionally disrupt, the gene. The gene can be a human gene, but more preferably, is a non-human homolog of a human gene of the invention (e.g., a homolog of the MRCK1 gene). For example, a mouse gene can be used to construct a homologous recombination polynucleotide molecule, e.g., a vector, suitable for altering an endogenous gene of the invention in the mouse genome. In a preferred embodiment, the homologous recombination polynucleotide molecule is designed such that, upon homologous recombination, the endogenous gene of the invention is functionally disrupted (i.e., no longer encodes a functional protein; also referred to as a "knockout" vector). Alternatively, the homologous recombination polynucleotide molecule can be designed such that, upon homologous recombination, the endogenous gene is mutated or otherwise altered but still encodes functional protein (e.g., the upstream regulatory region can be altered to thereby alter the expression of the endogenous MRCK1 gene). In the homologous recombination polynucleotide molecule, the altered portion of the gene of the invention is flanked at its 5' and 3' ends by additional polynucleotide sequence of the gene of the invention to allow for homologous recombination to occur between the exogenous gene carried by the homologous recombination polynucleotide molecule and an endogenous gene in a cell, e.g., an embryonic stem cell. The additional flanking polynucleotide sequence is of sufficient length for successful homologous recombination with the endogenous gene.

Typically, several kilobases of flanking DNA (both at the 5' and 3' ends) are included in the homologous recombination polynucleotide molecule. The homologous recombination polynucleotide molecule is introduced into embryonic stem cells by electroporation. The cells in which the introduced gene has homologously recombined with the endogenous gene are selected. The selected cells can then be injected into a blastocyst of an animal (e.g., a mouse) to form aggregation chimeras. A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the homologously recombined DNA. Methods for constructing homologous recombination polynucleotide molecules, e.g., vectors, or homologous recombinant animals are well-known in the art.

In another embodiment, transgenic non-human animals can be produced which contain selected systems which allow for regulated expression of the transgene. One example of such a system is the cre/loxP recombinase system of bacteriophage P1. Another example of a recombinase system is the FLP recombinase system of *Saccharomyces cerevisiae* (See e.g., O'Gorman et al., Science, 251: 1351-1355, 1991). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al., Nature, 385:810-813, 1997, and PCT International Publication Nos. WO97/07668 and WO97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

EXAMPLES

Example 1

Identification of MRCK1 Sequence in Human Genome Database.

The nucleic acid sequence of MRCK1 is obtained from a newly developed genomic prediction pipeline. Briefly, the X-ray crystal structures of the catalytic domains of protein kinases were collected and aligned together according to their structural identity/similarities. The alignment was converted into a "scoring matrix" which carried the structural profile of the kinase catalytic domains. This scoring matrix was then used to search the Celera Human Genome database for sequences that have kinase catalytic domains.

Example 2

BLAST Analysis

Sequence alignments between MRCK1 and other sequences in GenBank database were performed using the standard protein-protein BLAST (blastp), standard nucleotide-nucleotide BLAST (blastn), BLAST2 Sequences, and human genome BLAST programs that are available at NCBI's BLAST website.

A standard protein-protein BLAST search in the "nr" database (available at NCBI's BLAST website) with "Filter" setting unchecked, "Expect" setting at 10.0, "Word Size" setting at 3, "Matrix" setting at BLOSUM62, "Gap costs" setting at Existence: 11 and Extension: 1, revealed that MRCK1 shares sequence homologies with rat MRCK alpha (Entrez accession number: NP-_446109.1, FIGS. 1 and 2), a putative mouse MRCK alpha (XP_140553.1, 70% alignment to amino acid residues 40-1548 of MRCK1), and two putative human MRCK-related proteins (Entrez accession number Y12337, 100% alignment to amino acid residues 113-399 of MRCK1 and Entrez accession number U59305, 65% alignment to amino acid residues 40-434 of MRCK1).

A conserved domain search was performed within the standard protein-protein BLAST search with the RPS-BLAST 2.2.3 [Apr-24-2002] program. The amino acid residues 71-337 of MRCK1 are highly homologous to the consensus sequence of the catalytic domain of a family of ser/thr protein kinase (accession number smart00220, 100% alignment, Figure.

3), the pkinase domain (accession number pfam00069, 100% alignment, FIG. 4), and the catalytic domain of tyrosine kinase (accession number smart00219, 89.1% alignment, FIG. 5). The amino acid residues 339-398 of MRCK1 are highly homologous to the consensus sequence of an extension to ser/thr type protein kinase (accession number smart00133, 95.2% alignment, FIG. 6). The amino acid residues 339-398 of MRCK1 also aligns to the consensus sequence of the protein kinase C terminal domain (accession number pfam00433, 91.0% alignment, FIG. 7). The amino acid residues 882-920 of MRCK1 aligns to the consensus sequence of DAG_PE-binding domain (accession number pfam00130, 78.0% alignment, FIG. 8). The amino acid residues 953-1060 of MRCK1 aligns to the consensus sequence of the Pleckstrin homology (PH) domain (accession number smart00233, 87.5% alignment, FIG. 9). The amino acid residues 953-1060 of MRCK1 also aligns to another consensus sequence of the PH domain (accession number pfam00169, 88.0% alignment, FIG. 10). The amino acid residues 1102-1345 of MRCK1 aligns to the consensus sequence of the CNH domain (accession number pfam00780, 85.7% alignment, FIG. 11). The amino acid residues 1440-1471 of MRCK1 aligns to the consensus sequence of the P21-Rho-binding domain (accession number smart00285, 86.1% alignment, FIG. 12). The amino acid residues 648-786 of MRCK1 also weakly aligns to the consensus sequence of the myosin tail (accession number pfam01576, 17.8% alignment, FIG. 13).

A standard nucleotide-nucleotide BLAST search in the "geneseqn" database (available at NCBI's BLAST website) with "Matrix" setting at blastn matrix: 1-3, "Gap Penalties" setting at Existence: 5, Extension: 2, identified significant alignment of MRCK1 nucleotide sequence to the human kinase polypeptide PKIN-20 from PCT patent application WO02/08399 (Entrez accession number: AAD30567). Further analysis using Pairwise BLAST program (BLASTN setting: Match: 1, Mismatch: −2, gap open: 5, gap extension: 2, x_dropoff: 500, expect: 10.0, wordsize: 11, filter: unchecked; BALSTP setting: Matrix: BLOSUM62, gap open: 11, gap extension: 1, x_dropoff: 50, expect: 10.0, wordsize: 3, filter: unchecked) showed sequence homologies of 95% at nucleotide level and 90% at amino acid level between MRCK1 and PKIN-20. The amino acid and nucleotide sequences of PKIN-20 are recited in SEQ ID NOS:4 and 5. The standard nucleotide-nucleotide BLAST search in the "geneseqn" database also revealed significant sequence homologies between MRCK1 and a human Cdc42-binding kinase homologue-encoding cDNA (Entrez accession number: ABA08323, SEQ ID NO:6, 99% identities to nucleotide residues 2741-4398 of MRCK1).

A human genome search was carried out using blastn program with Expect setting at 0.01, Filter setting at default, Descriptions setting at 100, and Alignment settings at 100. The MRCK1 gene was mapped to or near loci 11p13 of human chromosome 11. Specifically, MRCK1 gene is located between genes LOC196204 and LOC143732, and overlaps with gene LOC196205. The exons/introns in the MRCK1 gene were determined using the program "sim4" described by Florea et al., in "A computer program for aligning a cDNA sequence with a genomic DNA sequence" Genome Res. 8:967-974, 1998.

Example 3

Hydrophobicity Analysis

The hydrophobicity profile of MRCK1 sequence (FIG. 14) was generated using the GES (Goldman, Engelman and Steitz) hydrophobicity scale (Engelman et al., Ann. Rev. Biophys. Biophys. Chem. 15:321-353, 1986). Briefly, the GES scale is used to identify nonpolar transbilayer helices. The curve is the average of a residue-specific hydrophobicity scale over a window of 20 residues. When the line is in the upper half of the frame (positive), it indicates a hydrophobic region and when it is in the lower half (negative), a hydrophilic region.

In FIG. 14, the X-axis represents the length of the protein in amino acids (aa), while the Y-axis represents the GES score. The curve line shows the GES pattern of the entire protein, while the straight line represents certain cutoff for potential membrane spanning domains. The hydrophobicity profile indicates that MRCK1 is probably not a membrane protein.

Example 4

MTN and MTA Analysis

Figure 15:
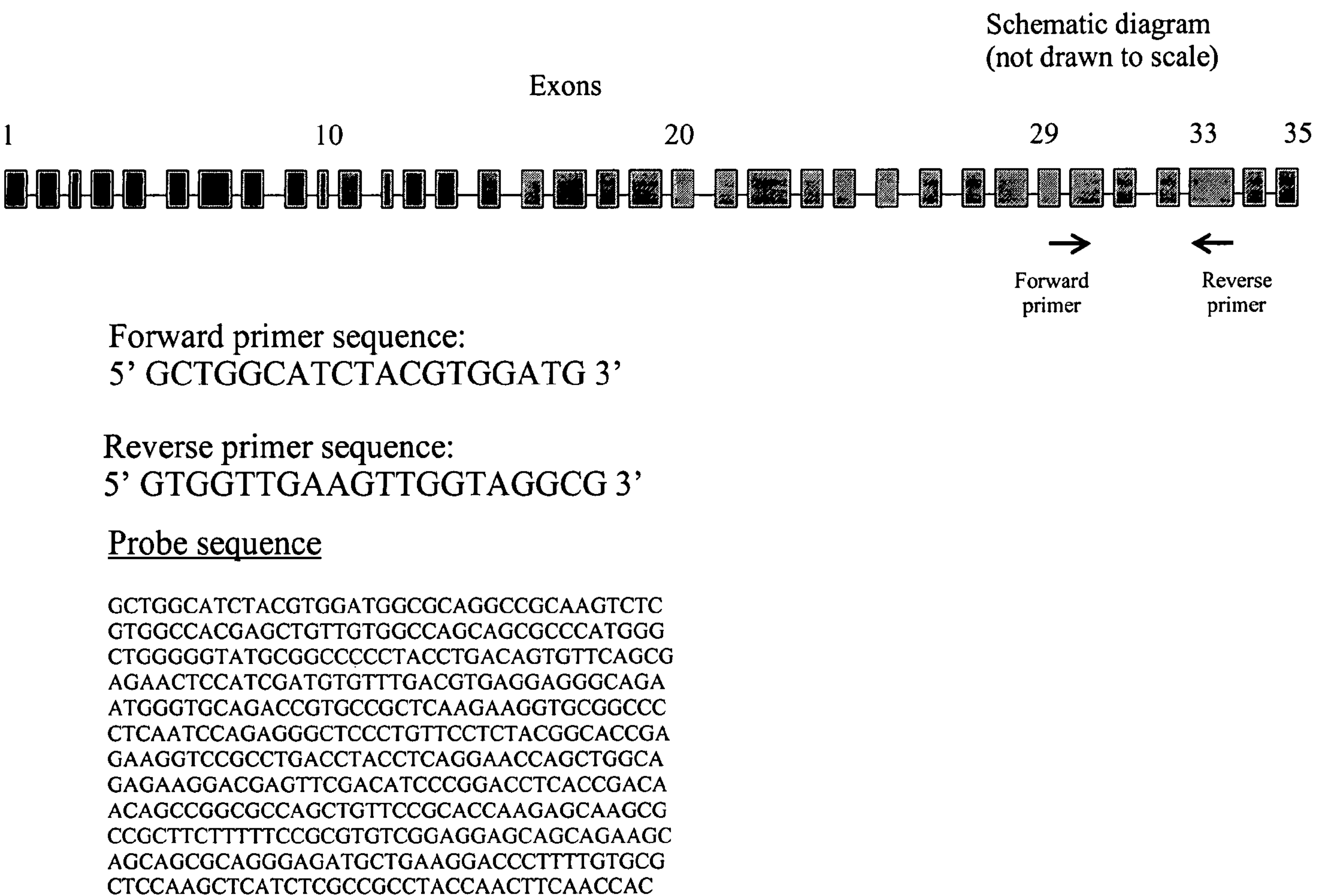
FIG. 15 shows the position and nucleotide sequence of human MRCK1 probe and PCR primers used for the amplification of the probe sequences.

The DNA probe for the MTN and MTA analysis is a PCR amplified 447 nucleotide fragment (SEQ ID NO:9) from human cDNA library. The probe located at exon 29-33, pos#3898-4344 of the MRCK1 cDNA. The PCR primers were designed based on the cDNA prediction. The Forward primer sequence is: 5' GCTGGCATCTACGTGGATG 3' (SEQ ID NO:7). The reverse primer sequence is: 5' GTGGTTGAAGTTGGTAGGCG 3' (SEQ ID NO:8). The PCR amplified probe was sequence verified. The positions of the probe and the primers relative to the MRCK1 gene are shown in FIG. 15.

The MTN analysis was performed using the Multiple Tissue Northern (MTN®) Blot Kit (Clontech Laboratories, Inc., Palo Alto, Calif.) under conditions specified in the User Manual. Briefly, the human MRCK1 probe was labeled with $^{32}P$. The MTN Blot was prehybridized in ExpressHyb solution at 68° C. for 30 min, and then hybridized with the labeled probe at 68° C. for 1 hr. The blot was washed two times with Wash Solution 1 for 30 min at room temperature and two times with Wash Solution 2 for 30 min at 50° C., and was then exposed to X-ray film. Two transcripts of MRCK1, a 4 kb and a 6 kb transcript, were detected in human brain, heart, skeletal muscle, colon, thymus, spleen, kidney, liver, small intestine, placenta, lung, and peripheral blood leukocyte. The highest expression was in placenta while the lowest expression was in small intestine. The MTA analysis was performed using the Multiple Tissue Expression (MTE®) Array Kit (Clontech Laboratories, Inc., Palo Alto, Calif.) under conditions specified in the User Manual. Briefly, the MTE array was hybridized to $^{32}P$-labeled human MRCK1 probe in ExpressHyb solution at 65° C. overnight with continuous agitation. The array was washed four times with Wash Solution 1 for 20 min at 65° C. and two times with Wash Solution 2 for 20 min at 55° C., and was then exposed to X-ray film. MRCK1 expression was found in all 76 tissues contained in the array.

Having described the preferred embodiments of compositions, organisms and methodologies employing a novel human gene MRCK1 (which are intended to be illustrative and not limiting), it is noted that modifications and variations can be made by persons skilled in the art in light of the above teachings. Therefore, it is understood that changes may be made in the particular embodiments disclosed which are within the scope and spirit of what is described as defined by the appended claims.

What is claimed is:

1. An isolated polypeptide comprising SEQ ID NO:2.

* * * * *